United States Patent
Njar et al.

(10) Patent No.: US 9,694,005 B2
(45) Date of Patent: Jul. 4, 2017

(54) NONSTEROIDAL AND STEROIDAL COMPOUNDS WITH POTENT ANDROGEN RECEPTOR DOWN-REGULATION AND ANTI PROSTATE CANCER ACTIVITY

(71) Applicant: University of Maryland, Baltimore, Baltimore, MD (US)

(72) Inventors: Vincent C. O. Njar, Glen Burnie, MD (US); Puranik Purushottamachar, Gaithersburg, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/781,437

(22) PCT Filed: Apr. 4, 2014

(86) PCT No.: PCT/US2014/033063
§ 371 (c)(1),
(2) Date: Sep. 30, 2015

(87) PCT Pub. No.: WO2014/165815
PCT Pub. Date: Oct. 9, 2014

(65) Prior Publication Data
US 2016/0038476 A1    Feb. 11, 2016

Related U.S. Application Data

(60) Provisional application No. 61/808,345, filed on Apr. 4, 2013, provisional application No. 61/808,902, filed on Apr. 5, 2013.

(51) Int. Cl.
| | |
|---|---|
| A61K 31/4725 | (2006.01) |
| A61K 31/4164 | (2006.01) |
| A61K 31/4184 | (2006.01) |
| A61K 31/4409 | (2006.01) |
| C07D 401/14 | (2006.01) |
| C07D 403/12 | (2006.01) |
| C07D 235/08 | (2006.01) |
| C07D 401/10 | (2006.01) |
| C07D 403/10 | (2006.01) |
| C07J 43/00 | (2006.01) |

(52) U.S. Cl.
CPC ...... *A61K 31/4725* (2013.01); *A61K 31/4164* (2013.01); *A61K 31/4184* (2013.01); *A61K 31/4409* (2013.01); *C07D 235/08* (2013.01); *C07D 401/10* (2013.01); *C07D 401/14* (2013.01); *C07D 403/10* (2013.01); *C07D 403/12* (2013.01); *C07J 43/003* (2013.01)

(58) Field of Classification Search
CPC ............ A61K 31/4164; A61K 31/4184; A61K 31/4409; A61K 31/4725; C07D 235/08; C07D 401/10; C07D 401/14; C07D 403/10; C07D 403/12; C07J 43/003
See application file for complete search history.

(56) References Cited

U.S. PATENT DOCUMENTS

| | | | |
|---|---|---|---|
| 5,128,356 | A | 7/1992 | Naka et al. |
| 5,360,809 | A | 11/1994 | Axelsson et al. |
| 2007/0066606 | A1 | 3/2007 | Stahle et al. |
| 2010/0048913 | A1 | 2/2010 | Brodie et al. |

FOREIGN PATENT DOCUMENTS

| | | |
|---|---|---|
| EP | 0 392 317 A2 | 10/1990 |
| WO | 2006/093993 A1 | 9/2006 |
| WO | 2009/100438 A2 | 8/2009 |

OTHER PUBLICATIONS

Fernandez-Rhodes et. al., Lancet Neurology, 2011, Elsevier Ltd., vol. 10(2), pp. 140-147 (pp. 1-19).*
Chao et. al., Cancer, 1996, American Cancer Society, vol. 77(4), pp. 635-639.*
Leaf, Fortune, 2004, Time Inc., pp. 1-28.*
Chabner et. al., Nature Reviews Cancer, 2005, Nature Publishing Group, vol. 5, pp. 65-72.*
International Search Report dated Nov. 7, 2014, issued in counterpart Application No. PCT/US2014/033063 (5 pages).
Extended (Supplementary) Search Report dated Jan. 11, 2017, issued in European Application No. 14779540.5 (13 pages).
Mizuno, Cassia S. et al., "Design, synthesis, and docking studies of telmisartan analogs for the treatment of metabolic syndrome", Medicinal Chemistry Research, Birkhauser-Verlag, Boston, vol. 18, No. 8, Jan. 27, 2009 (pp. 611-628).
Lesuisse, Dominique et al., "Biphenyls as Surrogates of the Steroidal Backbone. Part 2: Discovery of a Novel Family of Non-steroidal 5-α-Reductase Inhibitors", Bioorganic & Medicinal Chemistry Letters, vol. 11, No. 13, Jul. 1, 2001 (pp. 1713-1716).
Partial Supplementary European Search Report dated Oct. 5, 2016, issued in European Patent Application No. 14779540.5. (9 pages).
C. Mizuno, et al."Design synthesis, and docking studies of telmisartan analogs for the treatment of metabolic syndrome", Medicinal Chemistry Research, 2009, vol. 18, No. 8, pp. 611-628. Cited in Partial Supplementary European Search Report.

(Continued)

*Primary Examiner* — Sarah Pihonak
(74) *Attorney, Agent, or Firm* — Westerman, Hattori, Daniels & Adrian, LLP

(57) ABSTRACT

Nonsteroid and steroid compounds that cause down-regulation of the androgen receptor (AR), both full length and splice variant, induce apoptosis and inhibit proliferation of inhibiting proliferation and migration of androgen sensitive cancer cells. The steroid compounds and nonsteroid compounds may be agents for the prevention and/or treatment of cancer, including prostate cancer, castration resistant prostate cancer, bladder cancer, pancreatic cancer, hepatocellular carcinoma, benign prostatic hyperplasia (BPH), Kennedy's disease, androgenetic alopecia, breast cancer, androgen-insensitive syndrome, and spinal and bulbar muscular atrophy.

10 Claims, 15 Drawing Sheets

(56) References Cited

OTHER PUBLICATIONS

D. Lesuisse et al. Bipheyls as Surrogates of the Steroidal Backbone. Part 2: Discovery of a Novel Family of Non-sχteroidal 5-X-Reductase Inhibitors, Biooranic & Medicinal Chemistry Letters, vol. 11, No. 13, 2001, pp. 1713-1716. Cited in Partial Supplementary European Search Report.

Office Action dated Oct. 25, 2016, issued in counterpart Australian Patent Application 2014247941. (4 pages).

* cited by examiner

FIG.3 Flexible alignment with VN/124-1

All nonsteroidal Biphenyl

Naphthylbiphenyl Stilbene

Effects of Compounds on Transcriptional Activity of Luciferase Mediated Via LNCaP-AR in LNCaP-ARR2-lu Prostate Cancer Cells Effects of Compounds on Oncogenes
CWR22RV1

Effects of Compounds on Oncogenes
LNCAP

Effects of Compounds on Oncogenes
CWR22RV1

Effects of Compounds on Oncogenes
LNCAP

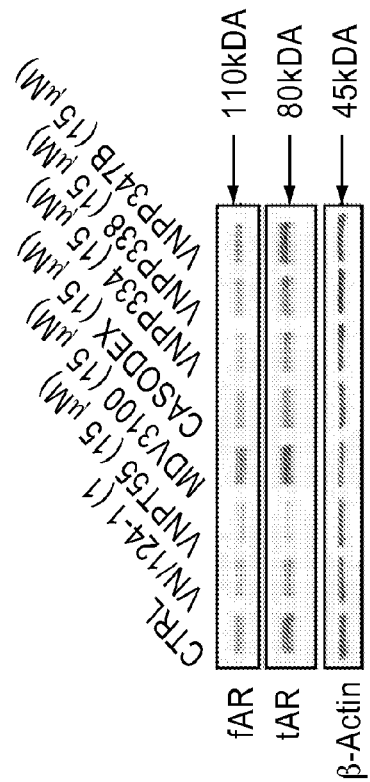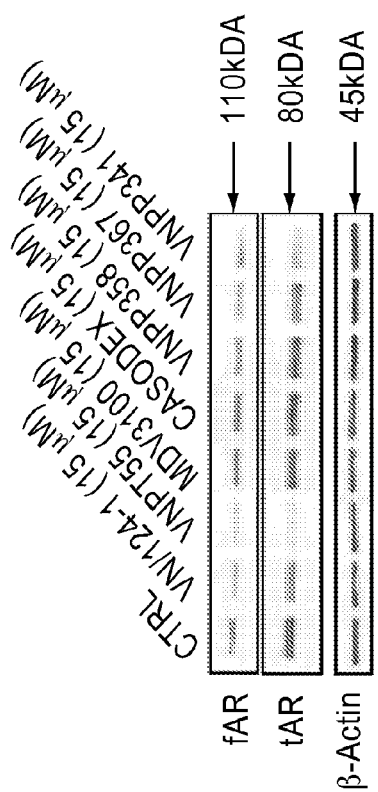

Effects of Compounds on Oncogenes
LNCaP

Effects of Compounds on Oncogenes
CWR22RV1

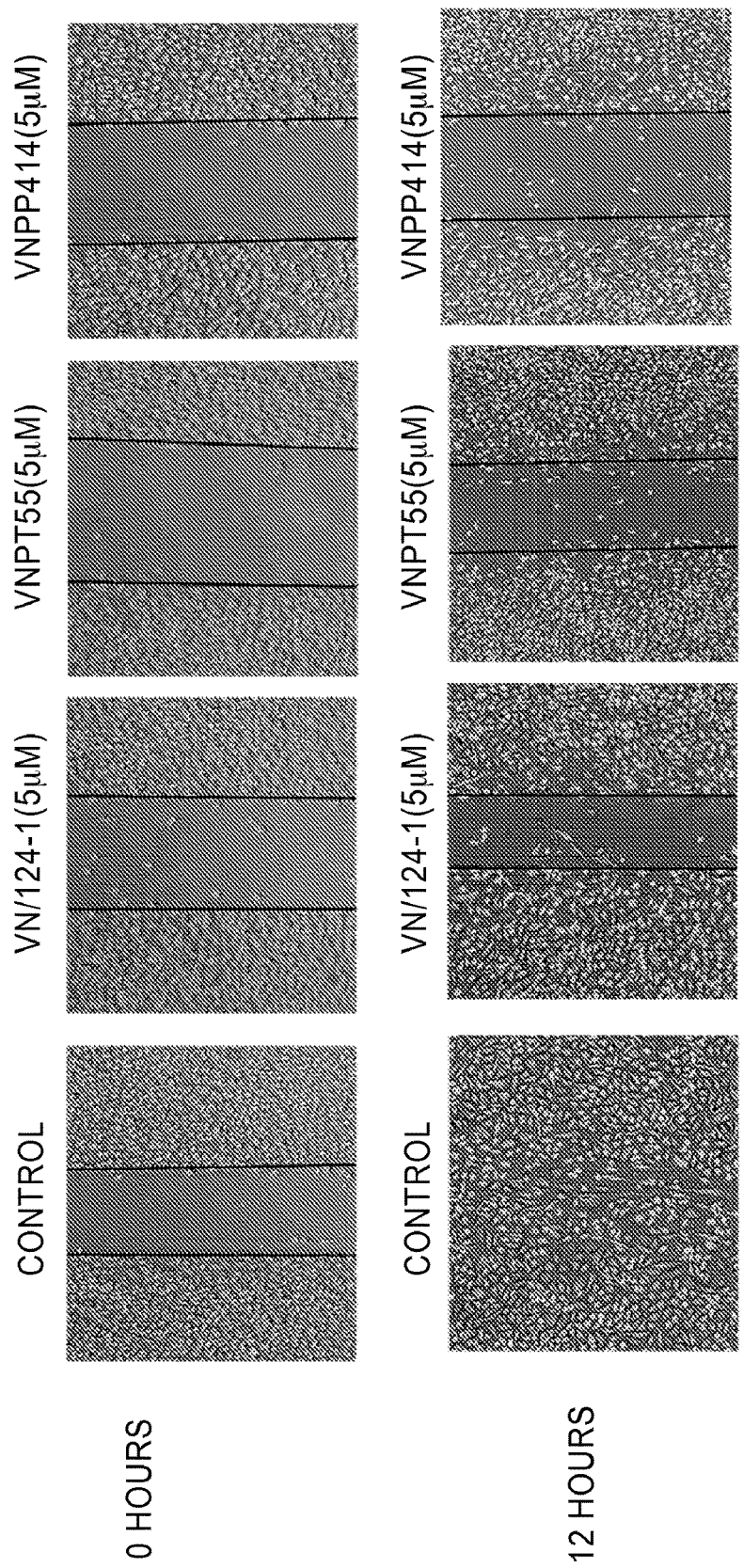
FIG. 10  Effects of VN/124-1 and analogs on cell migration

FIG. 12 Mechanisms of VN/124-1-Induced AR Degradation In Prostate Cancer Cells

Therapeutic Approached to Block Androgen Receptor (AR) Transactivation

EPI-001 interacts with AR NTD to block AR transcriptional activity. Inhibitors of the LBD include Androgen abliation and antiandrogens. AR degradation may provide optimal blockade of AR activation Diagram of Androgen Receptor Protein N-terminus Domain      Ligand-Binding Domain

NONSTEROIDAL AND STEROIDAL COMPOUNDS WITH POTENT ANDROGEN RECEPTOR DOWN-REGULATION AND ANTI PROSTATE CANCER ACTIVITY

CROSS REFERENCE

This application claims benefit of U.S. Provisional Application No. 61/808,345, filed on Apr. 4, 2013, and U.S. Provisional Application No. 61/808,902, filed on Apr. 5, 2013, both which are herein incorporated by reference.

STATEMENT OF FEDERALLY SPONSORED RESEARCH

This invention was made with government support under grant number CA129379 awarded by the National Institutes of Health. The government has certain rights in the invention.

BACKGROUND OF THE INVENTION

Prostate cancer (PC) is the most common tumor in men in western countries, and the second cause of cancer-related death among them. Almost 80% of cases are diagnosed as localized disease, and radiation or surgery can be curative. However, despite current treatment options, there is still a relapse rate of 30-60%.

Applicant has designed and synthesized of novel non-steroid and steroid-mimetic compounds that cause down-regulation of the androgen receptor (AR), both full length and splice variant, induce apoptosis and inhibit proliferation of both androgen sensitive and castration resistant human prostate cancer cells. These steroid compounds and non-steroid compounds may be agents for the prevention and/or treatment of all forms of prostate cancer and all other diseases that depend on functional AR.

AR is a well established target for therapeutic intervention in prostate cancer.

Other androgen receptor associated conditions that may be prevented and/or treated in the present invention include bladder cancer, pancreatic cancer, hepatocellular carcinoma, benign prostatic hyperplasia (BPH) and Kennedy's disease.

Androgen and androgen receptor (AR) play crucial role in the development and advancement of PC. As a consequence, for locally advanced or metastatic disease, hormonal treatment with androgen deprivation therapy, which blocks the production (CYP17 inhibitors: Abiraterone; 1) and/or activity of androgen (anti-androgens, Bicalutamide; 2), is a standard approach for the majority of patients (Chart 1), but most cases the duration of response is limited to 12-24 months, and the disease will become castration-resistant (CRPC) with no treatment options. Approximately 85% of CRPC patients succumb within 5 years and docetaxel (3) is currently the only treatment shown to provide even minimal survival benefit.

In castration-resistant environment aberrant AR reactivation is implicated through numerous mechanisms which leads to over expression of mutated AR, AR amplification and local androgen synthesis.[5] Recently, multiple alternative spliced AR isoforms (AR-Vs) have been identified in CRPC. Unlike full-length AR (fAR) these AR-Vs are lack of the hormone-binding domain and also their activities are independent of hormone. The AR-Vs are expressed at higher level in various tumors and are three to five times more potent than fAR in transactivating activity. Patients expressing constitutively active AR-Vs will in the long-term prob- ably not benefit from antiandrogen and therapies aiming to reduce androgen synthesis. In fact, 'not all CRPC patients do however respond to novel antiandrogen (MDV3100; 4) and CYP17 inhibitors (1), and even those who do subsequently relapse within a few months'. Based on above findings it is envisioned that effective treatment of CRPC patients will require new drugs that can modulate all forms of AR such as AR down-regulating (ARD) agents (ARDAs). The substantial anti-PC efficacy of Phase II clinical candidate 'Galeterone' (VN/124-1, 5, Chart 1 below) in comparison to abiraterone is by virtue of its multi target mechanism of action (CYP-17 inhibition, antiandrogen and ARD activity). (http://clinicaltrials.gov/ct2/show/NCT01709734).

For the development of ARD agents Applicant recently systematically explored the structure of 5 (VN/124-1). In which chemical functions atC17, C16 and C3 of Galeterone modified while androstene scaffold unaltered. The C17 bezimidazole (BzIm) ring in Galeterone is essential to block catalytic 17α-hydroxylation of pregnenolone and progesterone mediated by CYP17 enzyme to obtain bio-precursors of androgen biosynthesis. Where 3β-OH group forms single direct hydrogen bond between inhibitor and polar amino acid residue of CYP17 enzyme. Similarly 3β-OH or 3-keto group of natural and synthetic hormones are identical of the interactions that are conserved in the androgen, estrogen, glucocorticoid, mineralocorticoid and progesterone receptors. Therefore, H-bonding interaction of 3β-OH and keto group of synthetic and natural hormones are critical for ligand recognition by CYP17 and hormone receptors. The 3β-OH group in galeterone is responsible for potent CYP17 and antiandrogen activity. This is further supported by loss of antiandrogen and CYP17 inhibitory activity of galeterone on modification of its C3 substitution with imidazole carabamate (VNPT55 (6)) and pyridine carboxylate (VNPT178 (7)) group. This modifications also enhanced ARD by 8.25-fold against fAR, 4-fold against AR-Vs and 4-fold increase in anti-PC activity. Applicant has successfully discovered and reported first rather selective (Chart 2) AR down-regulating agents (both fAR and AR-Vs).

Chart 1: Chemical Structure of Compounds 1-5 (Clinical Anti PC Agents).

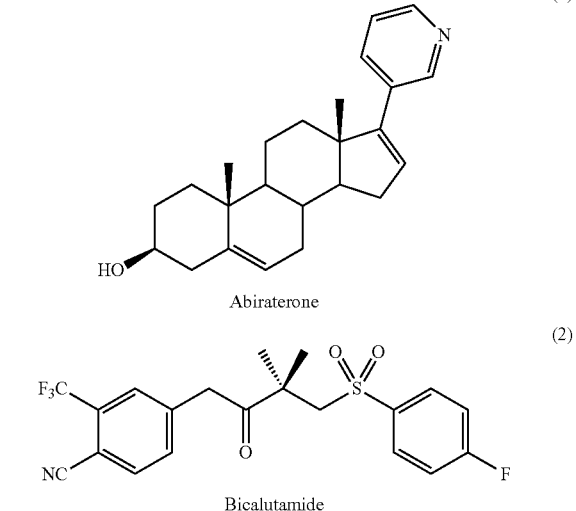

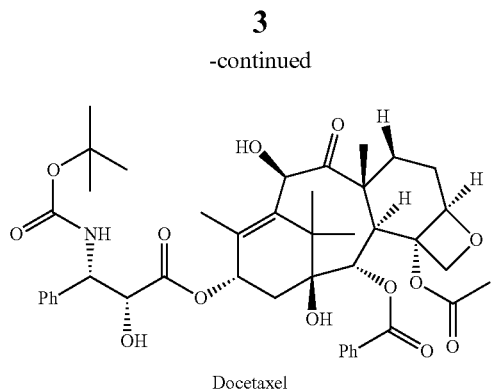
Docetaxel

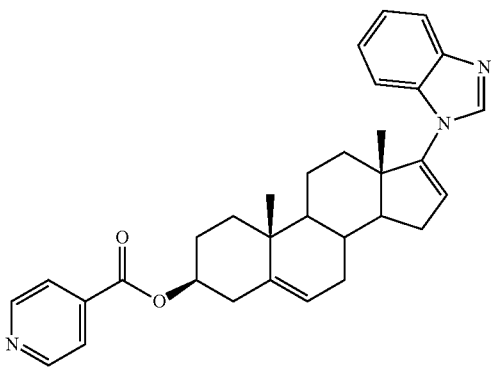
VNPT178

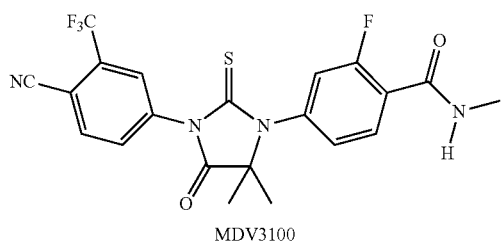
MDV3100

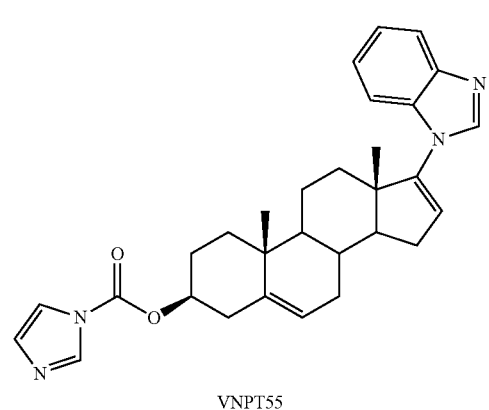
VN/124-1

Chart 2: Chemical Structure of Selective ARD Agents

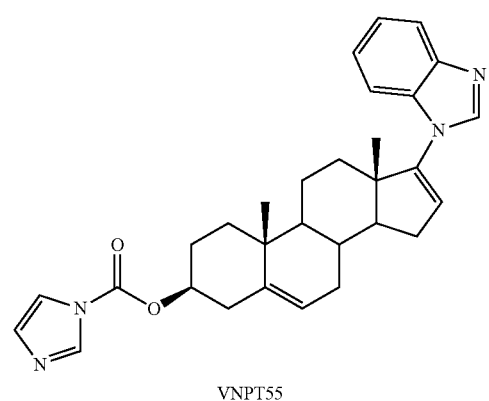
VNPT55

BRIEF SUMMARY OF THE INVENTION

Considering the of AR modulating strategy (AR down-regulation/degradation) in the treatment of prostate cancer disease at present Applicant has designed, synthesized and tested several novel nonsteroidal and steroidal small molecules as antiprostate cancer agents. A preliminary account of part of this work has recently been reported.[21] The advantages may include improved physiochemical & pharmacokinetic properties, increased selectivity of biological activity and, as drug resistance remain a major problem in cancer therapy, the variety of well-tolerated ARDAs with differing chemical structures offer the possibility that several useful drugs will be available.

For the design of novel nonsteroidal agents Applicant has replaced androstene core with some reported steroidal surrogates such as biphenyl,[22, 23] naphthalene,[22] stilbene,[24] tetrahydroisoquinoline and designed diaryl compound with alkylamine, amide and sulfonamide linkers core structure.[25] On all these scaffolds head group (BzIm) is held constant while tail is hydroxyl or masked with methyl or replaced with carboxylic/nitrile/imidazole/tetrazole etc groups in combination. Similarly for steroidal agents Applicant chose androstene and estrogen structure as scaffolds in which bezimidazole as head and various function such as acid, ester, imidazole, ethers carbamates etc functions as tail.

Biological Activity

Concept of AR Down-Regulation as a Therapeutic Strategy

Current treatments are centered on blocking androgen-signaling axis, but the emergence of castration resistant PC (CRCP) prevails. Such resistant PC tumors continue to grow in the presence of low circulating endogenous ligands by virtue of the presence of active and functional AR. Applicant has developed novel AR down-regulating agents (ARDAs) to treat and/or prevent cancer.

Previously Applicant discovered few ARDAs (synthetic small molecules) through HipHop Pharmacophore modeling.[1]

Applicant has developed new steroidal derivatives as potent ARDA via lead optimization of our PC drug candidate, VN/124-1 (Galeterone; FIG. 1), currently in phase II clinical trials.[2]

The instant invention includes novel nonsteroidal compounds and novel steroid compounds as ARDAs.

The instant invention includes a method of treating prostate cancer comprising administering an effective amount of the compounds of the instant invention.

The instant invention includes a method of treating castration resistant prostate cancer.

The instant invention includes degrading a full length or a splice variant by administering an effective amount of the compounds of the instant invention.

The instant invention includes a method of inhibiting proliferation of androgen sensitive cells by administering an effective amount of the compounds of the instant invention.

The compounds may be used for treatment individually or with one or more compounds of the instant invention. The compounds may also be used for treatment with other known compounds or treatment methods.

C-17 Benzimidazole (BzIm) is essential and optimal for observed androgen receptor down-regulating (ARD) activity. Replacement of 3β-OH with imidazolecarbamate (FIG. 1) resulted in potent and specific ARD activity. The steroidal molecular frame of VN/124-1 was not altered in previous study.

Although side effects for VN/124-1 due to its steroidal scaffold have not been observed in the clinic thus far, the potential side effects of steroidal drugs believed to be due to binding to various steroid receptors to elicit agonistic or antagonistic effects may be a matter of concern.

In the last two decades several reports have focused on diverse chemical scaffolds such as biphenyl, naphthylene, and stibene, as excellent surrogates for the steroidal scaffold in the breast and prostate cancers drug discovery and development fields.

The present invention includes possible modification of steroidal scaffold while retaining C-17 BzIm group and retaining or replacing C-3 hydroxyl group with hydrophilic moieties, including $OCH_3$, COOH, CN, and 1H-tetrazole groups.

Agents discovered by Applicant include selected biphenyl, naphthylbipheyl and stilbene scaffolds (FIG. 2). Applicant's invention includes Flexible alignment experiment using (MOE) for nonsteroidal scaffolds to find out how well hydrophilic and hydrophobic functions on new scaffolds superimposed with VN/124-1 (FIG. 3). In addition, the estrone derivatives were designed as alternative of the androstane core of our earlier compounds.

DESCRIPTION OF THE DRAWINGS

FIG. 9A-H. Effects of compounds on oncogenes.
FIG. 10. Effects of VN124-1 and analogs on cell migration.

DETAIL DESCRIPTION OF THE INVENTION

Synthesis

Figure 1:
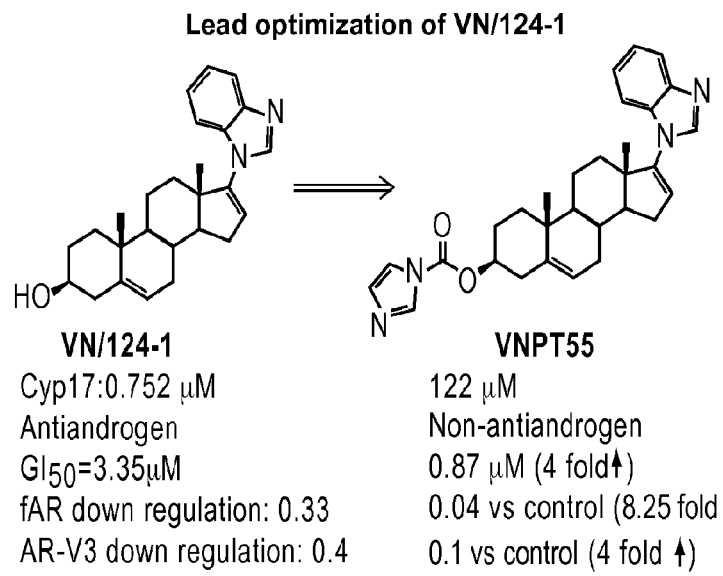
FIG. 1. Lead optimization of VN/124-1.
Figure 2:
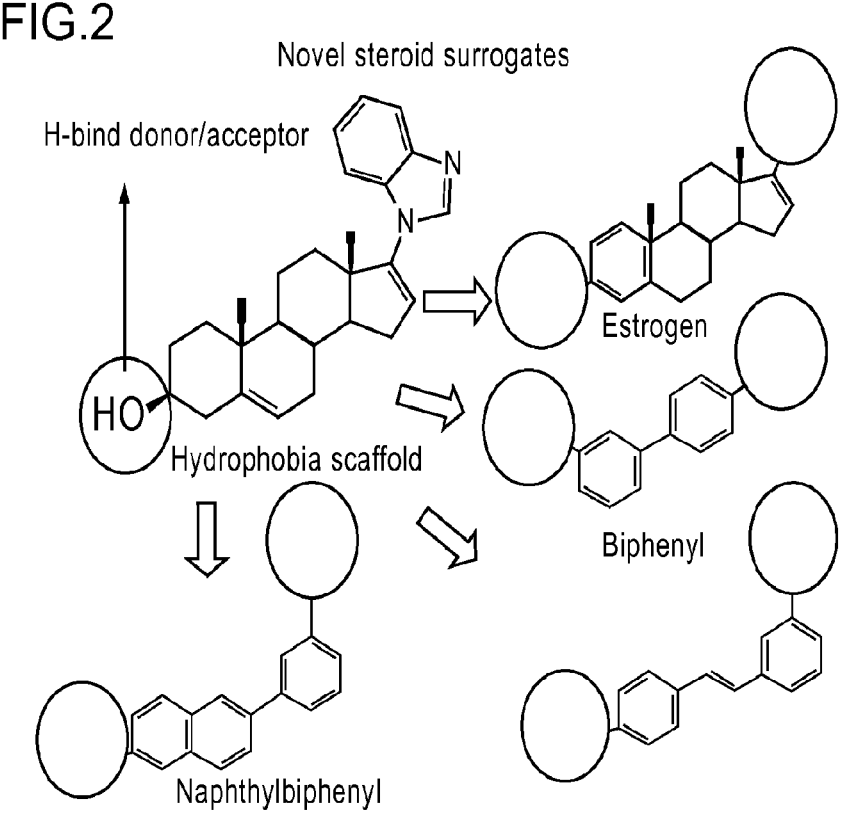
FIG. 2. Novel steroid surrogates.
Figure 3:
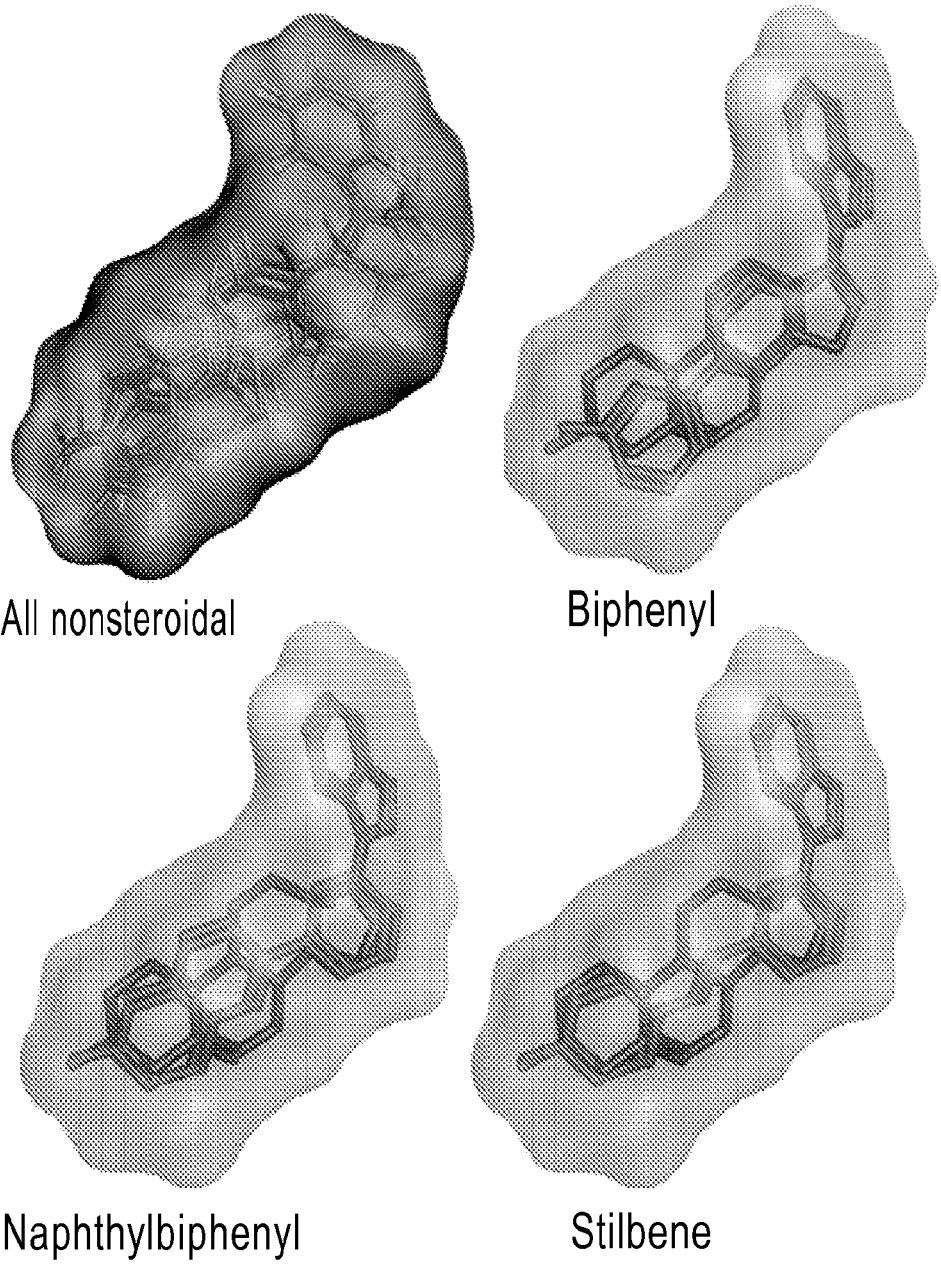
FIG. 3. Flexible alignment with VN/124-1.

Synthetic methods of molecules in this study are depicted in the Schemes below. The key intermediates, alkylated-BzIm's (1a, 2a) synthesized by following reported KOH in DMSO method, while arylated-BzIm (11a) by reported method of ligated-catalysis' Ullmann condensation reaction. Suzuki coupling of bromoalkyl/aryl-BzIm with corresponding boronic acid resulted in biphenyls (1-8, 11). Conversion of nitrile-biphenyls (3, 4) to 1H-tetrazoles (9, 10) was achieved by 1,3-dipolar addition of sodium azide in presence of ammonium chloride in DMF. Styrenes (12a,13a) were obtained by witting method[10] subjected to Mizoroki-Heck reaction to get desired (E)-stilbenes (12, 13). For estrone-3-carboxylate (16), 3-enol carbon was activated by triflate followed by replacement with carboxylate through pd catalyzed reaction. BzIm substitution on estrone C-17 via Vilsmeir reaction achieved following our routine method for the synthesis of C-17 BzIm substituted steroid compounds. The 17-pyridyl estrone derivative synthesized following reported procedure.[13]

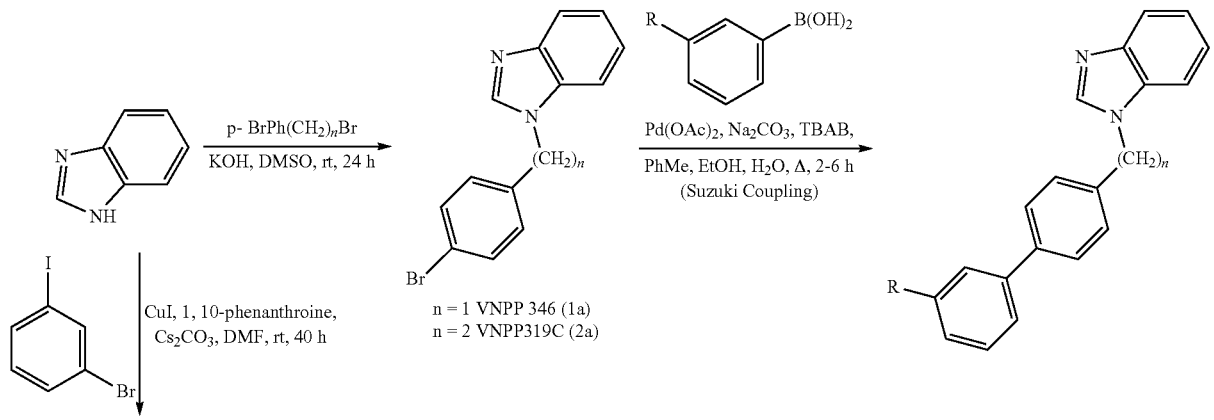

Schme 1: Synthesis of biphenyl and naphthylbiphenyl derivatives

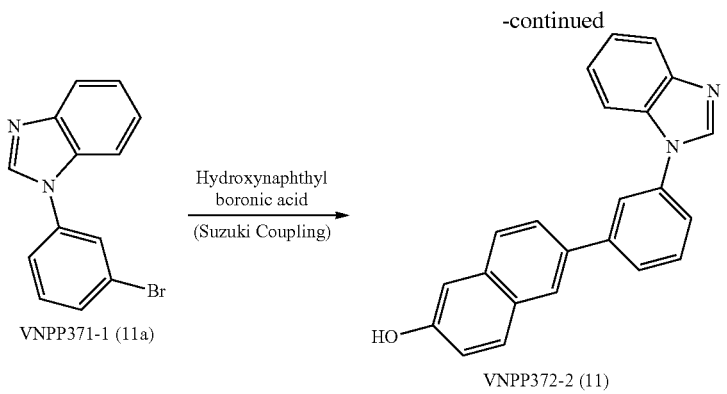
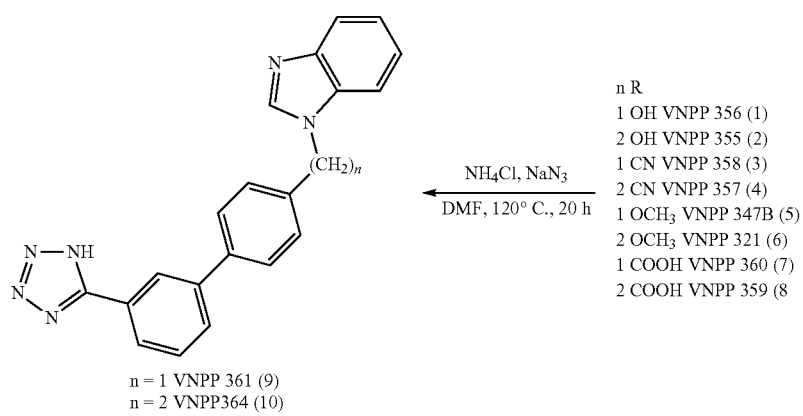
Scheme 2: Synthesis of stibene derivatives
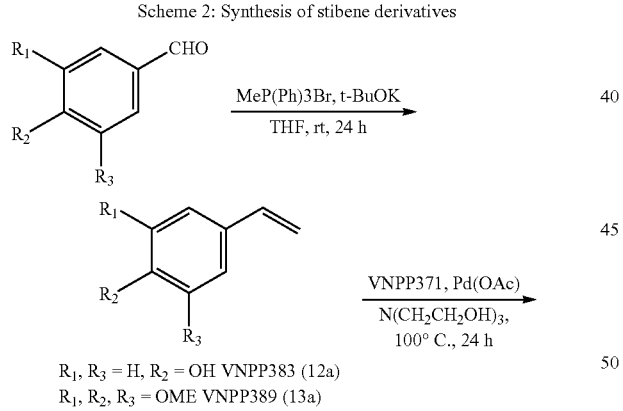
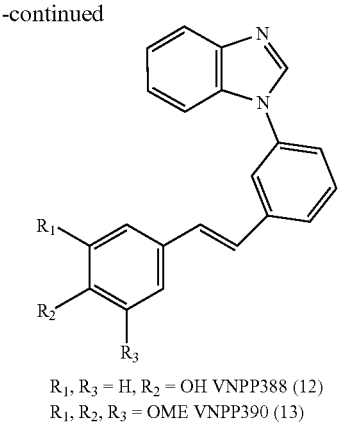
Scheme 3: Synthesis of estrone-3-hydroxy and 3-carboxy derivatives
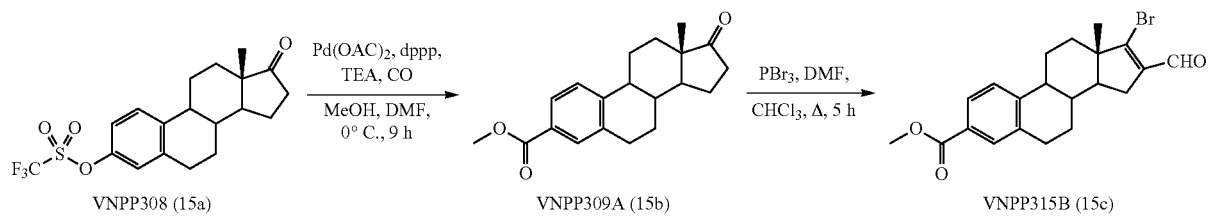

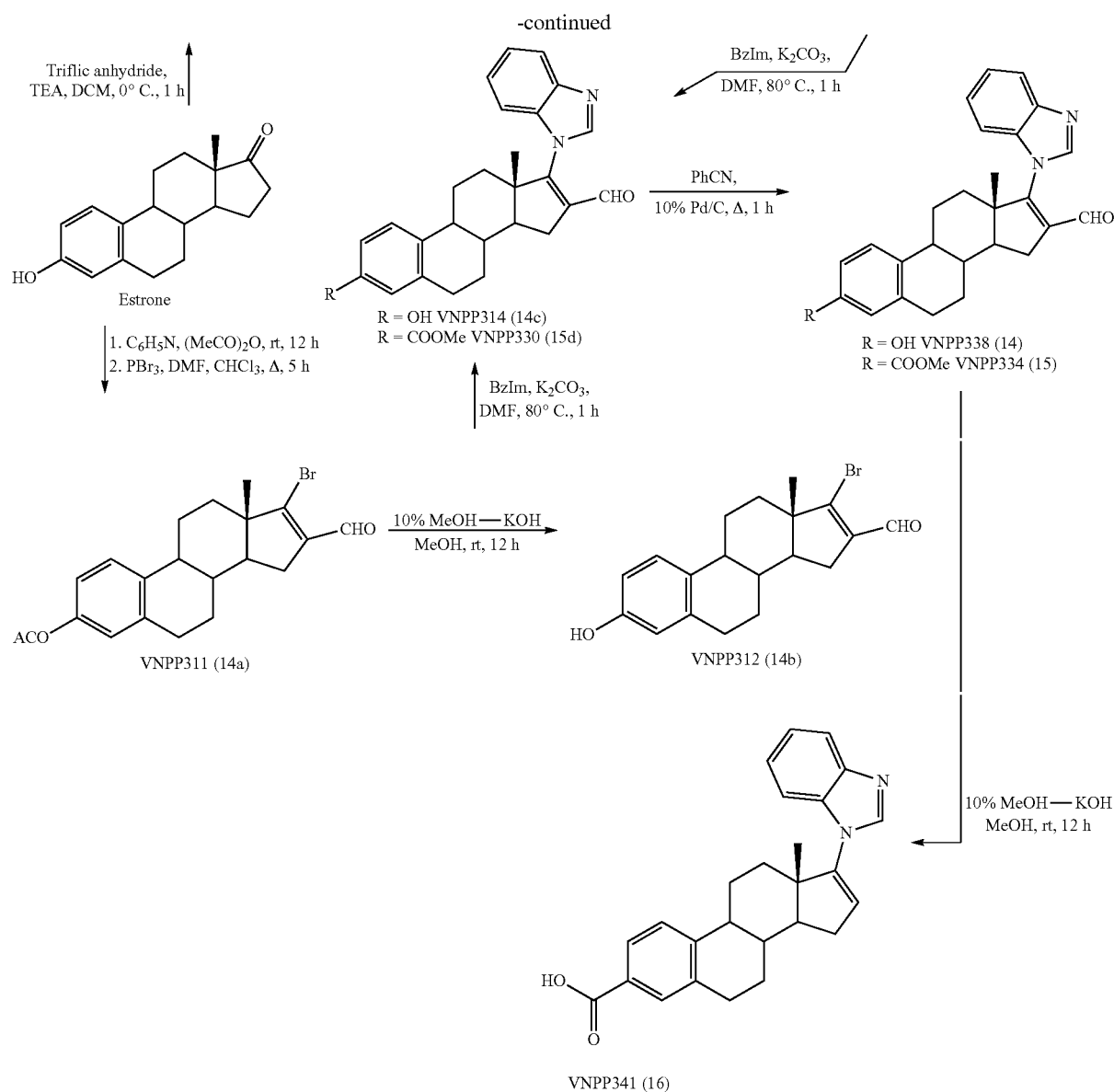
Scheme 4: Synthesis of estrone-3-hydroxy-17-pyridyl derivative
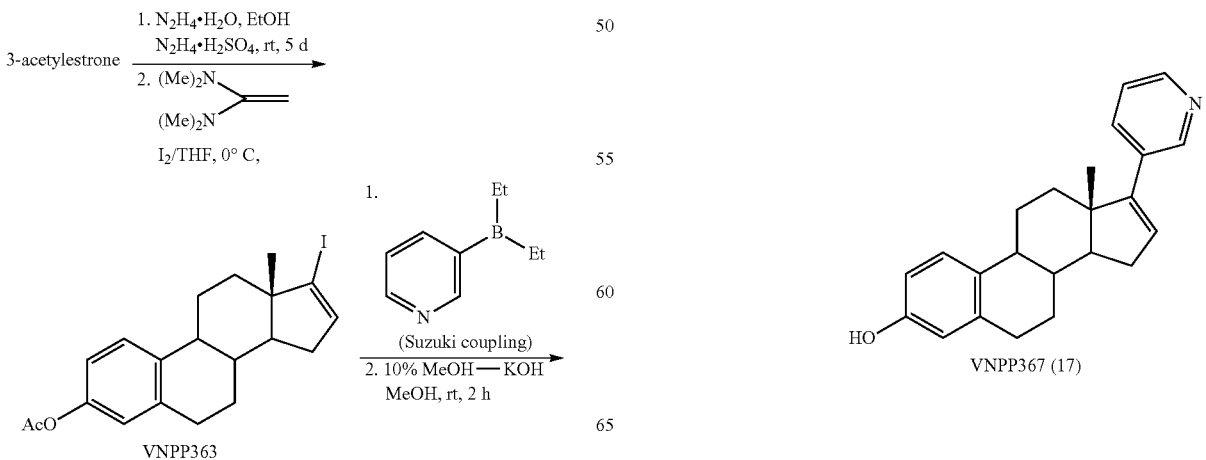

See also the schemes below.
Novel Nonsteroids for Cancer Treatment:
Biphenyl Derivatives (B Series)

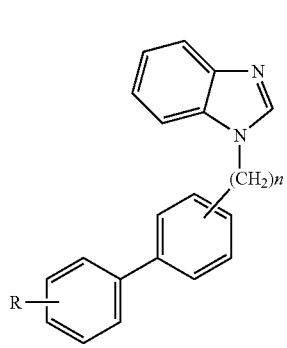
B wherein R represents mono or di substitutions selected from the group consisting of —OH, —NH₂, —NHR', —N(R')₂—, —SH, —OMe, —CN, —COON, —COOMe, —COOEt, imidazole, 1H-tetrazole and their combinations, wherein each R' is independently selected from alkyl or aryl.
Examples of B series
n=0 or 1 or 2

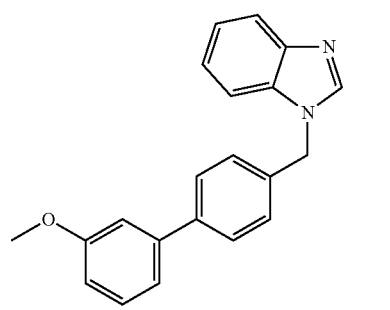
VNPP347B (B1)

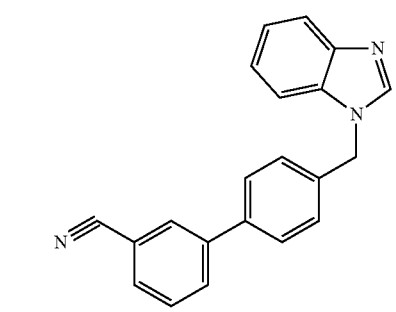
VNPP358 (B2)

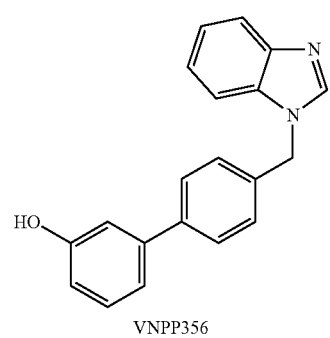
VNPP356 (B3)

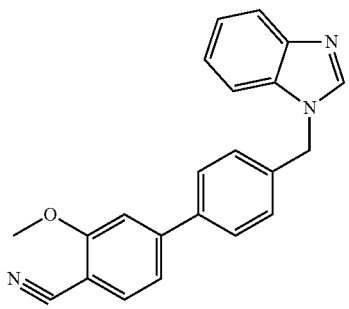
B4

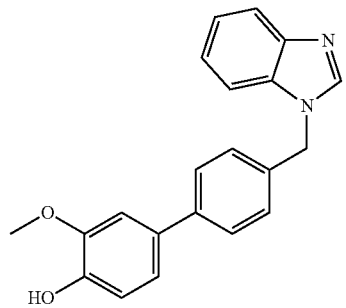
B5

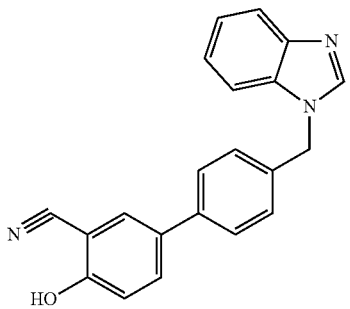
B6

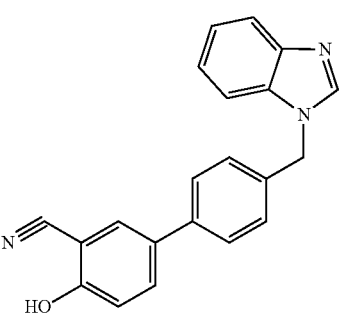
VNPP360 (B7)

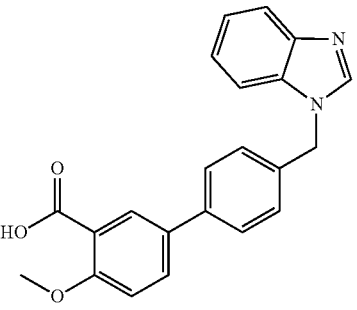
B8

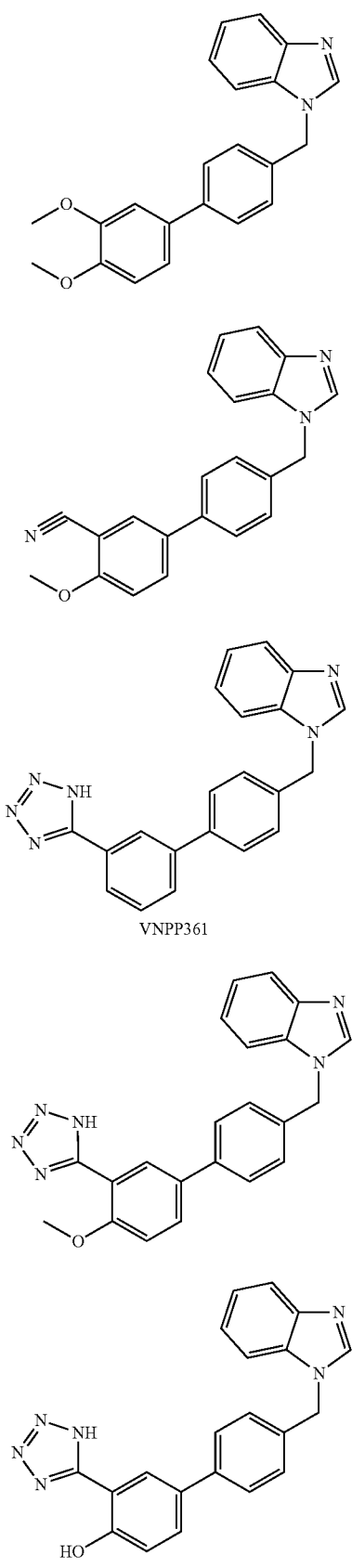
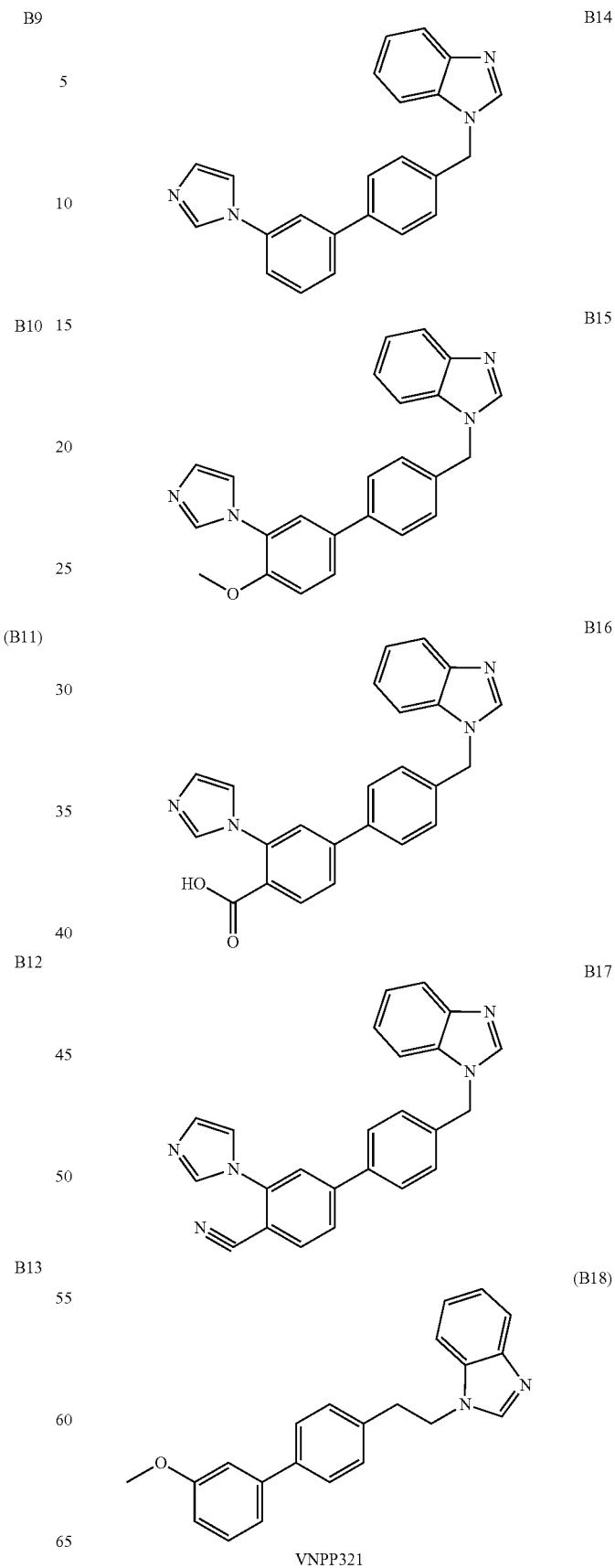

-continued

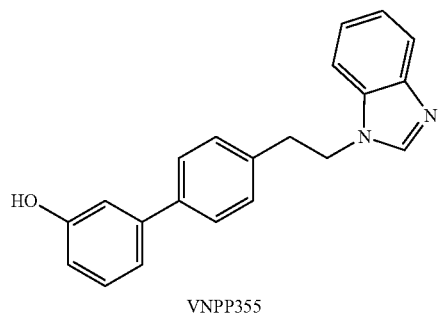
(B19)
VNPP355

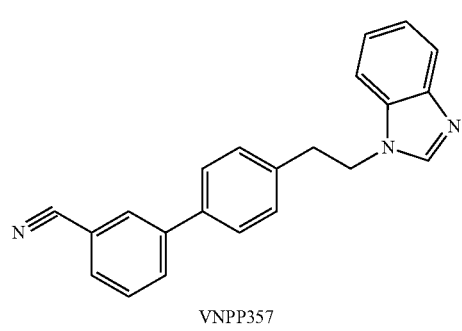
(B20)
VNPP357

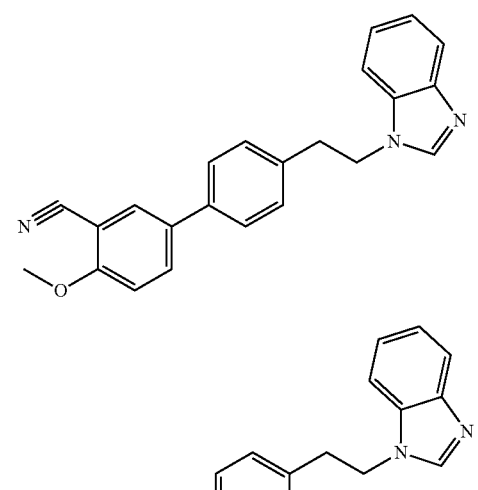
B21

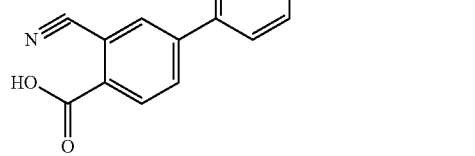
B22

-continued

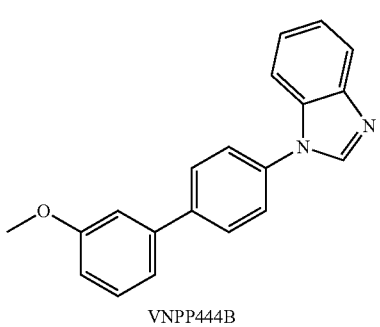
(B23)
VNPP444B

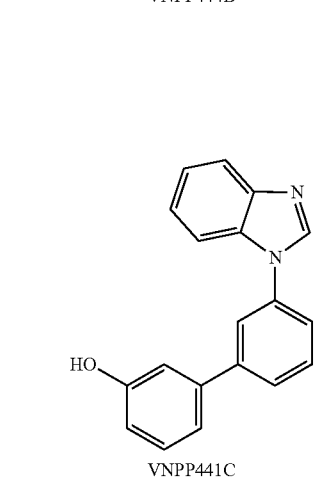
(B24)
VNPP441C

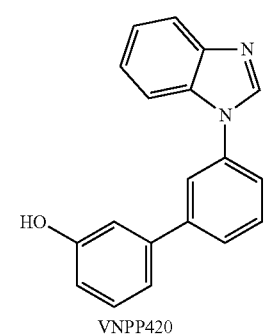
(B25)
VNPP420

TABLE 1

| Biphenyl derivatives (B series) | |
|---|---|
| VNPP347 (B1) | 3-[4-(benzimidazolylmethyl)phenyl]-1-methoxybenzene |
| VNPP358 (B2) | 3-[4-(benzimidazolylmethyl)phenyl]benzenecarbonitrile |
| VNPP356(B3) | 3-[4-(benzimidazolylmethyl)phenyl]phenol |
| B4 | 4-[4-(benzimidazolylmethyl)phenyl]-2-methoxybenzenecarbonitrile |
| B5 | 4-[4-(benzimidazolylmethyl)phenyl]-2-methoxyphenol |
| B6 | 5-[4-(benzimidazolylmethyl)phenyl]-2-hydroxybenzenecarbonitrile |
| VNPP360 (B7) | 3-[4-(benzimidazolylmethyl)phenyl]benzoic acid |
| B8 | 5-[4-(benzimidazolylmethyl)phenyl]-2-methoxybenzoic acid |
| B9 | 4-[4-(benzimidazolylmethyl)phenyl]-1,2-dimethoxybenzene |
| B10 | 5-[4-(benzimidazolylmethyl)phenyl]-2-methoxybenzenecarbonitrile |
| VNPP361 (B11) | 5-{3-[4-(benzimidazolylmethyl)phenyl]phenyl}-1H-1,2,3,4-tetraazole |

TABLE 1-continued

| | Biphenyl derivatives (B series) |
|---|---|
| B12 | 2-(1H-1,2,3,4-tetraazol-5-yl)-4-[4-(benzimidazolylmethyl)phenyl]-1-methoxybenzene |
| B13 | 2-(1H-1,2,3,4-tetraazol-5-yl)-4-[4-(benzimidazolylmethyl)phenyl]phenol |
| B14 | {[4-(3-imidazolylphenyl)phenyl]methyl}benzimidazole |
| B15 | 4-[4-(benzimidazolylmethyl)phenyl]-2-imidazolyl-1-methoxybenzene |
| B16 | 4-[4-(benzimidazolylmethyl)phenyl]-2-imidazolylbenzoic acid |
| B17 | 4-[4-(benzimidazolylmethyl)phenyl]-2-imidazolylbenzenecarbonitrile |
| VNPP321 (B18) | 3-[4-(2-benzimidazolylethyl)phenyl]-1-methoxybenzene |
| VNPP355(B19) | 3-[4-(2-benzimidazolylethyl)phenyl]phenol |
| VNPP357 (B20) | 3-[4-(2-benzimidazolylethyl)phenyl]benzenecarbonitrile |
| B21 | 5-[4-(2-benzimidazolylethyl)phenyl]-2-methoxybenzenecarbonitrile |
| B22 | 4-[4-(2-benzimidazolylethyl)phenyl]-2-cyanobenzoic acid |
| VNPP444B(B23) | 1-(3'-methoxy-[1,1'-biphenyl]-4-yl)-1H-benzo[d]imidazole |
| VNPP441C(B24) | 1-(3'-hydroxy-[1,1'-biphenyl]-3-yl)-1H-benzo[d]imidazole |
| VNPP420 (B25) | 1-(3'-methoxy-[1,1'-biphenyl]-3-yl)-1H-benzo[d]imidazole |
| VNPP359 | 4'-(2-(1H-benzo[d]imidazol-1-yl)ethyl)-[1,1'-biphenyl]-3-carboxilic acid |
| VNPP364 | 1-(2-(3'-(1H-tetrazol-5-yl)-[1,1'-biphenyl]-4-yl)ethyl)-1H-benzo[d]imidazole |

Naphthalene Derivatives (Na Series)

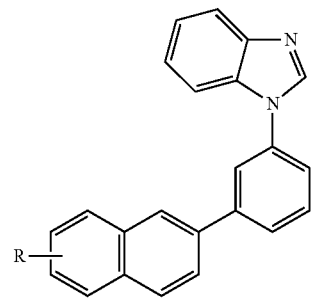

Na wherein R represents mono or di substitutions selected from the group consisting of —OH, —NH$_2$, —NHR', —SH, —OMe, —CN, —COON, —COOMe, —COOEt, imidazole, 1H-tetrazole and their combinations, wherein each R' is independently selected from alkyl or aryl.

Examples of Na series

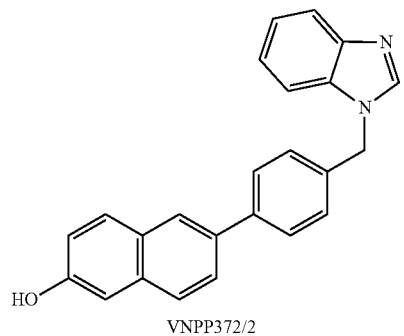

(Na1)

VNPP372/2

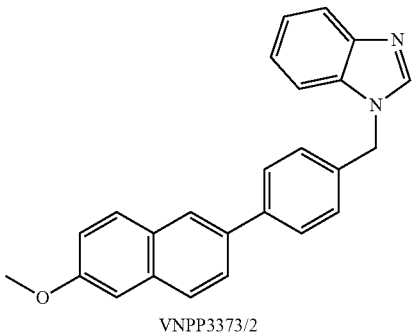

(Na2)

VNPP3373/2

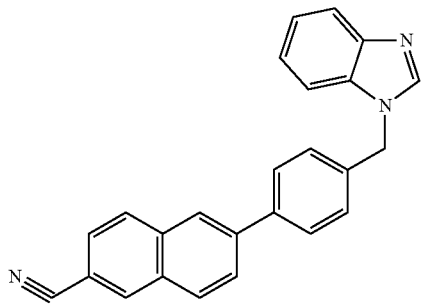

Na3

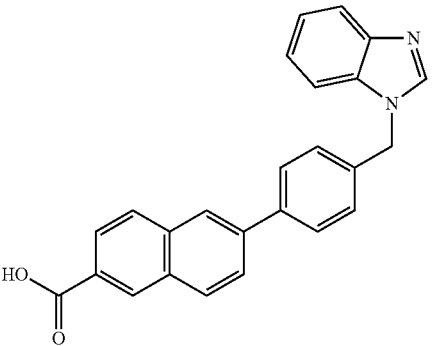

Na4

Na5
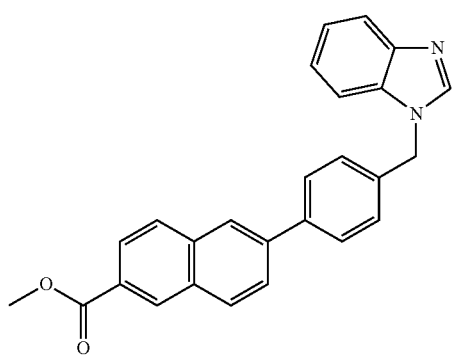
Na6
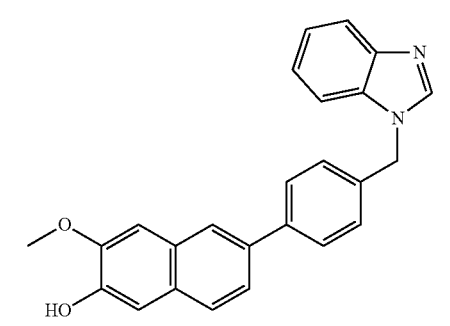
Na7
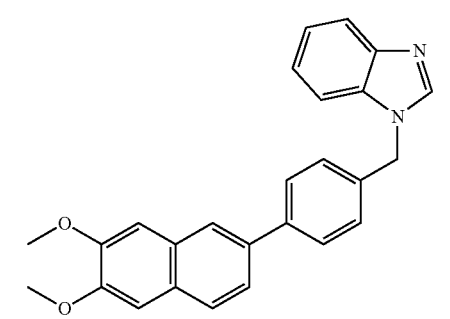
Na8
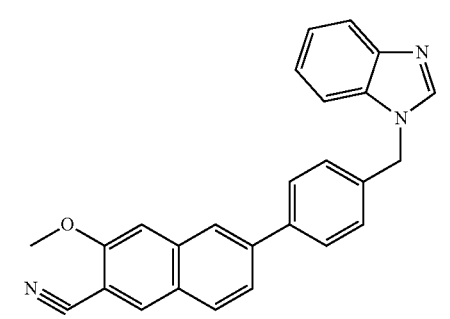
Na9
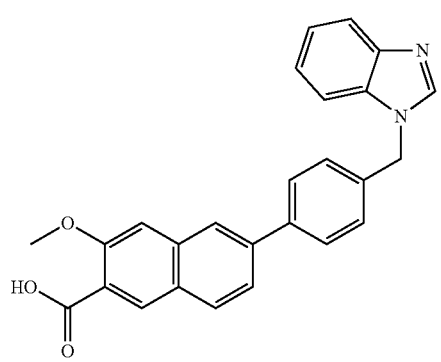
Na10
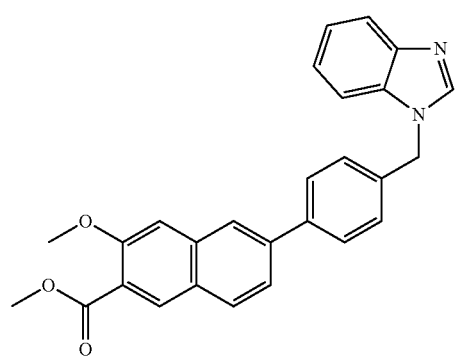
Na11
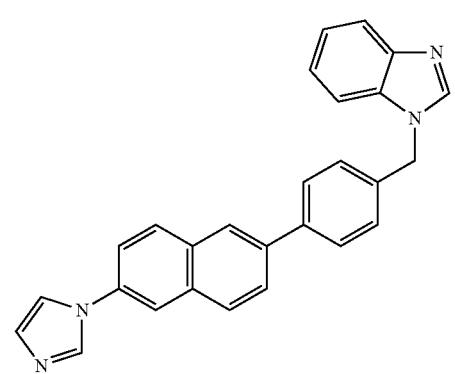
Na12
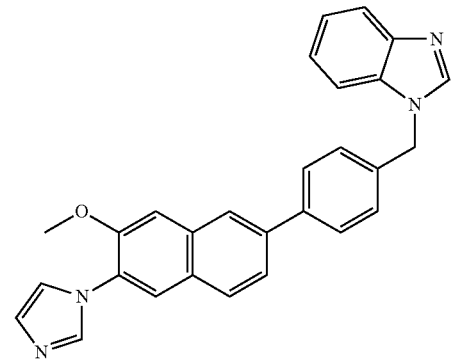

TABLE 2a

Naphthalene derivatives (Na series)

| | |
|---|---|
| VNPP372/2 (Na1) | 6-(3-benzimidazolylphenyl)naphthalen-2-ol |
| VNPP373/2 (Na2) | 6-(3-benzimidazolylphenyl)-2-methoxynaphthalene |
| Na3 | 6-(3-benzimidazolylphenyl)naphthalene-2-carbonitrile |
| Na4 | 6-(3-benzimidazolylphenyl)naphthalene-2-carboxylic acid |
| Na5 | methyl 6-(3-benzimidazolylphenyl)naphthalene-2-carboxylate |
| Na6 | 6-(3-benzimidazolylphenyl)-3-methoxynaphthalen-2-ol |
| Na7 | 6-(3-benzimidazolylphenyl)-2,3-dimethoxynaphthalen |
| Na8 | 6-(3-benzimidazolylphenyl)-3-methoxynaphthalene-2-carbonitrile |
| Na9 | 6-(3-benzimidazolylphenyl)-3-methoxynaphthalene-2-carboxylic acid |
| Na10 | methyl 6-(3-benzimidazolylphenyl)-3-methoxynaphthalene-2-carboxylate |
| Na11 | [3-(6-imidazolyl-2-naphthyl)phenyl]benzimidazole |
| Na12 | 6-(3-benzimidazolylphenyl)-2-imidazolyl-3-methoxynaphthalene |

Naphthalene Derivatives (q Series)

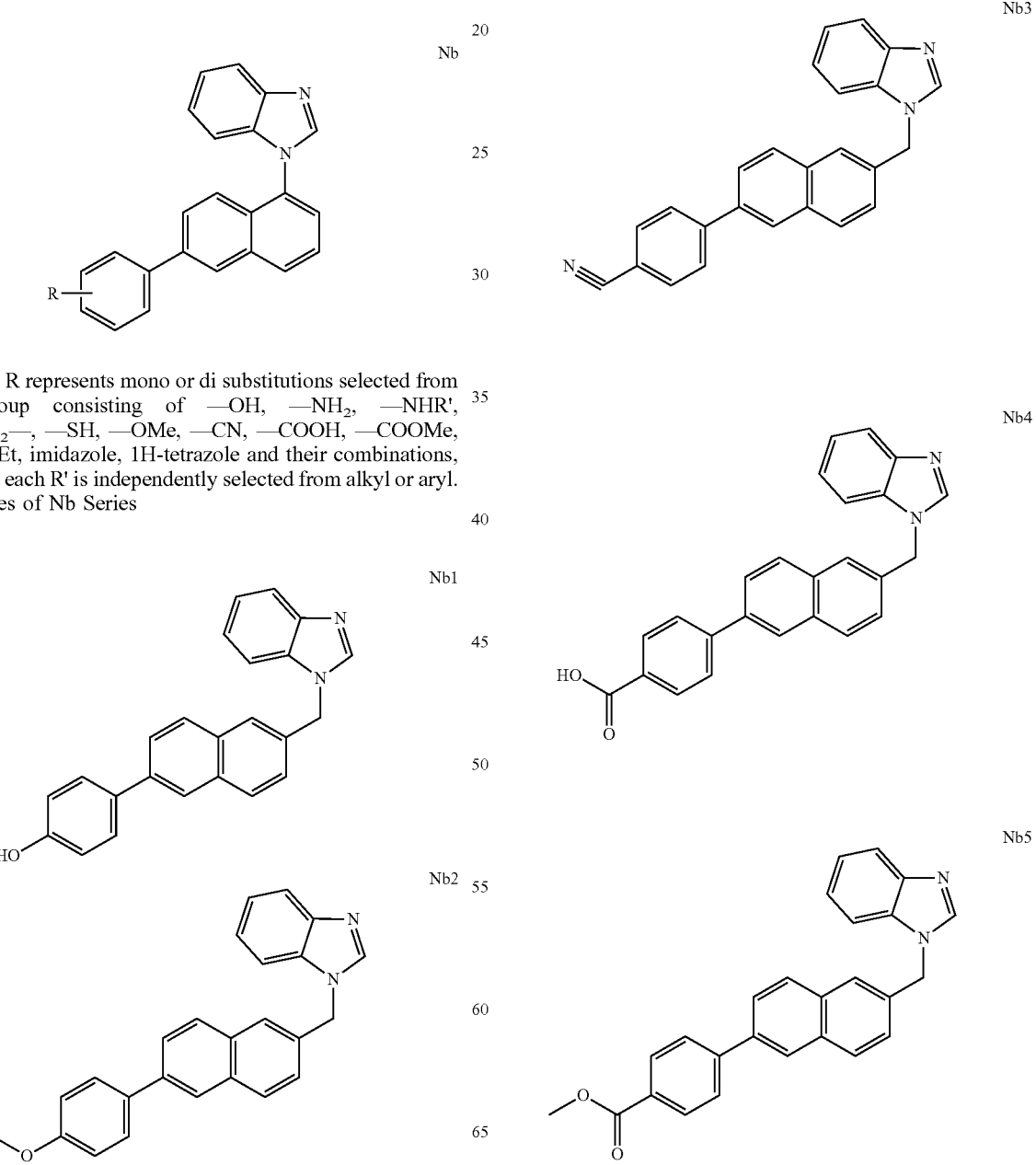

wherein R represents mono or di substitutions selected from the group consisting of —OH, —NH$_2$, —NHR', —N(R')$_2$—, —SH, —OMe, —CN, —COOH, —COOMe, —COOEt, imidazole, 1H-tetrazole and their combinations, wherein each R' is independently selected from alkyl or aryl.
Examples of Nb Series

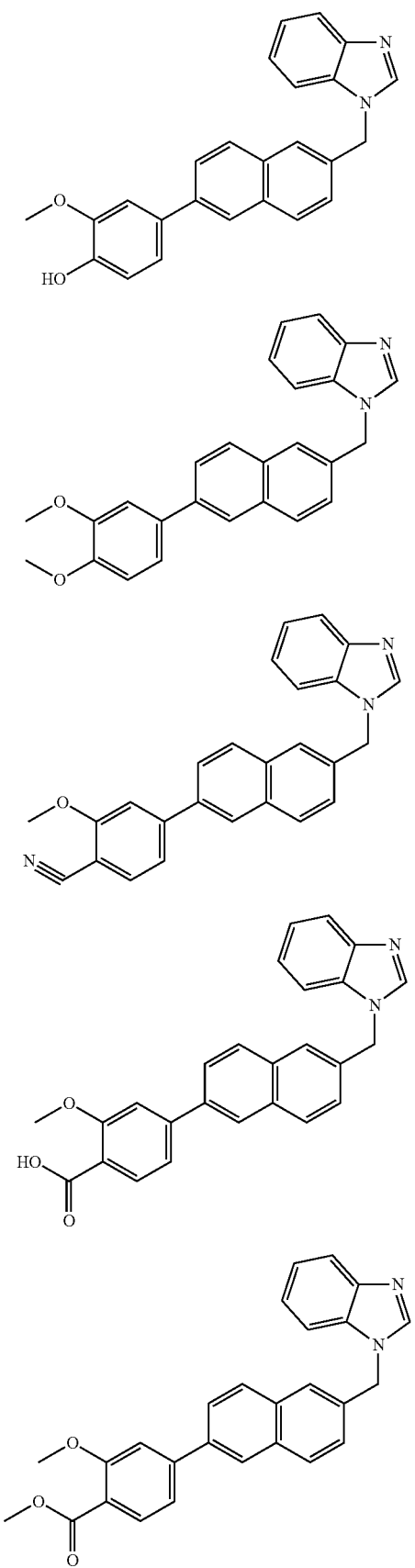
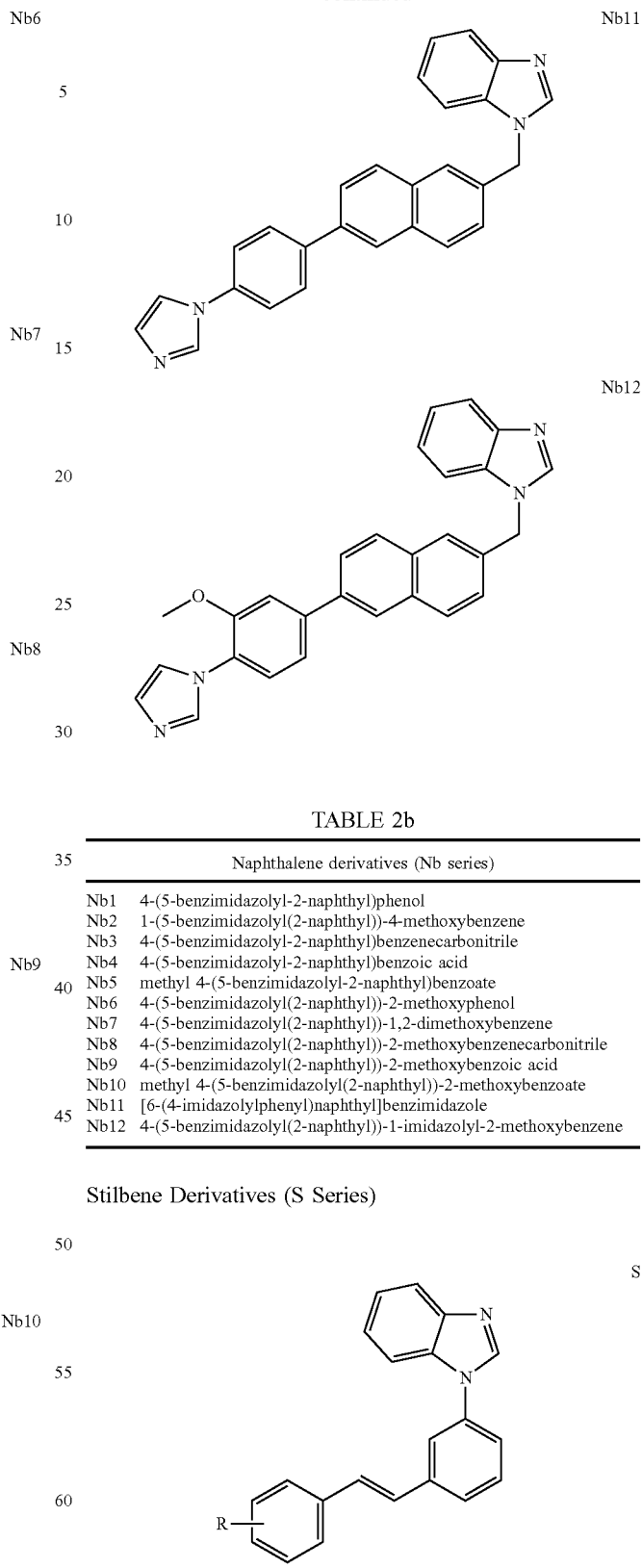

TABLE 2b

Naphthalene derivatives (Nb series)

| | |
|---|---|
| Nb1 | 4-(5-benzimidazolyl-2-naphthyl)phenol |
| Nb2 | 1-(5-benzimidazolyl(2-naphthyl))-4-methoxybenzene |
| Nb3 | 4-(5-benzimidazolyl-2-naphthyl)benzenecarbonitrile |
| Nb4 | 4-(5-benzimidazolyl-2-naphthyl)benzoic acid |
| Nb5 | methyl 4-(5-benzimidazolyl-2-naphthyl)benzoate |
| Nb6 | 4-(5-benzimidazolyl(2-naphthyl))-2-methoxyphenol |
| Nb7 | 4-(5-benzimidazolyl(2-naphthyl))-1,2-dimethoxybenzene |
| Nb8 | 4-(5-benzimidazolyl(2-naphthyl))-2-methoxybenzenecarbonitrile |
| Nb9 | 4-(5-benzimidazolyl(2-naphthyl))-2-methoxybenzoic acid |
| Nb10 | methyl 4-(5-benzimidazolyl(2-naphthyl))-2-methoxybenzoate |
| Nb11 | [6-(4-imidazolylphenyl)naphthyl]benzimidazole |
| Nb12 | 4-(5-benzimidazolyl(2-naphthyl))-1-imidazolyl-2-methoxybenzene |

Stilbene Derivatives (S Series)

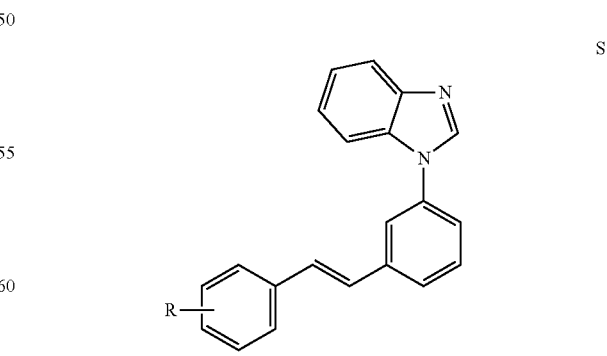

wherein R represents mono or di substitutions selected from the group consisting of —OH, —NH$_2$, —NHR', —N(R')$_2$—, —SH, —OMe, —CN, —COOH, —COOMe, —COOEt, imidazole, 1H-tetrazole and their combinations, wherein each R' is independently selected from alkyl or aryl.
Examples of S Series
(S1)
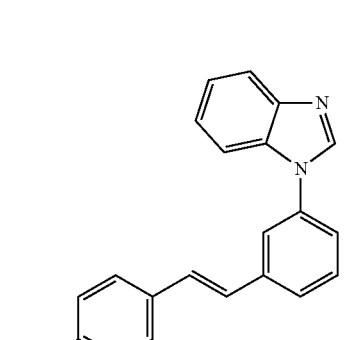
VNPP388
(S2)
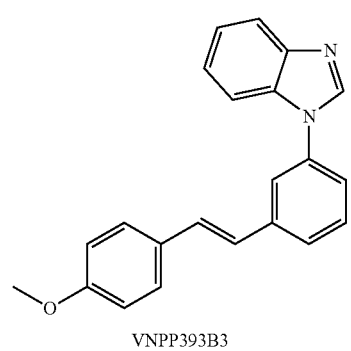
VNPP393B3
S3
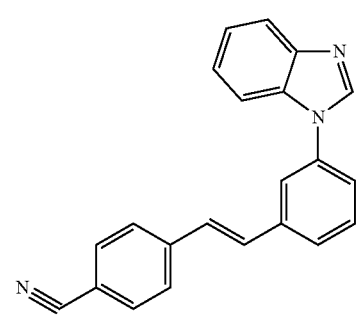
S4
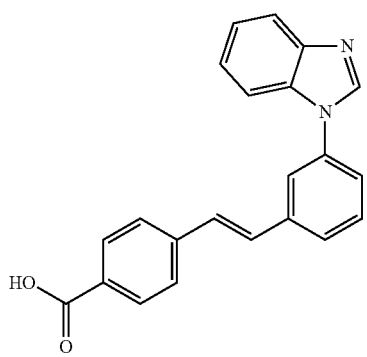
S5
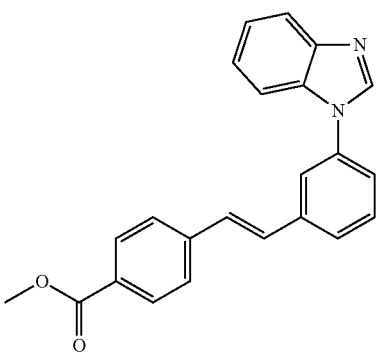
S6
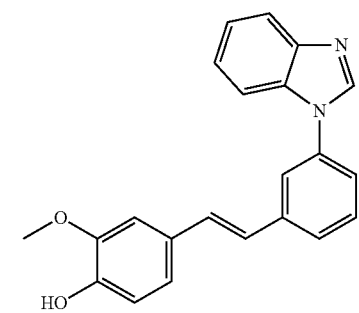
S7
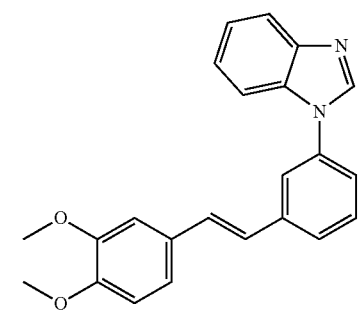
S8
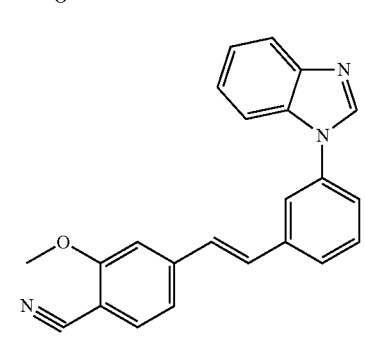
S9
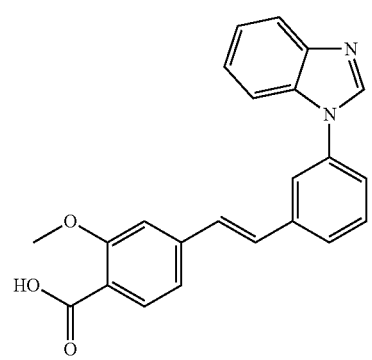

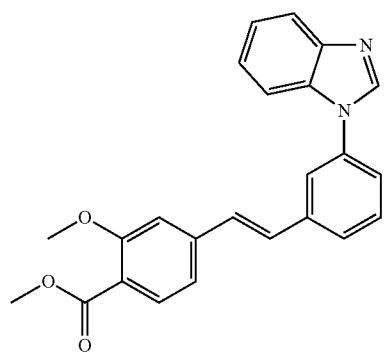
S10

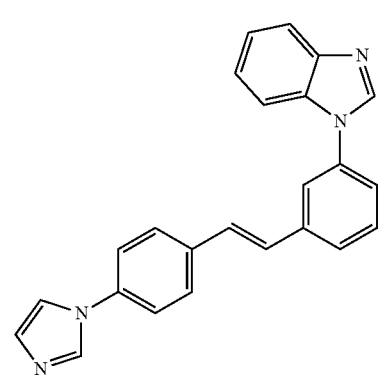
S11

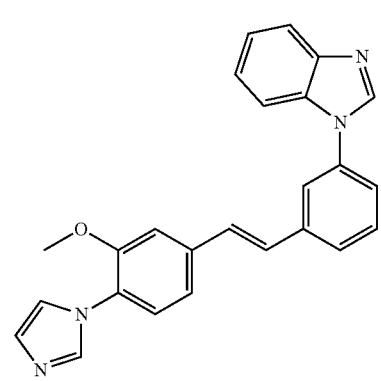
S12

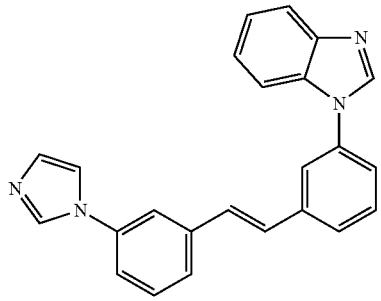
S13

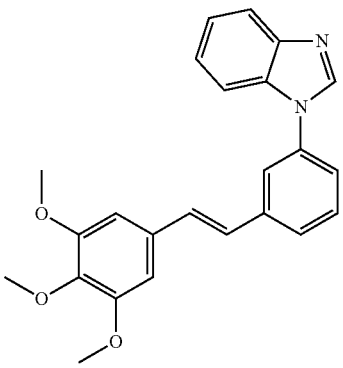
S14

TABLE 3

| Stilbene derivatives (S series) | |
|---|---|
| VNPP388 (S1) | 4-[(1E)-2-(3-benzimidazolylphenyl)vinyl]phenol |
| VNPP391B3 (S2) | 1-[(1E)-2-(3-benzimidazolylphenyl)vinyl]-4-methoxybenzene |
| S3 | 4-[(1E)-2-(3-benzimidazolylphenyl)vinyl]benzenecarbonitrile |
| S4 | 4-[(1E)-2-(3-benzimidazolylphenyl)vinyl]benzoic acid |
| S5 | methyl 4-[(1E)-2-(3-benzimidazolylphenyl)vinyl]benzoate |
| S6 | 4-[(1E)-2-(3-benzimidazolylphenyl)vinyl]-2-methoxyphenol |
| S7 | 4-[(1E)-2-(3-benzimidazolylphenyl)vinyl]-1,2-dimethoxybenzene |
| S8 | 4-[(1E)-2-(3-benzimidazolylphenyl)vinyl]-2-methoxybenzenecarbonitrile |
| S9 | 4-[(1E)-2-(3-benzimidazolylphenyl)vinyl]-2-methoxybenzoic acid |
| S10 | methyl 4-[(1E)-2-(3-benzimidazolylphenyl)vinyl]-2-methoxybenzoate |
| S11 | {3-[(1E)-2-(4-imidazolylphenyl)vinyl]phenyl}benzimidazole |
| S12 | 4-[(1E)-2-(3-benzimidazolylphenyl)vinyl]-1-imidazolyl-2-methoxybenzene |
| S13 | {3-[(1E)-2-(3-imidazolylphenyl)vinyl]phenyl}benzimidazole |
| S14 | 5-[(1E)-2-(3-benzimidazolylphenyl)vinyl]-1,2,3-trimethoxybenzene |

Amide Derivatives (Amd-a Series)
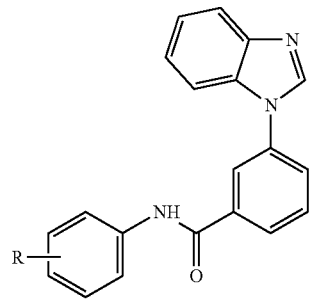
Amd-a
wherein R represents mono or di substitutions selected from the group consisting of —OH, —NH₂, —NHR', —N(R')₂—, —SH, —OMe, —CN, —COOH, —COOMe, —COOEt, imidazole, 1H-tetrazole and their combinations, wherein each R' is independently selected from alkyl or aryl.
Examples of Amd-a Series
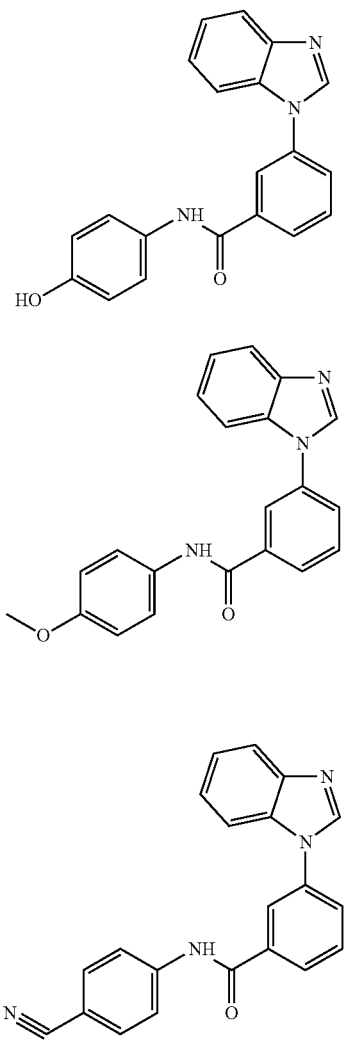
Amd-a1
Amd-a2
Amd-a3
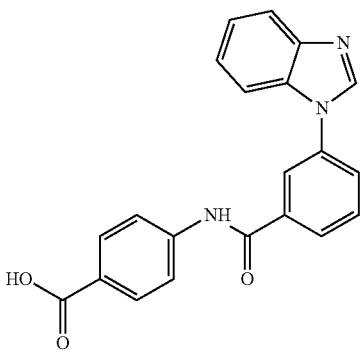
Amd-a4
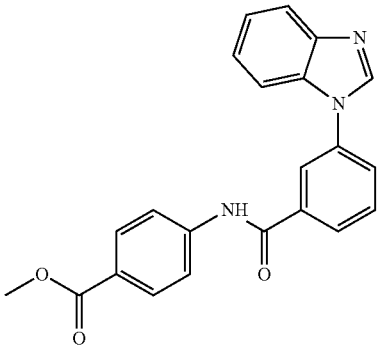
Amd-a5
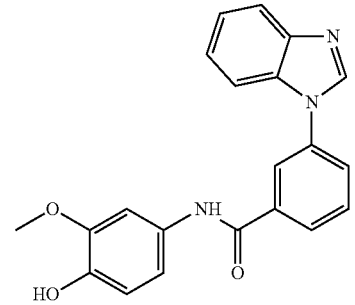
Amd-a6
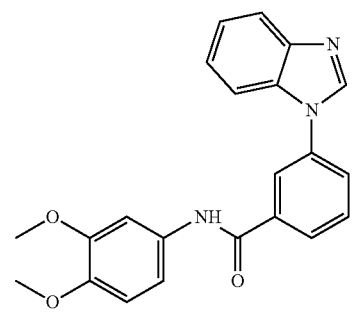
Amd-a7
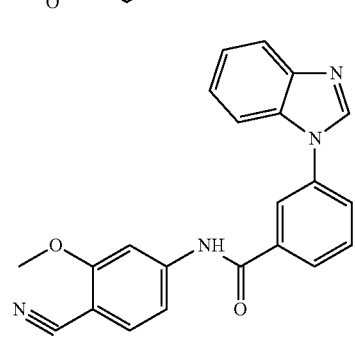
Amd-a8

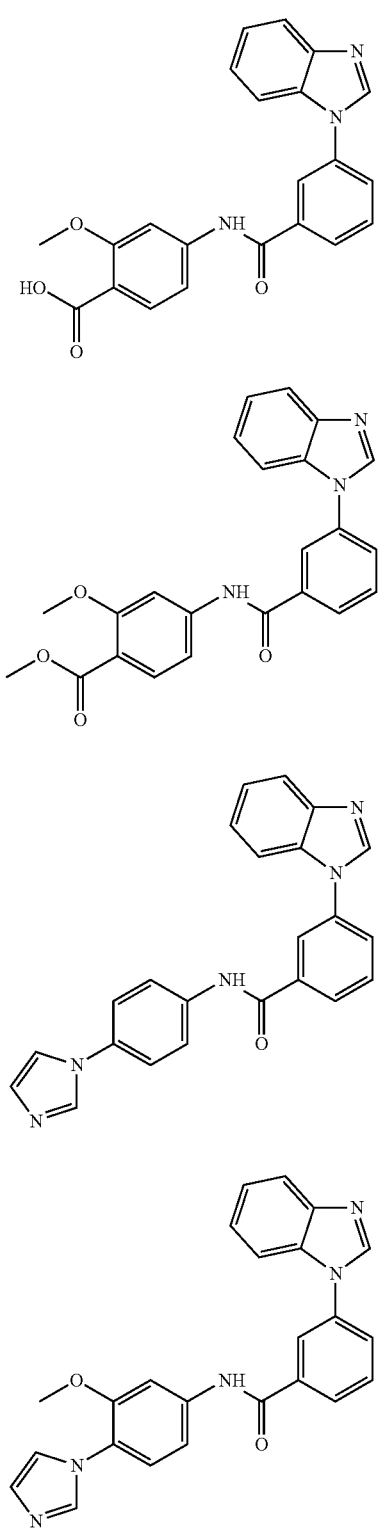
Amd-a9
Amd-a10
Amd-a11
Amd-a12
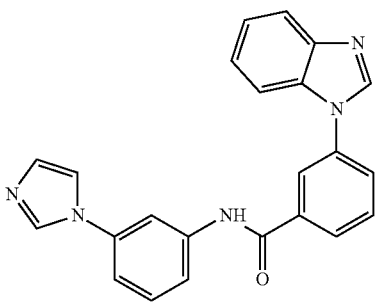
Amd-a13
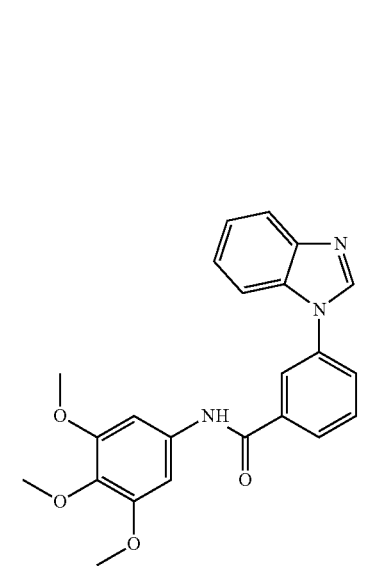
Amd-a14
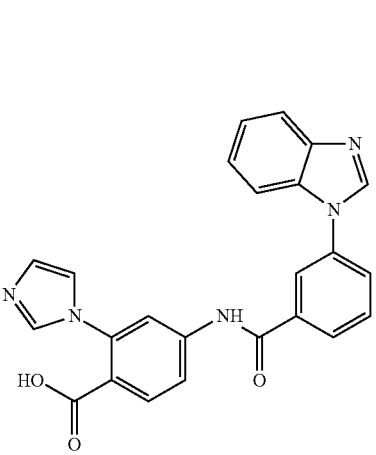
Amd-a15
TABLE 4a
| Amide derivatives (Amd-a series) | |
|---|---|
| Amd-a1 | (3-benzimidazolylphenyl)-N-(4-hydroxyphenyl)carboxamide |
| Amd-a2 | (3-benzimidazolylphenyl)-N-(4-methoxyphenyl)carboxamide |

TABLE 4a-continued

Amide derivatives (Amd-a series)

| | |
|---|---|
| Amd-a3 | (3-benzimidazolylphenyl)-N-(4-cyanophenyl)carboxamide |
| Amd-a4 | 4-[(3-benzimidazolylphenyl)carbonylamino]benzoic acid |
| Amd-a5 | methyl 4-[(3-benzimidazolylphenyl)carbonylamino]benzoate |
| Amd-a6 | (3-benzimidazolylphenyl)-N-(4-hydroxy-3-methoxyphenyl)carboxamide |
| Amd-a7 | (3-benzimidazolylphenyl)-N-(3,4-dimethoxyphenyl)carboxamide |
| Amd-a8 | (3-benzimidazolylphenyl)-N-(4-cyano-3-methoxyphenyl)carboxamide |
| Amd-a9 | 4-[(3-benzimidazolylphenyl)carbonylamino]-2-methoxybenzoic acid |
| Amd-a10 | methyl 4-[(3-benzimidazolylphenyl)carbonylamino]-2-methoxybenzoate |
| Amd-a11 | (3-benzimidazolylphenyl)-N-(4-imidazolylphenyl)carboxamide |
| Amd-a12 | (3-benzimidazolylphenyl)-N-(4-imidazolyl-3-methoxyphenyl)carboxamide |
| Amd-a13 | (3-benzimidazolylphenyl)-N-(3-imidazolylphenyl)carboxamide |
| Amd-a14 | (3-benzimidazolylphenyl)-N-(3,4,5-trimethoxyphenyl)carboxamide |
| Amd-a15 | 4-[(3-benzimidazolylphenyl)carbonylamino]-2-imidazolylbenzoic acid |

Amide Derivatives (Amd-b Series)

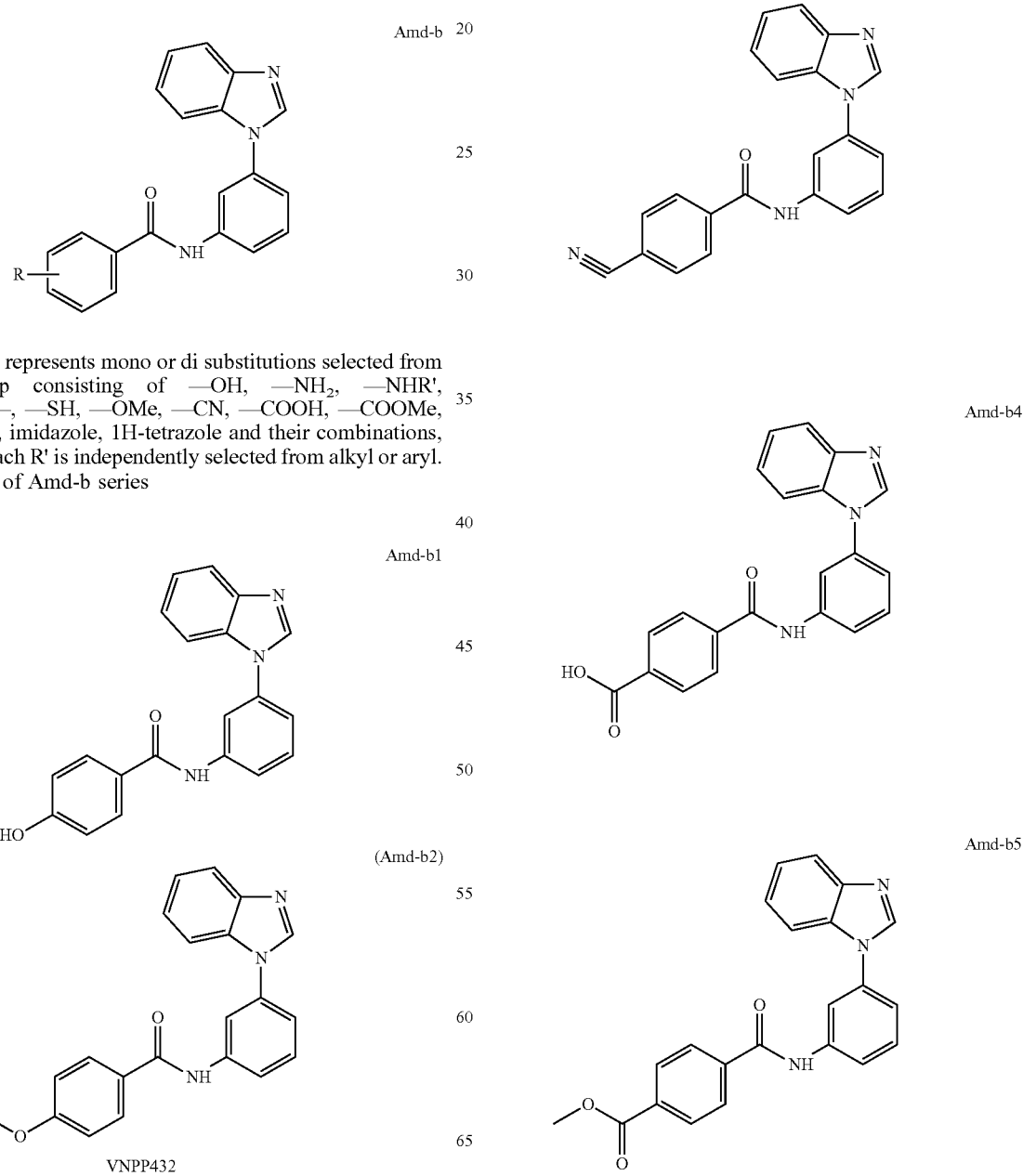

wherein is represents mono or di substitutions selected from the group consisting of —OH, —NH$_2$, —NHR', —N(R')$_2$—, —SH, —OMe, —CN, —COOH, —COOMe, —COOEt, imidazole, 1H-tetrazole and their combinations, wherein each R' is independently selected from alkyl or aryl. Examples of Amd-b series -continued
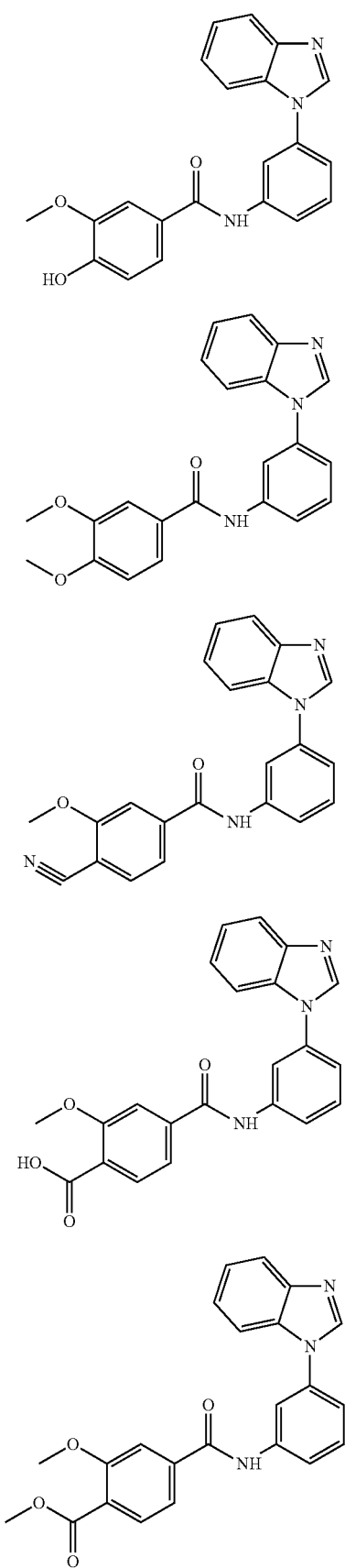
Amd-b6
Amd-b7
Amd-b8
Amd-b9
Amd-b10
-continued
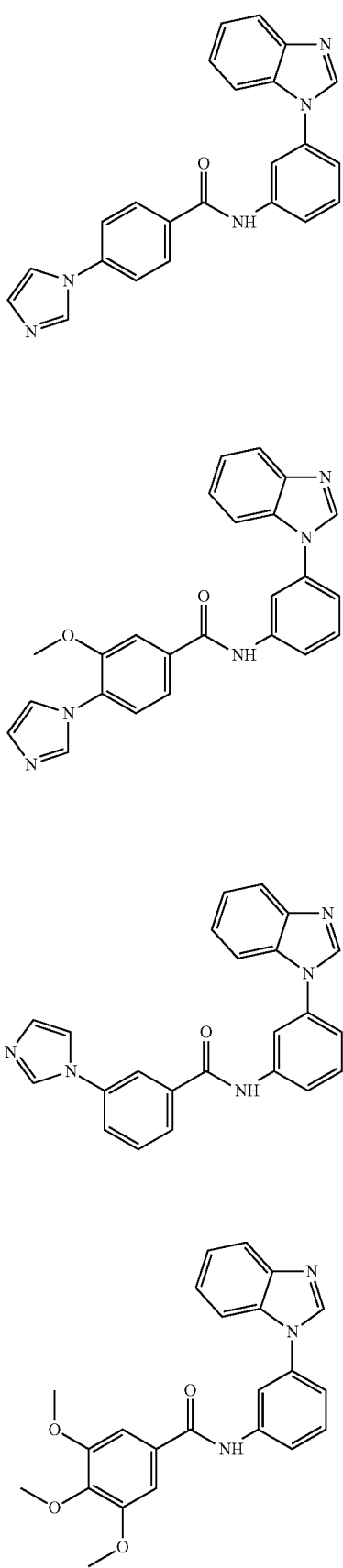
Amd-b11
Amd-b12
Amd-b13
Amd-b14

-continued

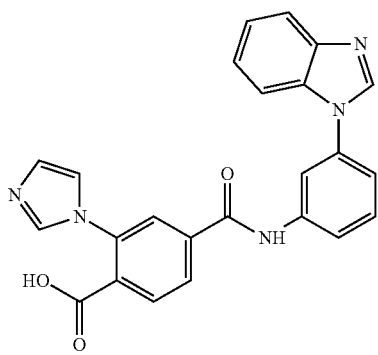

Amd-b15

Examples of Am-a series

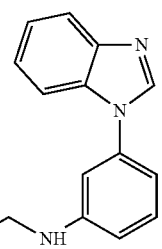

(Am-a1)

VNPP428

TABLE 4b

Amide derivatives (Amd-b series)

| | |
|---|---|
| Amd-b1 | N-(3-benzimidazolylphenyl)(4-hydroxyphenyl)carboxamide |
| VNPP432(Amd-b2) | N-(3-benzimidazolylphenyl)(4-methoxyphenyl)carboxamide |
| Amd-b3 | N-(3-benzimidazolylphenyl)(4-cyanophenyl)carboxamide |
| Amd-b4 | 4-[N-(3-benzimidazolylphenyl)carbamoyl]benzoic acid |
| Amd-b5 | methyl 4-[N-(3-benzimidazolylphenyl)carbamoyl]benzoate |
| Amd-b6 | N-(3-benzimidazolylphenyl)(4-hydroxy-3-methoxyphenyl)carboxamide |
| Amd-b7 | N-(3-benzimidazolylphenyl)(3,4-dimethoxyphenyl)carboxamide |
| Amd-b8 | N-(3-benzimidazolylphenyl)(4-cyano-3-methoxyphenyl)carboxamide |
| Amd-b9 | 4-[N-(3-benzimidazolylphenyl)carbamoyl]-2-methoxybenzoic acid |
| Amd-b10 | methyl 4-[N-(3-benzimidazolylphenyl)carbamoyl]-2-methoxybenzoate |
| Amd-b11 | N-(3-benzimidazolylphenyl)(4-imidazolylphenyl)carboxamide |
| Amd-b12 | N-(3-benzimidazolylphenyl)(4-imidazolyl-3-methoxyphenyl)carboxamide |
| Amd-b13 | N-(3-benzimidazolylphenyl)(3-imidazolylphenyl)carboxamide |
| Amd-b14 | N-(3-benzimidazolylphenyl)(3,4,5-trimethoxyphenyl)carboxamide |
| Amd-b15 | 4-[N-(3-benzimidazolylphenyl)carbamoyl]-2-imidazolylbenzoic acid |

Amine Derivatives (Am-a Series)

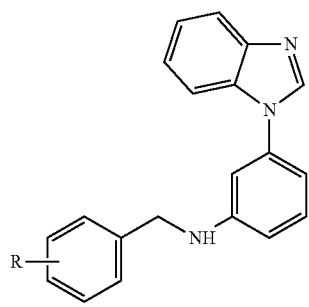

Am-a

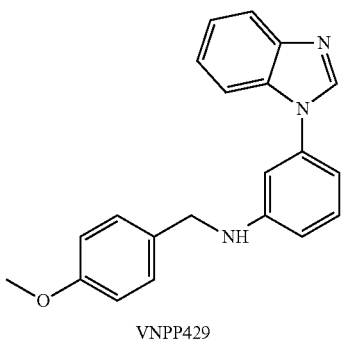

(Am-a2)

VNPP429

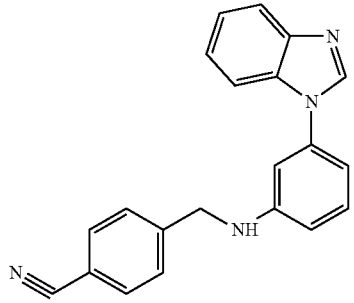

Am-a3 wherein R represents mono or di substitutions selected from the group consisting of —OH, —NH$_2$, —NM', —SH, —OMe, —CN, —COOH, —COOMe, —COOEt, imidazole, 1H-tetrazole and their combinations, wherein each R' is independently selected from alkyl or aryl.

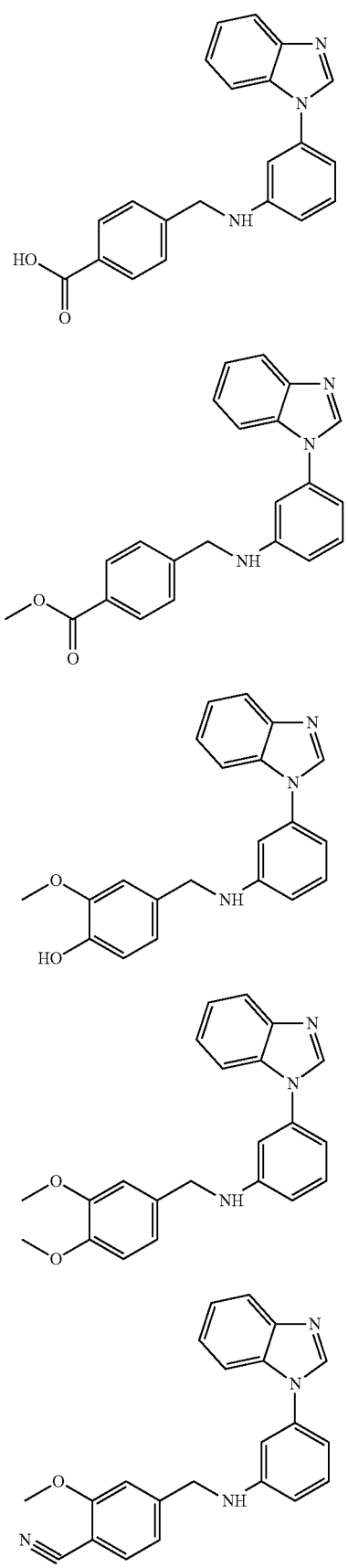
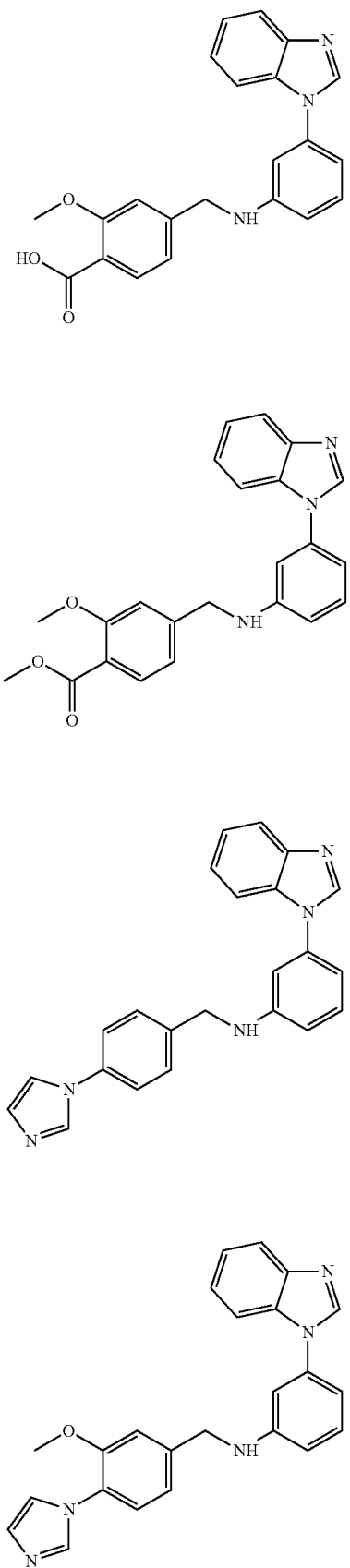

Am-a13

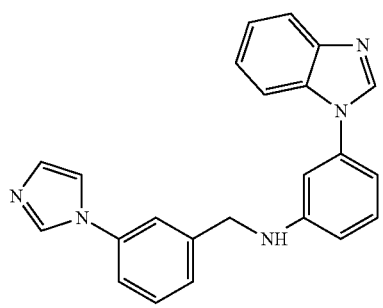

Am-a14

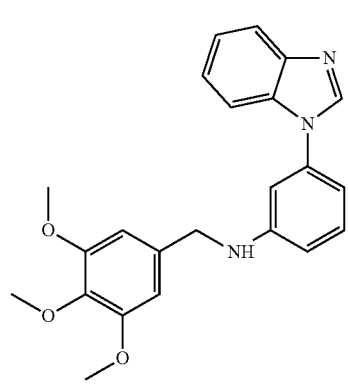

Am-a15

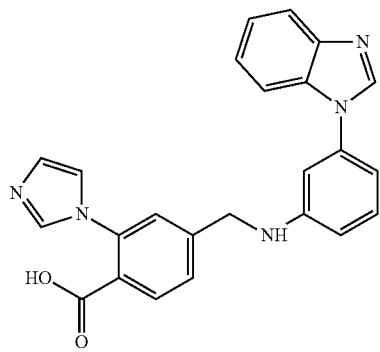

Amine Derivatives (Am-b Series)

Am-b

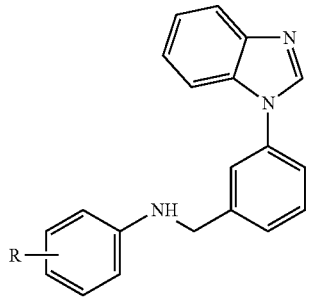

wherein R represents mono or di substitutions selected from the group consisting of —OH, —NH$_2$, —NHR', —N(R')$_2$—, —SH, —OMe, —CN, —COOH, —COOMe, —COOEt, imidazole, 1H-tetrazole and their combinations, wherein each R' is independently selected from alkyl or aryl.

Examples of Am-a Series

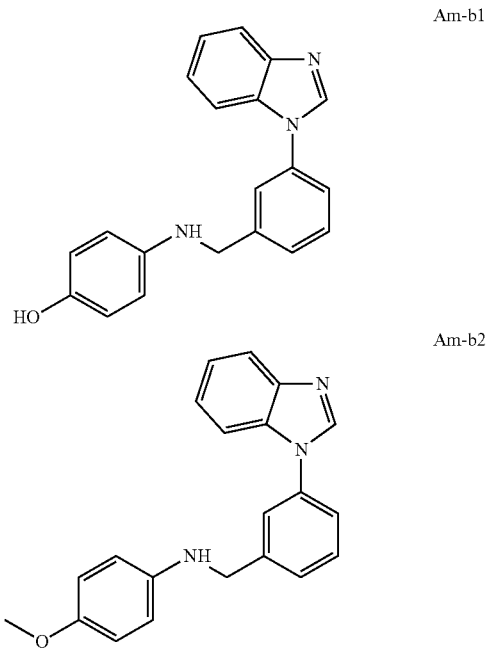

TABLE 5a

| | |
|---|---|
| VNPP428(Am-a1) | 4-{[(3-benzimidazolylphenyl)amino]methyl}phenol |
| VNPP429(Am-a2) | (3-benzimidazolylphenyl)[(4-methoxyphenyl)methyl]amine |
| Am-a3 | 4-{[(3-benzimidazolylphenyl)amino]methyl}benzenecarbonitrile |
| Am-a4 | 4-{[(3-benzimidazolylphenyl)amino]methyl}benzoic acid |
| Am-a5 | methyl 4-{[(3-benzimidazolylphenyl)amino]methyl}benzoate |
| Am-a6 | 4-{[(3-benzimidazolylphenyl)amino]methyl}-2-methoxyphenol |
| Am-a7 | (3-benzimidazolylphenyl)[(3,4-dimethoxyphenyl)methyl]amine |
| Am-a8 | 4-{[(3-benzimidazolylphenyl)amino]methyl}-2-methoxybenzenecarbonitrile |
| Am-a9 | 4-{[(3-benzimidazolylphenyl)amino]methyl}-2-methoxybenzoic acid |
| Am-a10 | methyl 4-{[(3-benzimidazolylphenyl)amino]methyl}-2-methoxybenzoate |
| Am-a11 | (3-benzimidazolylphenyl)[(4-imidazolylphenyl)methyl]amine |
| Am-a12 | (3-benzimidazolylphenyl)[(4-imidazolyl-3-methoxyphenyl)methyl]amine |
| Am-a13 | (3-benzimidazolylphenyl)[(3-imidazolylphenyl)methyl]amine |
| Am-a14 | (3-benzimidazolylphenyl)[(3,4,5-trimethoxyphenyl)methyl]amine |
| Am-a15 | 4-{[(3-benzimidazolylphenyl)amino]methyl}-2-imidazolylbenzoic acid |

Am-b3
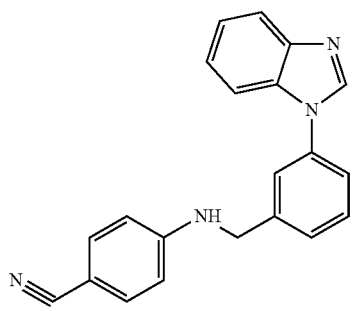
Am-b4
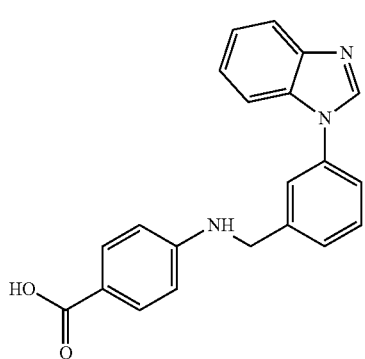
Am-b5
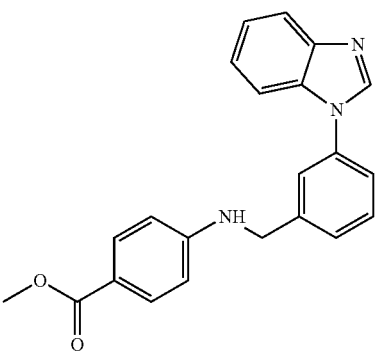
Am-b6
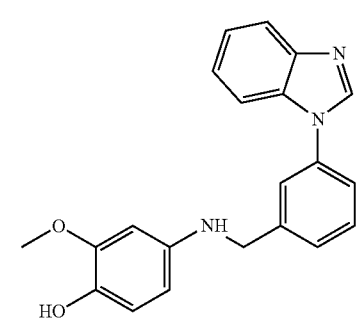
Am-b7
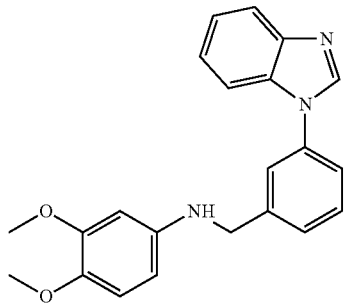
Am-b8
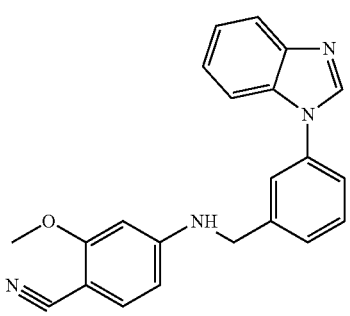
Am-b9
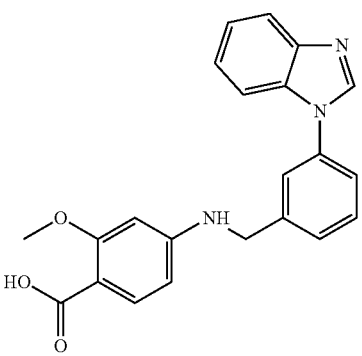
Am-b10
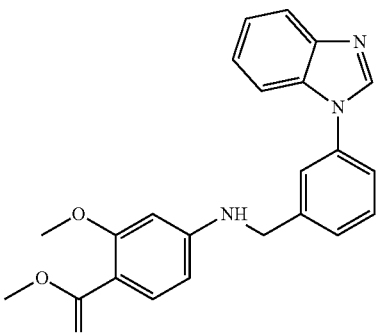

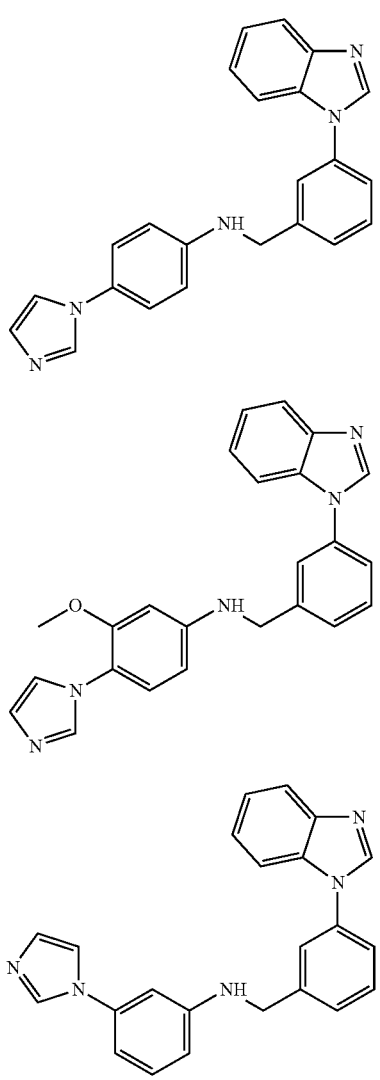
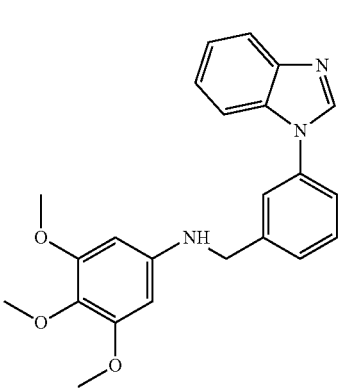

TABLE 5b

Amine derivatives (Am-b series)

| | |
|---|---|
| Am-b1 | 4-{[(3-benzimidazolylphenyl)methyl]amino}phenol |
| Am-b2 | [(3-benzimidazolylphenyl)methyl](4-methoxyphenyl)amine |
| Am-b3 | 4-{[(3-benzimidazolylphenyl)methyl]amino}benzenecarbonitrile |
| Am-b4 | 4-{[(3-benzimidazolylphenyl)methyl]amino}benzoic acid |
| Am-b5 | methyl 4-{[(3-benzimidazolylphenyl)methyl]amino}benzoate |
| Am-b6 | 4-{[(3-benzimidazolylphenyl)methyl]amino}-2-methoxyphenol |
| Am-b7 | [(3-benzimidazolylphenyl)methyl](3,4-dimethoxyphenyl)amine |
| Am-b8 | 4-{[(3-benzimidazolylphenyl)methyl]amino}-2-methoxybenzenecarbonitrile |
| Am-b9 | 4-{[(3-benzimidazolylphenyl)methyl]amino}-2-methoxybenzoic acid |
| Am-b10 | methyl 4-{[(3-benzimidazolylphenyl)methyl]amino}-2-methoxybenzoate |
| Am-b11 | [(3-benzimidazolylphenyl)methyl](4-imidazolylphenyl)amine |
| Am-b12 | [(3-benzimidazolylphenyl)methyl](4-imidazolyl-3-methoxyphenyl)amine |
| Am-b13 | [(3-benzimidazolylphenyl)methyl](3-imidazolylphenyl)amine |
| Am-b14 | [(3-benzimidazolylphenyl)methyl](3,4,5-trimethoxyphenyl)amine |
| Am-b15 | 4-{[(3-benzimidazolylphenyl)methyl]amino}-2-imidazolylbenzoic acid |

Sulphonamide Series—SulAmd Series

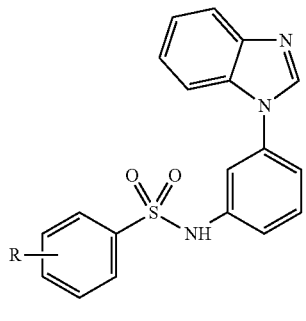

SulAmd wherein R represents mono or di substitutions selected from the group consisting of —OH, —NH$_2$, —NHR', —N(R')$_2$—, —SH, —OMe, —CN, —COOH, —COOMe, —COOEt, imidazole, 1H-tetrazole and their combinations, wherein each R' is independently selected from alkyl or aryl.

Examples of SulAmd Series

SulAmd-1

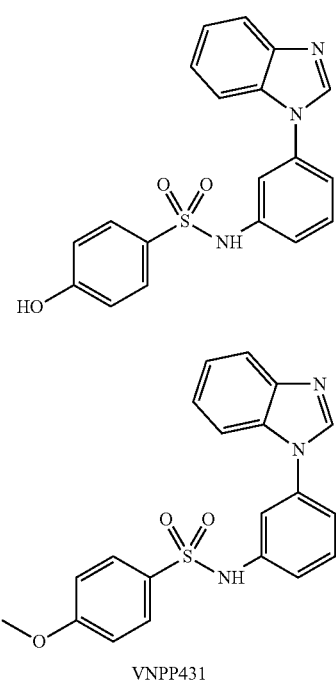

VNPP431 (SulAmd-2)

SulAmd-3

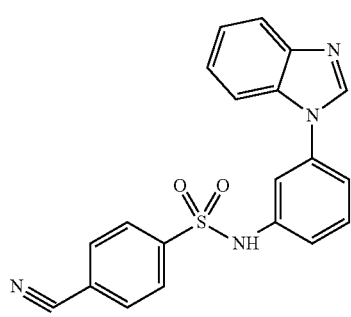

SulAmd-4

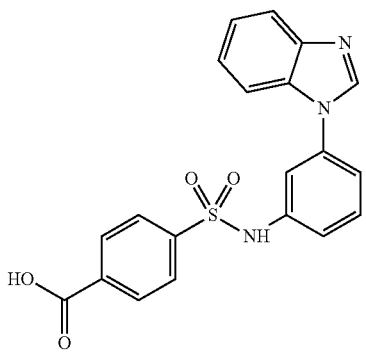

SulAmd-5

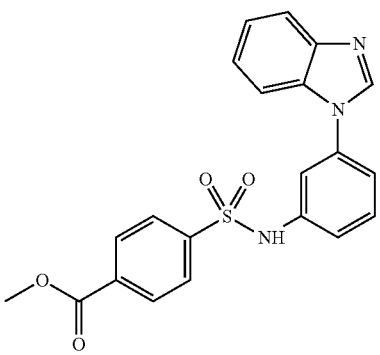

SulAmd-6

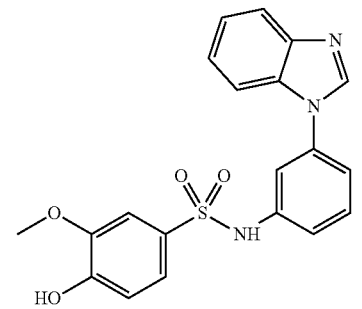

SulAmd-7

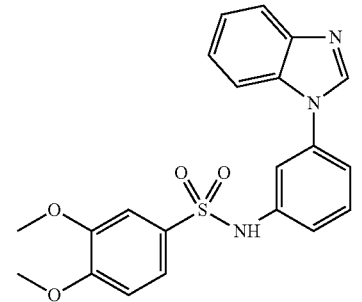

SulAmd-8

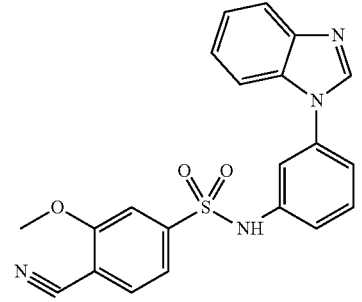

-continued
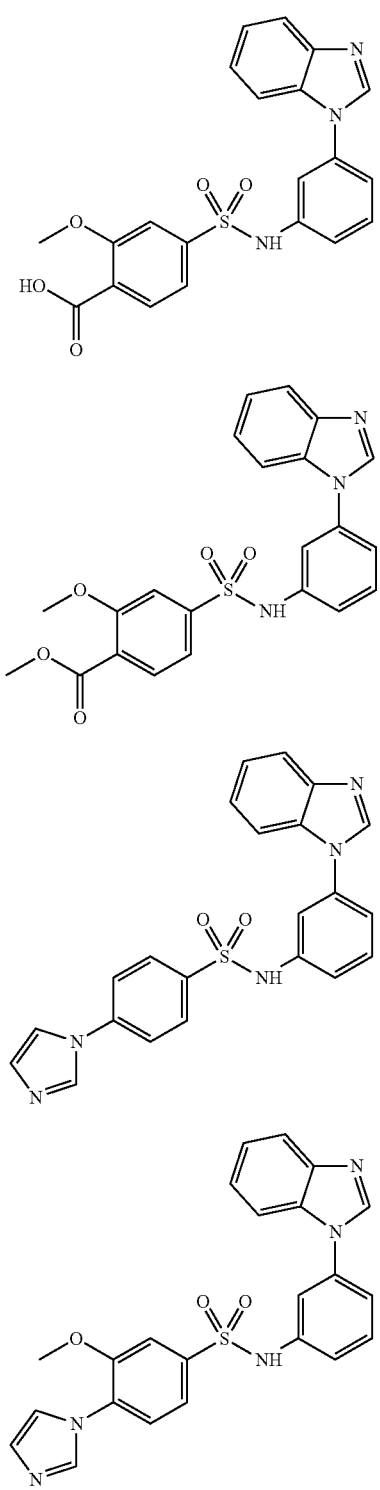
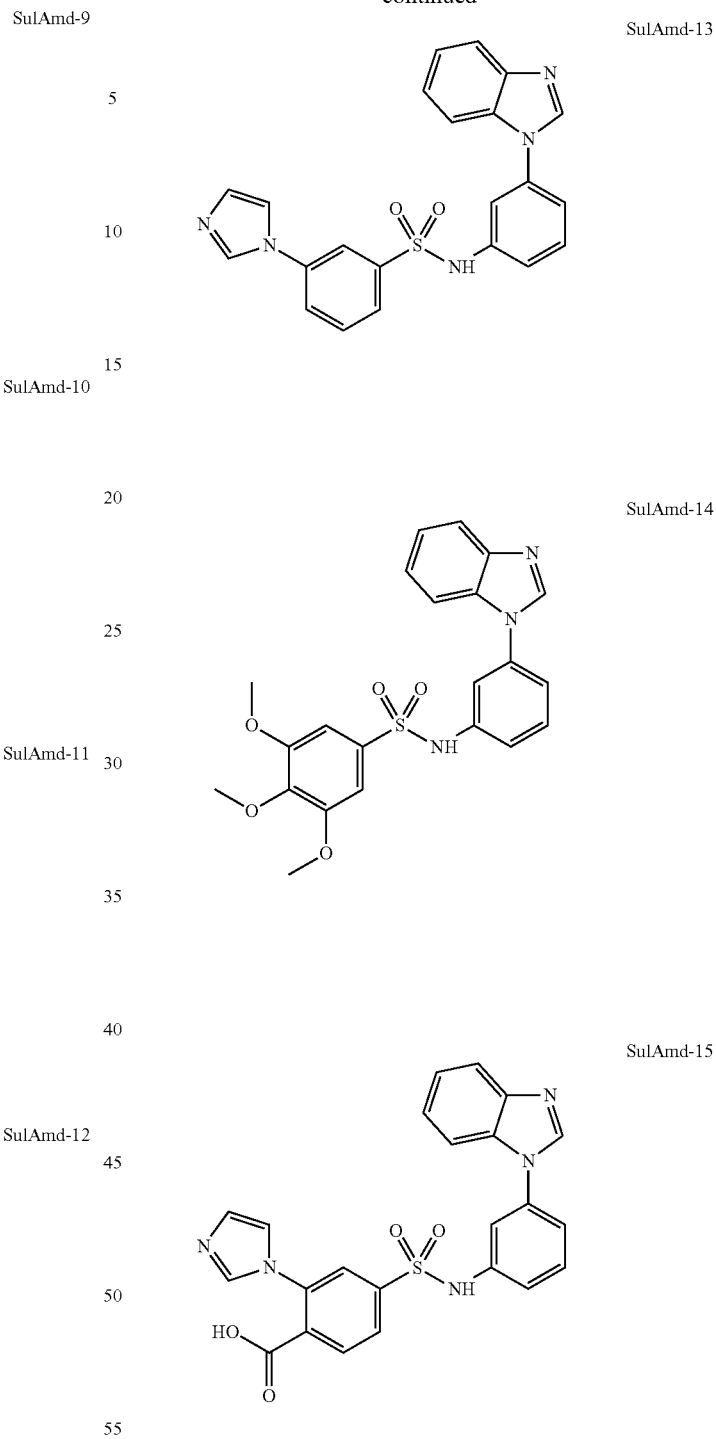
TABLE 6
| Sulphonamide series - SulAmd series | |
|---|---|
| SulAmd1 | N-(3-benzimidazolylphenyl)[(4-hydroxyphenyl)sulphonyl]amine |
| VNPP431 (SulAmd2) | N-(3-benzimidazolylphenyl)[(4-methoxyphenyl) sulphonyl]amine |
| SulAmd3 | N-(3-benzimidazolylphenyl)[(4-cyanophenyl) sulphonyl]amine |

TABLE 6-continued

Sulphonamide series - SulAmd series

| | |
|---|---|
| SulAmd4 | 4-[N-(3-benzimidazolylphenyl)Sulphonamyl]benzoic acid |
| SulAmd5 | methyl 4-[N-(3-benzimidazolylphenyl)Sulphonamyl]benzoate |
| SulAmd6 | N-(3-benzimidazolylphenyl)[(4-hydroxy-3-methoxyphenyl) sulphonyl]amine |
| SulAmd7 | N-(3-benzimidazolylphenyl)[(3,4-dimethoxyphenyl) sulphonyl]amine |
| SulAmd8 | N-(3-benzimidazolylphenyl)[(4-cyano-3-methoxyphenyl) sulphonyl]amine |
| SulAmd9 | 4-[N-(3-benzimidazolylphenyl)Sulphonamyl]-2-methoxybenzoic acid |
| SulAmd10 | methyl 4-[N-(3-benzimidazolylphenyl)Sulphonamyl]-2-methoxybenzoate |
| SulAmd11 | N-(3-benzimidazolylphenyl)[(4-imidazolylphenyl) sulphonyl]amine |
| SulAmd12 | N-(3-benzimidazolylphenyl)[(4-imidazolyl-3-methoxyphenyl) sulphonyl]amine |
| SulAmd13 | N-(3-benzimidazolylphenyl)[(3-imidazolylphenyl) sulphonyl]amine |
| SulAmd14 | N-(3-benzimidazolylphenyl)[(3,4,5-trimethoxyphenyl) sulphonyl]amine |
| SulAmd15 | 4-[N-(3-benzimidazolylphenyl)Sulphonamyl]-2-imidazolylbenzoic acid |

Tetrahydroisoquinoline Derivatives (Q Series)

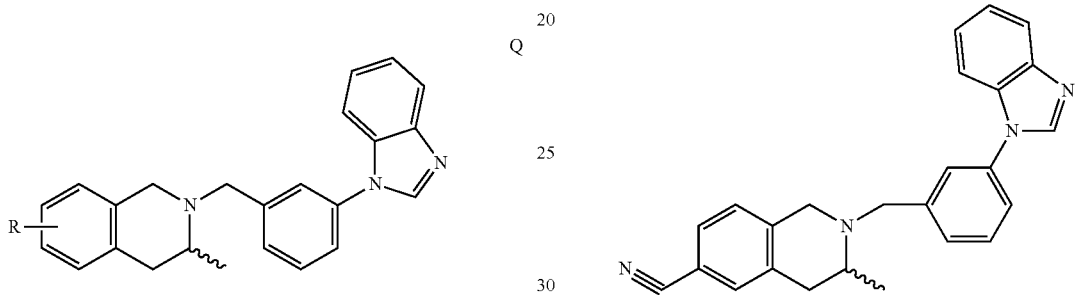

wherein R represents mono or di substitutions selected from the group consisting of —OH, —NH$_2$, —NHR', —SH, —OMe, —CN, —COOH, —COOMe, —COOEt, imidazole, 1H-tetrazole and their combinations, wherein each R' is independently selected from alkyl or aryl. The squiggly line represents an α or β-methyl group that may be either projecting in front of the plane of the paper or projecting behind the plane of the paper.

Examples of Q series

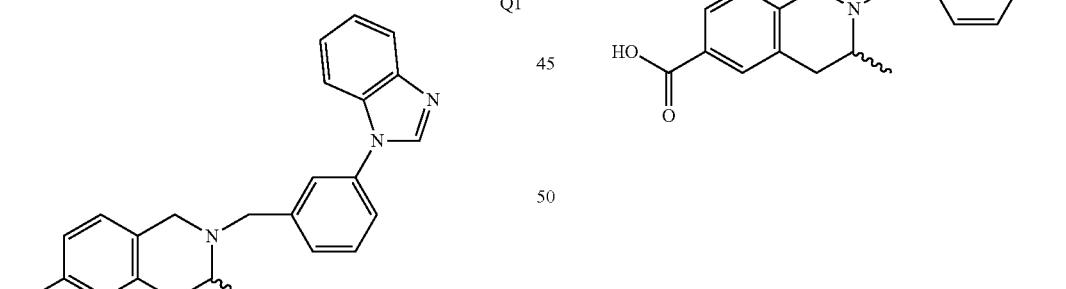

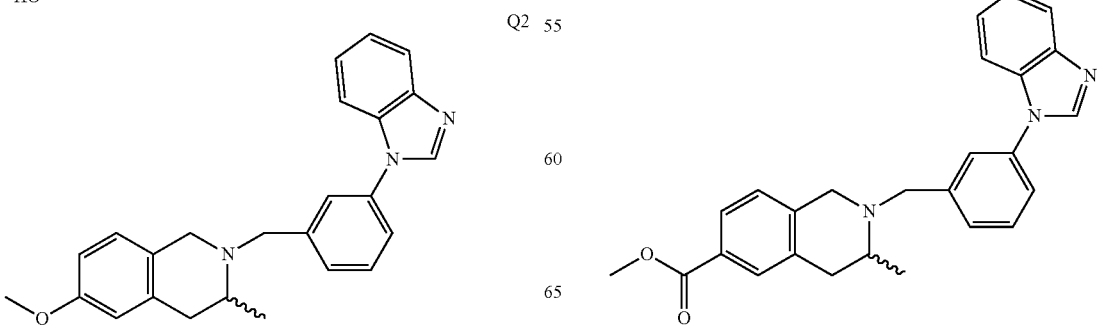

Q6 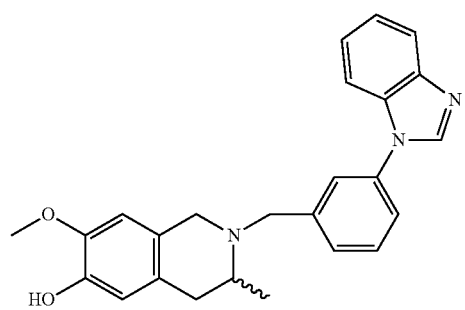
Q7 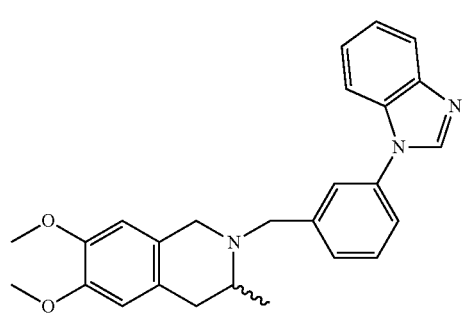
Q8 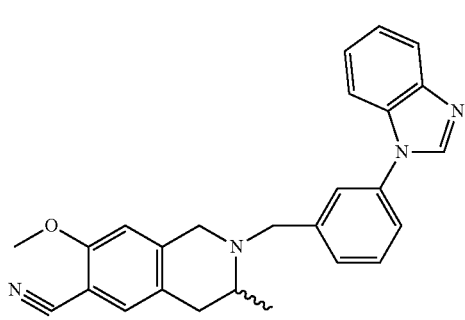
Q9 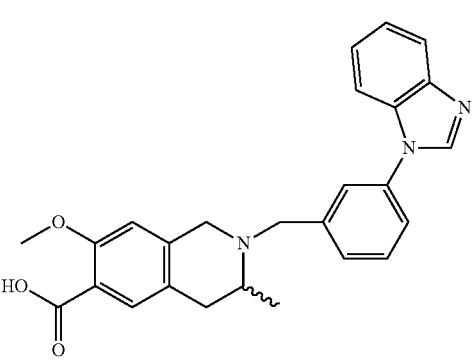
Q10 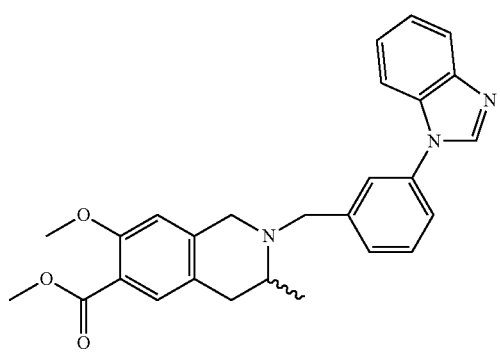
Q11 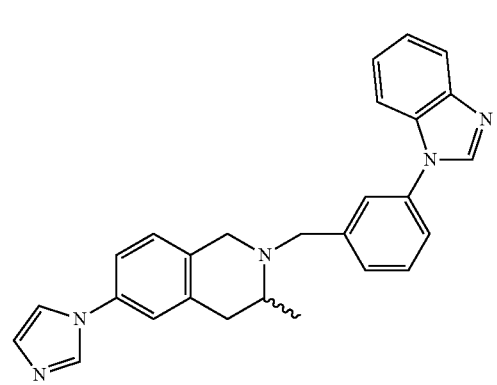
Q12 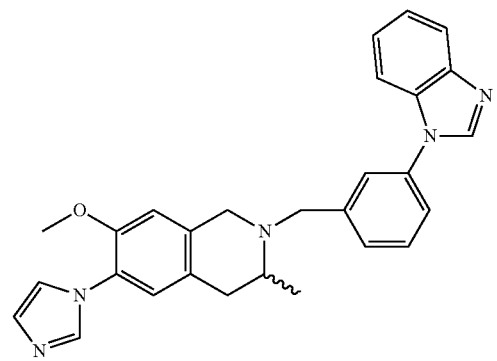
Q13 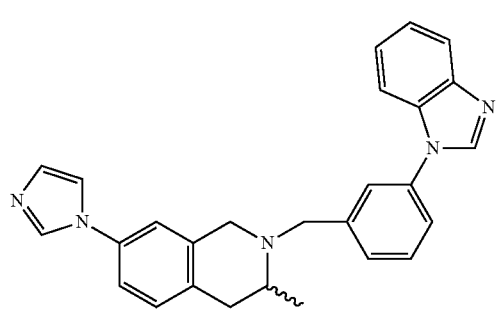

-continued

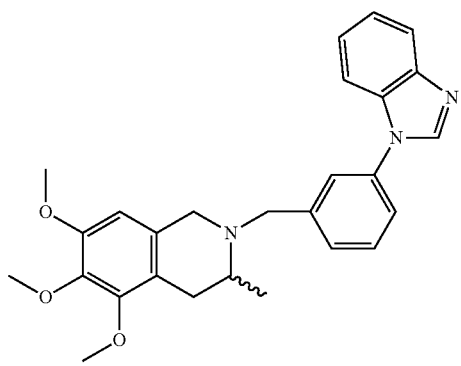

Q14

The two squiggly lines on the right side of each partial structure below are an abbreviation for the rest of the andorostene derivative molecule. See formula A.

Examples of Androstene Derivatives (A)

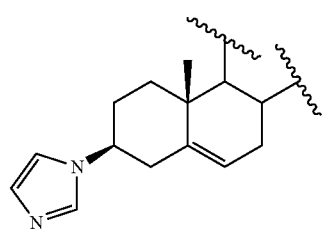

(A1)

VNPP433-3β

TABLE 7

Tetrahydroisoquinoline derivatives (Q series)

| | |
|---|---|
| Q1 | 2-[(3-benzimidazolylphenyl)methyl]-3-methyl-1,2,3,4-tetrahydroisoquinolin-6-ol (Q1) |
| Q2 | 2-[(3-benzimidazolylphenyl)methyl]-6-methoxy-3-methyl-1,2,3,4-tetrahydroisoquinoline (Q2) |
| Q3 | 2-[(3-benzimidazolylphenyl)methyl]-3-methyl-1,2,3,4-tetrahydroisoquinoline-6-carbonitrile (Q3) |
| Q4 | 2-[(3-benzimidazolylphenyl)methyl]-3-methyl-1,2,3,4-tetrahydroisoquinoline-6-carboxylic acid (Q4) |
| Q5 | methyl 2-[(3-benzimidazolylphenyl)methyl]-3-methyl-1,2,3,4-tetrahydroisoquinoline-6-carboxylate (Q5) |
| Q6 | 2-[(3-benzimidazolylphenyl)methyl]-7-methoxy-3-methyl-1,2,3,4-tetrahydroisoquinolin-6-ol (Q6) |
| Q7 | 2-[(3-benzimidazolylphenyl)methyl]-6,7-dimethoxy-3-methyl-1,2,3,4-tetrahydroisoquinoline (Q7) |
| Q8 | 2-[(3-benzimidazolylphenyl)methyl]-7-methoxy-3-methyl-1,2,3,4-tetrahydroisoquinoline-6-carbonitrile (Q8) |
| Q9 | 2-[(3-benzimidazolylphenyl)methyl]-7-methoxy-3-methyl-1,2,3,4-tetrahydroisoquinoline-6-carboxylic acid (Q9) |
| Q10 | methyl 2-[(3-benzimidazolylphenyl)methyl]-7-methoxy-3-methyl-1,2,3,4-tetrahydroisoquinoline-6-carboxylate (Q10) |
| Q11 | {3-[(6-imidazolyl-3-methyl-2-1,2,3,4-tetrahydroisoquinolyl)methyl]phenyl}benzimidazole (Q11) |
| Q12 | 2-[(3-benzimidazolylphenyl)methyl]-6-imidazolyl-7-methoxy-3-methyl-1,2,3,4-tetrahydroisoquinoline (Q12) |
| Q13 | {3-[(7-imidazolyl-3-methyl-2-1,2,3,4-tetrahydroisoquinolyl)methyl]phenyl}benzimidazole (Q13) |
| Q14 | 2-[(3-benzimidazolylphenyl)methyl]-5,6,7-trimethoxy-3-methyl-1,2,3,4-tetrahydroisoquinoline (Q14) |

Androstene Derivatives

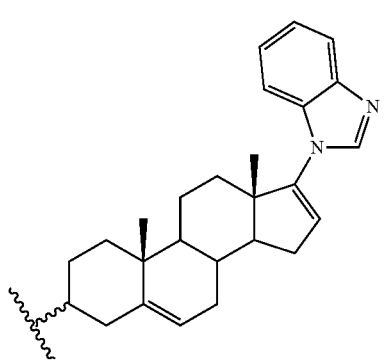

A

The two squiggly lines attached directly to the compound A represent a substituent group that may be either projecting in front of the plane of the paper (example (A1) or projecting behind the plane of the paper (example Example A3).

-continued

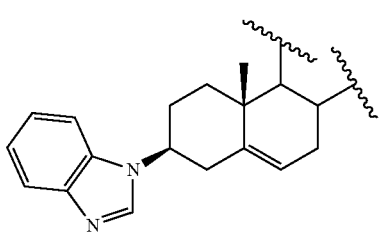

A2

-continued (A3) VNPP433-3α

(A4)

(A5) VNPP397

(A6)

(A7)

(A8)

(A9)

-continued

A10

A11

A12

A13

A14

(A15) VNPP415C (A16) VNPP414C

A17 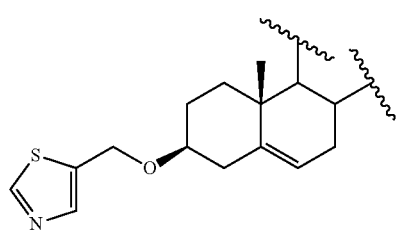
A18 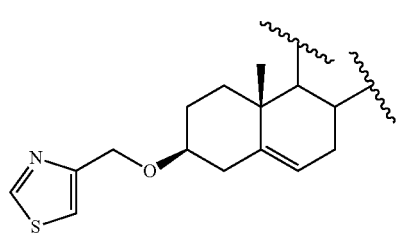
A19 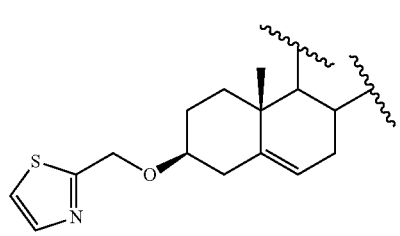
A20 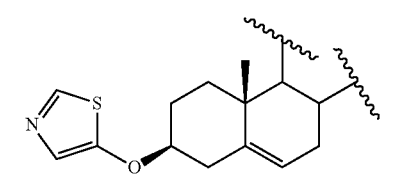
A21 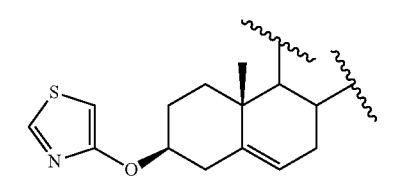
A22 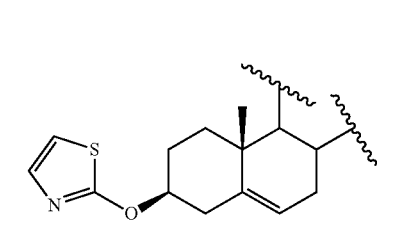
A23 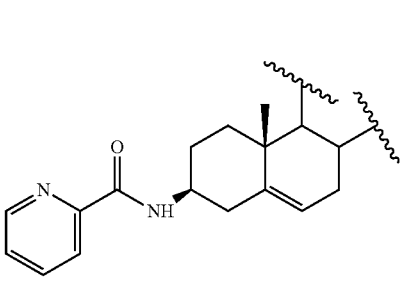
A24 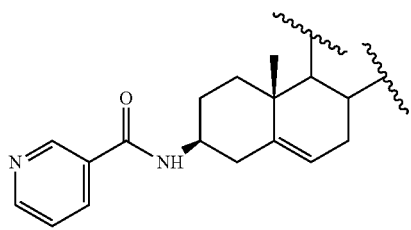
A25 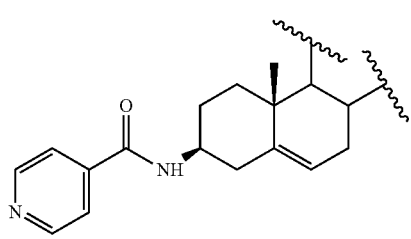
A26 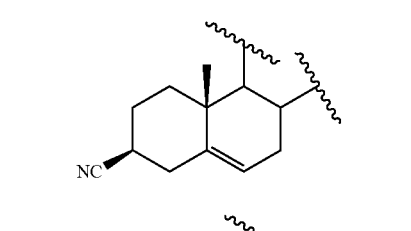
A27 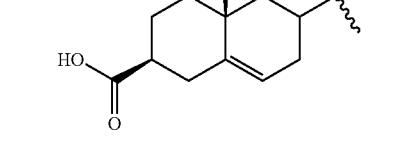
A28 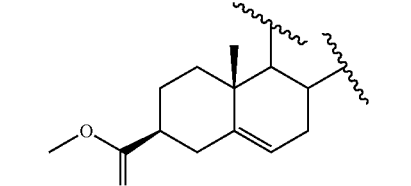
A29 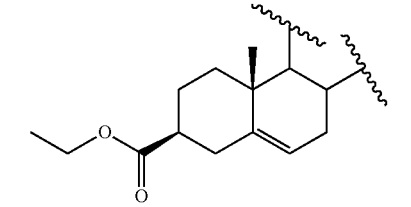
A30 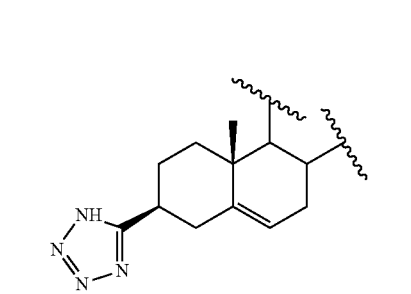

-continued

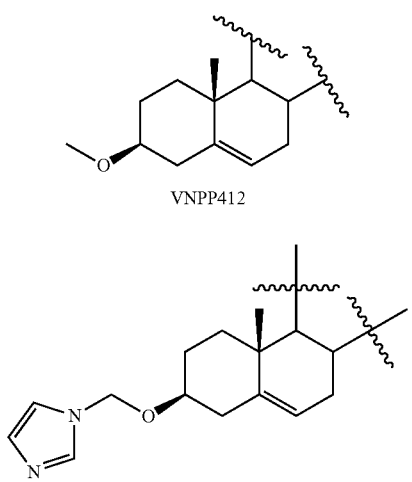

VNPP412

Estrogen Derivatives

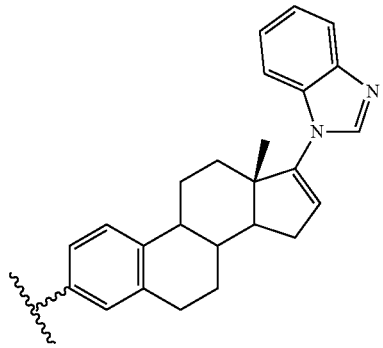

E

The two squiggly lines attached directly to the compound A represent a substituent group that may be either projecting

TABLE 8

| Androstene derivatives | |
|---|---|
| VNPP₄₃₃-3β (2d)(A1) | 3β-(1H-imidazol-1-yl)-17-(1H-benzimidazol-1-yl)androsta-5,16-diene |
| VNPP433 (A2) | 3β-(1H-benzimidazol-1-yl)-17-(1H-benzimidazol-1-yl)androsta-5,16-diene |
| VNPP433-3α (A3) | 3α-(1H-imidazol-1-yl)-17-(1H-benzimidazol-1-yl)androsta-5,16-diene |
| A4 | 3α-(1H-benzimidazol-1-yl)-17-(1H-benzimidazol-1-yl)androsta-5,16-diene (A4) |
| VNPP397 (A5) | 3β-(1H-imidazole-1-thiocarboxylate)-17-(1H-benzimidazol-1-yl)androsta-5,16-diene |
| A6 | 3β-(1H-benzimidazole-1-carboxylate)-17-(1H-benzimidazol-1-yl)androsta-5,16-diene |
| A7 | 3β-(1H-benzimidazole-1-thiocarboxylate)-17-(1H-benzimidazol-1-yl)androsta-5,16-diene |
| A8 | 3β-Thiol-17-(1H-benzimidazol-1-yl)androsta-5,16-diene |
| A9 | 3β-(1H-imidazole-1-carbothioate)-17-(1H-benzimidazol-1-yl)androsta-5,16-diene |
| A10 | 3β-(1H-imidazole-1-carbodithioate)-17-(1H-benzimidazol-1-yl)androsta-5,16-diene |
| A11 | 3β-(pyridin-2-yloxy)-17-(1H-benzimidazol-1-yl)androsta-5,16-diene |
| A12 | 3β-(pyridin-3-yloxy)-17-(1H-benzimidazol-1-yl)androsta-5,16-diene |
| A13 | 3β-(pyridin-4-yloxy)-17-(1H-benzimidazol-1-yl)androsta-5,16-diene |
| A14 | 3β-(pyridin-2-ylmethoxy)-17-(1H-benzimidazol-1-yl)androsta-5,16-diene |
| VNPP415C (A15) | 3β-(pyridin-3-ylmethoxy)-17-(1H-benzimidazol-1-yl)androsta-5,16-diene |
| VNPP414 (A16) | 3β-(pyridin-4-ylmethoxy)-17-(1H-benzimidazol-1-yl)androsta-5,16-diene |
| A17 | 3β-(thiazol-5-ylmethoxy)-17-(1H-benzimidazol-1-yl)androsta-5,16-diene |
| A18 | 3β-(thiazol-4-ylmethoxy)-17-(1H-benzimidazol-1-yl)androsta-5,16-diene |
| A19 | 3β-(thiazol-2-ylmethoxy)-17-(1H-benzimidazol-1-yl)androsta-5,16-diene |
| A20 | 3β-(thiazol-5-yloxy)-17-(1H-benzimidazol-1-yl)androsta-5,16-diene |
| A21 | 3β-(thiazol-4-yloxy)-17-(1H-benzimidazol-1-yl)androsta-5,16-diene |
| A22 | 3β-(thiazol-2-yloxy)-17-(1H-benzimidazol-1-yl)androsta-5,16-diene |
| A23 | 3β-(picolinamide)-17-(1H-benzimidazol-1-yl)androsta-5,16-diene |
| A24 | 3β-(nicotinamide)-17-(1H-benzimidazol-1-yl)androsta-5,16-diene |
| A25 | 3β-(isonicotinamide)-17-(1H-benzimidazol-1-yl)androsta-5,16-diene |
| A26 | 3β-(nitrile)-17-(1H-benzimidazol-1-yl)androsta-5,16-diene |
| A27 | 3β-(carboxylic acid)-17-(1H-benzimidazol-1-yl)androsta-5,16-diene |
| A28 | 3β-(methylcarboxylate)-17-(1H-benzimidazol-1-yl)androsta-5,16-diene |
| A29 | 3β-(ethylcarboxylate)-17-(1H-benzimidazol-1-yl)androsta-5,16-diene |
| A30 | 3β-(1H-tetrazol-5-yl)-17-(1H-benzimidazol-1-yl)androsta-5,16-diene |
| VNPP412 (A31) | 3β-(Methoxy)-17-(1H-benzimidazol-1-yl)androsta-5,16-diene |
| A32 | 3β-(Imidazol-1-ylmethoxy)-17-(1H-benzimidazol-1-yl)androsta-5,16-diene | in front of the plane of the paper (example (A1) or projecting behind the plane of the paper (example Example A3).
The two squiggly lines on the right side of each partial structure below are an abbreviation for the rest of the andorostene derivative molecule. See formula A.
Examples of Estrogen Derivatives
E1
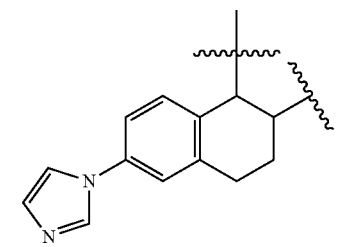
E2
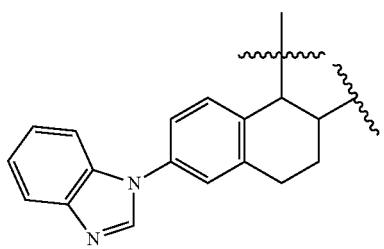
E3
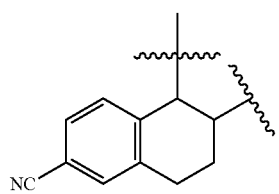
E4
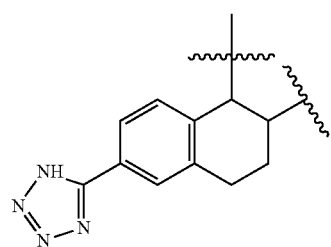
E5
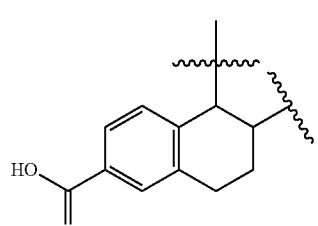
VNPP341
-continued
E6
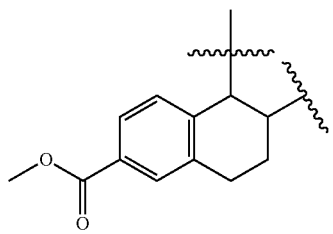
VNPP334
E7
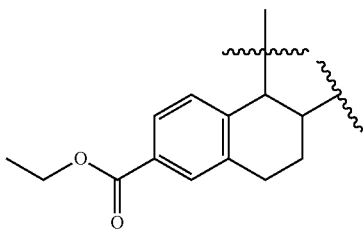
E8
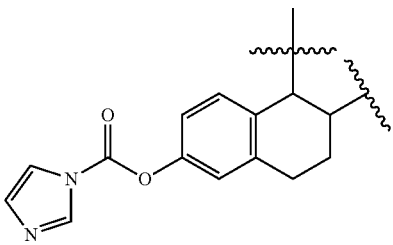
E9
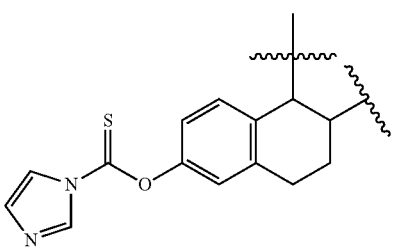
E10
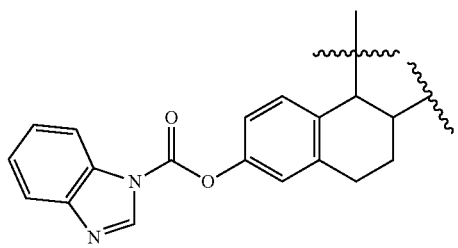
E11
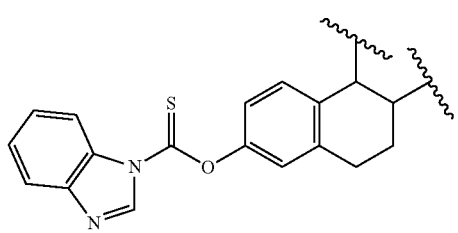

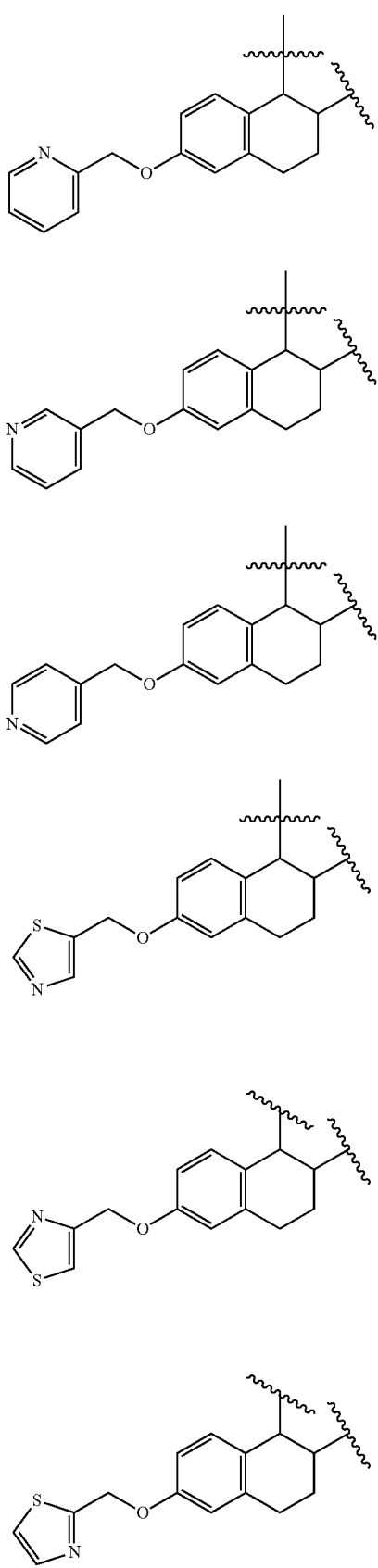
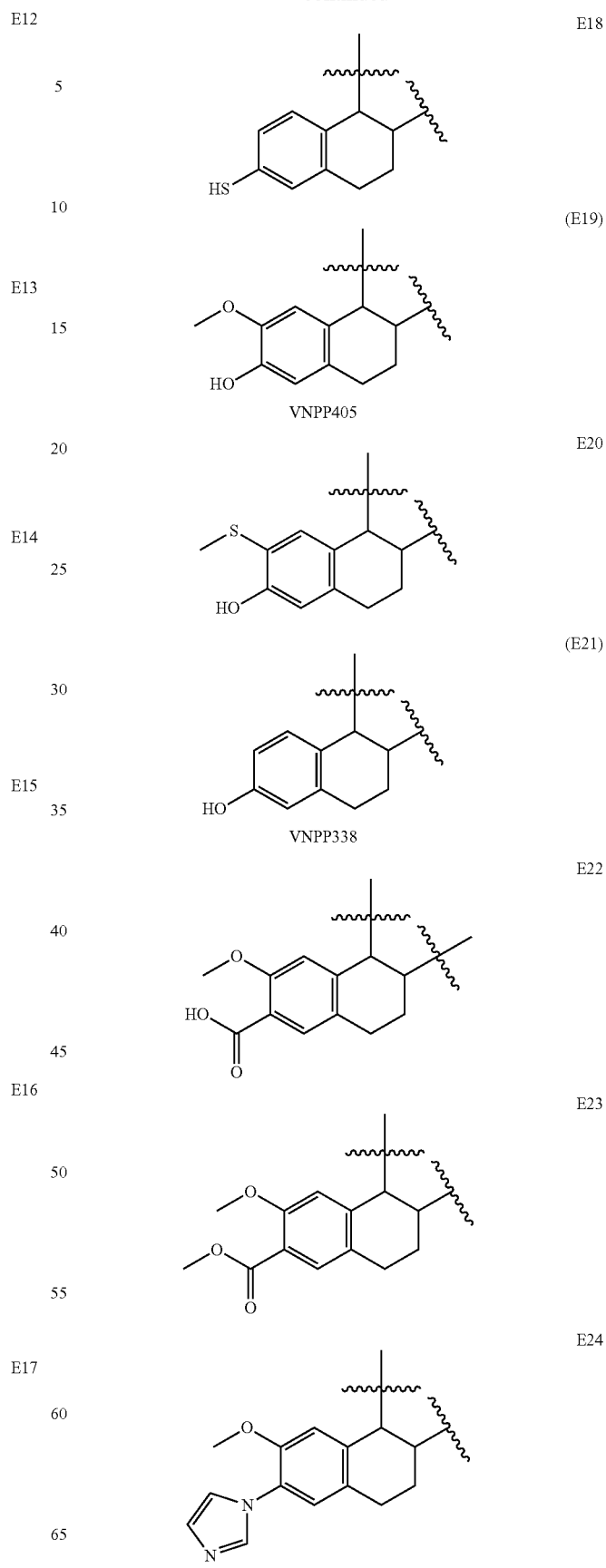

-continued
E25
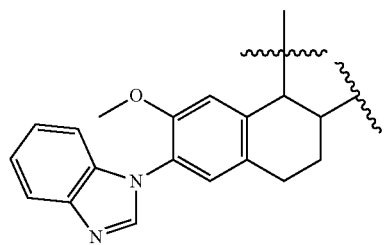
E26
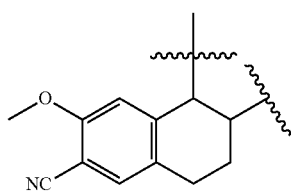
E27
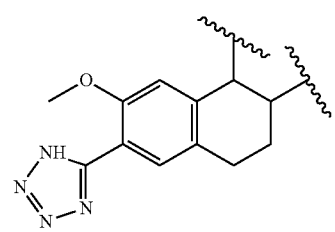
E28
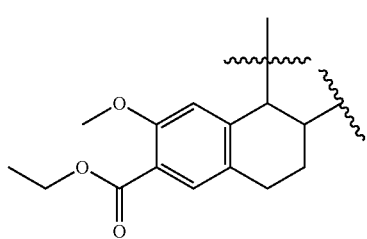
E29
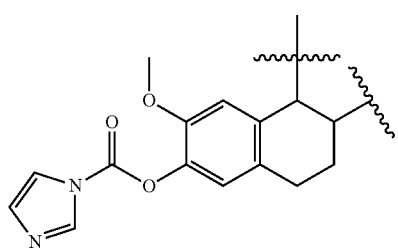
E30
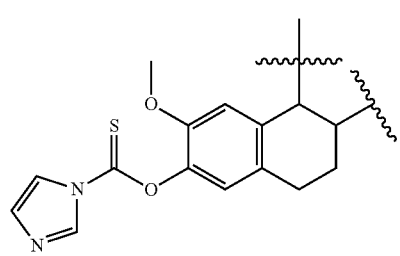
-continued
E31
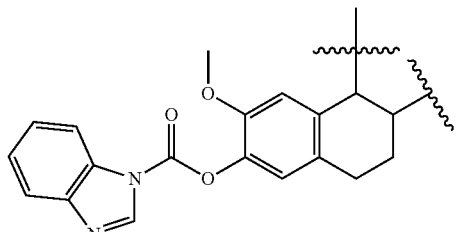
E32
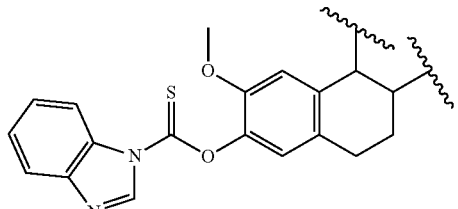
E33
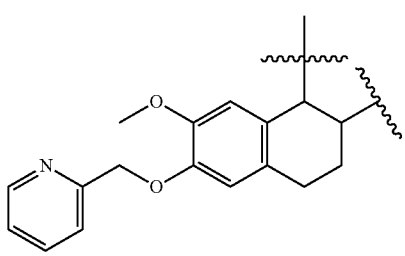
E34
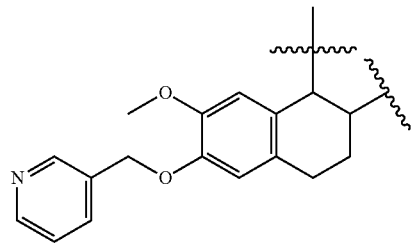
E35
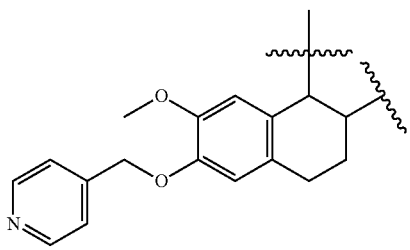
E36
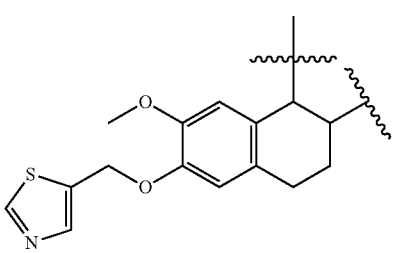

-continued

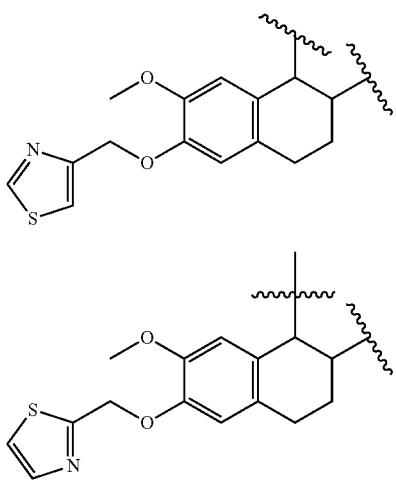

E37

E38

-continued

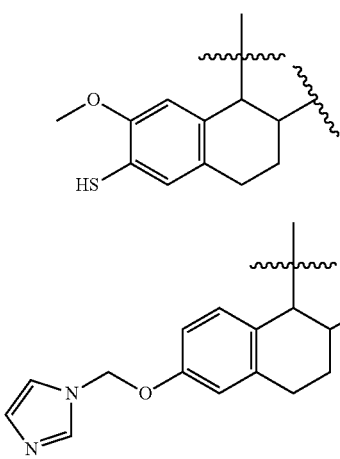

E39

E40

TABLE 9

Estrogen derivatives

| | |
|---|---|
| E1 | 3-(1H-imidazol-1-yl)-17-(1H-benzimidazol-1-yl)-estra-1,3,5-(10)-trien |
| E2 | 3-(1H-benzimidazol-1-yl)-17-(1H-benzimidazol-1-yl)-estra-1,3,5-(10)-trien |
| E3 | 3-(nitrile)-17-(1H-benzimidazol-1-yl)-estra-1,3,5-(10)-trien |
| E4 | 3-(1H-tetrazol-5-yl)-17-(1H-benzimidazol-1-yl)-estra-1,3,5-(10)-trien |
| VNPP341 (E5) | 3-(carboxylic acid)-17-(1H-benzimidazol-1-yl)-estra-1,3,5-(10)-trien |
| VNPP334 (E6) | 3-(methylcarboxylate)-17-(1H-benzimidazol-1-yl)-estra-1,3,5-(10)-trien |
| E7 | 3-(ethylcarboxylate)-17-(1H-benzimidazol-1-yl)-estra-1,3,5-(10)-trien |
| E8 | 3-(1H-imidazol-1-carboxylate)-17-(1H-benzimidazol-1-yl)-estra-1,3,5-(10)-trien |
| E9 | 3-(1H-imidazol-1-carbothioate)-17-(1H-benzimidazol-1-yl)-estra-1,3,5-(10)-trien |
| E10 | 3-(1H-benzimidazol-1-carboxylate)-17-(1H-benzimidazol-1-yl)-estra-1,3,5-(10)-trien |
| E11 | 3-(1H-benzimidazol-1-carbothioate)-17-(1H-benzimidazol-1-yl)-estra-1,3,5-(10)-trien |
| E12 | 3-(pyridine-2-ylmethoxy)-17-(1H-benzimidazol-1-yl)-estra-1,3,5-(10)-trien |
| E13 | 3-(pyridine-3-ylmethoxy)-17-(1H-benzimidazol-1-yl)-estra-1,3,5-(10)-trien |
| E14 | 3-(pyridine-4-ylmethoxy)-17-(1H-benzimidazol-1-yl)-estra-1,3,5-(10)-trien |
| E15 | 3-(thiazol-5-ylmethoxy)-17-(1H-benzimidazol-1-yl)-estra-1,3,5-(10)-trien |
| E16 | 3-(thiazol-4-ylmethoxy)-17-(1H-benzimidazol-1-yl)-estra-1,3,5-(10)-trien |
| E17 | 3-(thiazol-2-ylmethoxy)-17-(1H-benzimidazol-1-yl)-estra-1,3,5-(10)-trien |
| E18 | 3-(thiol)-17-(1H-benzimidazol-1-yl)-estra-1,3,5-(10)-trien |
| VNPP405 (E19) | 2-(methoxy)-3-(hydroxy)-17-(1H-benzimidazol-1-yl)-estra-1,3,5-(10)-trien |
| E20 | 2-(methylthio)-3-(hydroxy)-17-(1H-benzimidazol-1-yl)-estra-1,3,5-(10)-trien |
| VNPP338 (E21) | 3-(hydroxy)-17-(1H-benzimidazol-1-yl)-estra-1,3,5-(10)-trien |
| E22 | 2-(methoxy)-3-(carboxylic acid)-17-(1H-benzimidazol-1-yl)-estra-1,3,5-(10)-trien |
| E23 | 2-(methoxy)-3-(methylcarboxylate)-17-(1H-benzimidazol-1-yl)-estra-1,3,5-(10)-trien |
| E24 | 2-(methoxy)-3-(1H-imidazol-1-yl)-17-(1H-benzimidazol-1-yl)-estra-1,3,5-(10)-trien |
| E25 | 2-(methoxy)-3-(1H-benzimidazol-1-yl)-17-(1H-benzimidazol-1-yl)-estra-1,3,5-(10)-trien |
| E26 | 2-(methoxy)-3-(nitrile)-17-(1H-benzimidazol-1-yl)-estra-1,3,5-(10)-trien |
| E27 | 2-(methoxy)-3-(1H-tetrazol-5-yl)-17-(1H-benzimidazol-1-yl)-estra-1,3,5-(10)-trien |
| E28 | 2-(methoxy)-3-(ethylcarboxylate)-17-(1H-benzimidazol-1-yl)-estra-1,3,5-(10)-trien |
| E29 | 2-(methoxy)-3-(1H-imidazol-1-carboxylate)-17-(1H-benzimidazol-1-yl)-estra-1,3,5-(10)-trien |
| E30 | 2-(methoxy)-3-(1H-imidazol-1-carbothioate)-17-(1H-benzimidazol-1-yl)-estra-1,3,5-(10)-trien |
| E31 | 2-(methoxy)-3-(1H-benzimidazol-1-carboxylate)-17-(1H-benzimidazol-1-yl)-estra-1,3,5-(10)-trien |
| E32 | 2-(methoxy)-3-(1H-benzimidazol-1-carbothioate)-17-(1H-benzimidazol-1-yl)-estra-1,3,5-(10)-trien |

TABLE 9-continued

Estrogen derivatives

| | |
|---|---|
| E33 | 2-(methoxy)-3-(pyridine-2-ylmethoxy)-17-(1H-benzimidazol-1-yl)-estra-1,3,5-(10)-trien |
| E34 | 2-(methoxy)-3-(pyridine-3-ylmethoxy)-17-(1H-benzimidazol-1-yl)-estra-1,3,5-(10)-trien |
| E35 | 2-(methoxy)-3-(pyridine-4-ylmethoxy)-17-(1H-benzimidazol-1-yl)-estra-1,3,5-(10)-trien |
| E36 | 2-(methoxy)-3-(thiazol-5-ylmethoxy)-17-(1H-benzimidazol-1-yl)-estra-1,3,5-(10)-trien |
| E37 | 2-(methoxy)-3-(thiazol-4-ylmethoxy)-17-(1H-benzimidazol-1-yl)-estra-1,3,5-(10)-trien |
| E38 | 2-(methoxy)-3-(thiazol-2-ylmethoxy)-17-(1H-benzimidazol-1-yl)-estra-1,3,5-(10)-trien |
| E39 | 2-(methoxy)-3-(thiol)-17-(1H-benzimidazol-1-yl)-estra-1,3,5-(10)-trien |
| E40 | 3-(imidazol-1-ylmethoxy)-17-(1H-benzimidazol-1-yl)-estra-1,3,5-(10)-trien |

EXPERIMENTAL SECTION

General:

All chemicals and reagents were commercially obtained from Aldrich or Acros chemicals except 6-hydroxynaphthyl-2-boronicacidacid (Alfa Aesar) and are used directly without purification. Reaction progress was determined by TLC analysis on Silica gel plates (Merck F254). Flash Column chromatography (FCC) was performed using silica gel (230-400 mesh, 60 Å). Melting points (mp) were determined with a Stuart SMP10 melting point apparatus and are uncorrected. IR spectra were recorded neat on a Perkin Elmer spectrum65 FT IR spectrometer and are reported as $\lambda$max $(cm^{-1})$. $^1$H NMR spectra were recorded on a Bruker DMX 500 MHz or Bruker Ascend 400 MHz spectrometer using $CDCl_3$ or DMSO-$d_6$ as solvent. Chemical shifts are given in parts per million (ppm), and TMS was used as an internal standard. $^{13}$C NMR spectra were recorded Bruker DMX 500 MHz or Bruker 400 MHz spectrometer operating at 125 or 100 MHz respectively.

Chemistry:

The syntheses of all compounds in this study were accomplished by following methods and conditions as depicted in Scheme 1-8. The key intermediate N-alkylated benzimidazoles (VNPP319C and VNPP346) for the synthesis biphenyl derivatives were prepared by reacting benzimidazole with appropriate arylalkylbromide, in presence KOH in dry DMSO with excellent yield (Method A1, Scheme 1).[26] Where, N-arylated bezimidazole (VNPP371/1, VNPP423 and VNPP442) were obtained in moderate yield by applying reported method of 'ligated catalysis' for the Ullmann condenstation (Method A2, Scheme 1).[27] In which, benzimidazole is reacted with substituted 3-iodobenzenes in presence of mild alkali (cesium carbonate), catalyst (copper iodide) and a ligate (1,10-phenantroline) in DMF at 110° C. for 40 h. These alkyl/arylated benzimidazoles were reacted with corresponding substituted boronic acids via Suzuki coupling to form desired biaryl (VNPP347B(B1), VNPP358(B2), VNPP356(B3), VNPP360(B7), VNPP321(B18), VNPP355(B19), VBPP357(B20), VNPP444B(B23), VNPP441C(B24), VNPP420(B25), VNPP359, VNPP372/2(Na1)—VNPP373/2(Na2)) compounds (Method B, Scheme 1).[23] Further 1,3-diploar cycloaddition of sodium azide with nitrile biphenyls (VNPP358 & 357) in presence of ammonium chloride in polar high-boiling solvent such as DMF afforded excellent yield of respective tetrazole compounds (VNPP361(B11) and VNPP364; Method C, Scheme 1).[25]

Synthesis of stilbene derivative with mainly (E)-configuration (VNPP388(S1) and VNPP391B3(S2)) are achieved with moderate yield, in essence, as described in recent report (Scheme 2).[28] Thus, reaction of aldehyde with methyltriphenylphosphonium bromide in the presence of t-BuOK in a Wittig method provided the intermediate styrene (VNPP383). Its Mizoroki-Heck reaction with bromoaryl benzimidazole (VNPP371/1) in triethanolamine as a base/ligand/solvent in presence of catalytic amount of $Pd(OAc)_2$ at 100° C. for 24 h provided stilbene (VNPP388(S1)) in good yield. Similarly compound VNPP390(S2) is synthesized from commercially available p-methoxyphenylstyrene.

Diaryl compounds with alkylamines (VNPP428(Am-a1), VNPP429(Am-a2)), amide (VNPP432(Amd-b2)) and sulfonamide (VNPP431(SulAmd-1)) linker compounds were synthesized using arylated BzIm intermediate 1-(3-aminophenyl-1H-benzo[d]imidazole (VNPP423) compound (Scheme 3). The intermediate VNPP423 was synthesized using 3-iodoaniline by following (Method-A2) procedure for intermediate VNPP371.[27] Alkylamine (VNPP428(Am-a1)-VNPP429(Am-a2))compounds were obtained via imines (not isolated) by refluxing VNPP423 with corresponding aldehyde in ethanol in presence of molecular sieves and further reducing imines with sodium borohyderide in methanol at ice cold temperature (34% and 50% respectively).[25] The amide derivative VNPP432(Amd-b2) is obtained by the reaction of 4-methoxybenzoyl chloride on VNPP423in presence TEA in ethyl acetate at room temperature (49%). Where sulfonamide derivative VNPP431(SulAmd-1) is achieved by refluxing VNPP423 with 4-methoxybenzenesulfonyl chloride in pyridine (48%).[25]

For the synthesis of C3 imidazole derivatives of VN/124-1, initially mesyl derivative of VN/124-1 (VNPT88) prepared (Scheme 4) which on refluxing with imidazole in toluene under anhydrous condition resulted in three imidazole substituted compounds (VNPP433-6 (35%), VNPP433-3α(A3) (3%) and VNPP433-3β(2d)(A1) (11%)). These three positional isomers were separated by preparative HPLC method. The thiocarbamate derivative VNPP397(A5) is accomplished by slightly modifying our reported synthetic method of (Scheme 5) imidazolecarbamate derivative of VN/124-1.[17] Thus VN/124-1 is refluxed with 1,1'-thiocarbonyldiimidazole in acetonitrile and MDC solvent mixture. The C3 ether derivatives (VNPP415C(A15), VNPP414 (A16) and VNPP412(A31)) of VN/124-1 were prepared by following williamson's etherfication (Scheme 6) method of treating alcohol (VN/124-1) with arylalkyl/alkyl halide in presence of sodium hydride as base in DMF.

The synthesis of 17-bezoazole of estrone-3-carboxlate (VNPP341(E5)) and estrone (VNPP338(E21)) derivatives is outlined in scheme 7 and 8, respectively. For the synthesis of estrone-3-carboxylate derivative (VNPP341(E5), initially 3-enol carbon of estrone is activated by converting it in to triflate (VNPP308) by reacting with triflic anhydride in presence of organic base (TEA).[29] Then triflate is replaced with methyl carboxylate through palladium-catalyzed carbonylation using $Pd(OAc)_2$ as catalyst, 1,c-bis(diphenylphospheno)propane as the phosphine ligand, in presence of gaseous carbon monoxide, methanol in DMF (VNPP309A).[30] The synthesis of title compound 17-1H-bezimidazolyl derivative (VNPP341(E5) of this estrone-3-carboxylate, is accomplished by following our routine method for the synthesis of VN/124-1 as shown in Scheme 7.[17] Which follows three intermediate steps viz formation of 16-formyl-17-bromo derivative (VNPP315B) through vilsmeier-hack reaction, condensation of bezimidazole ring to C-17 position (VNPP330), then Pd catalyzed 16-deformylation (VNPP334(E6)) and finally basic hydrolysis of methyl ester group to obtain target compound VNPP341(E5).

The synthesis of estrone-3-hydroxy-17-1H-bezoazole (VNPP334(E21)) derivative initiated with 3-acetylation of commercially available estrone (Scheme 8) with acetic anhydride in pyridine with 98% of isolated yield (VNPP310). Then it is subjected to vilsmeier-hack reaction to obtain 16-formy-17-bromo derivative (VNPP311) by treating with phosphorus tribromide in DMF and chloroform with low yield. An attempt to condensation of benzimidazole to $17^{th}$ position of VNPP311 by following our routine $K_2CO_3$ in DMF method resulted into mixture of four components (partial 3-deacetylation with or without benzimidazole substitution, acetylated benzimidazole product and substrate). Therefore, first the 3-acetyl group of VNPP311 was hydrolyzed by treating with10% ethanolic-KOH to obtain VNPP312, then benzimidazole group condensed using $K_2CO_3$ in DMF (VNPP314) and finally 16-deformylation by refluxing with 10% Pd/C in benzonitrile to obtain final compound (VNPP338(E21)) with very low isolated yield in the final step (6%).

Scheme 1[a]: Synthesis of biphenyl (B series) and naphthyl derivative (Na series)

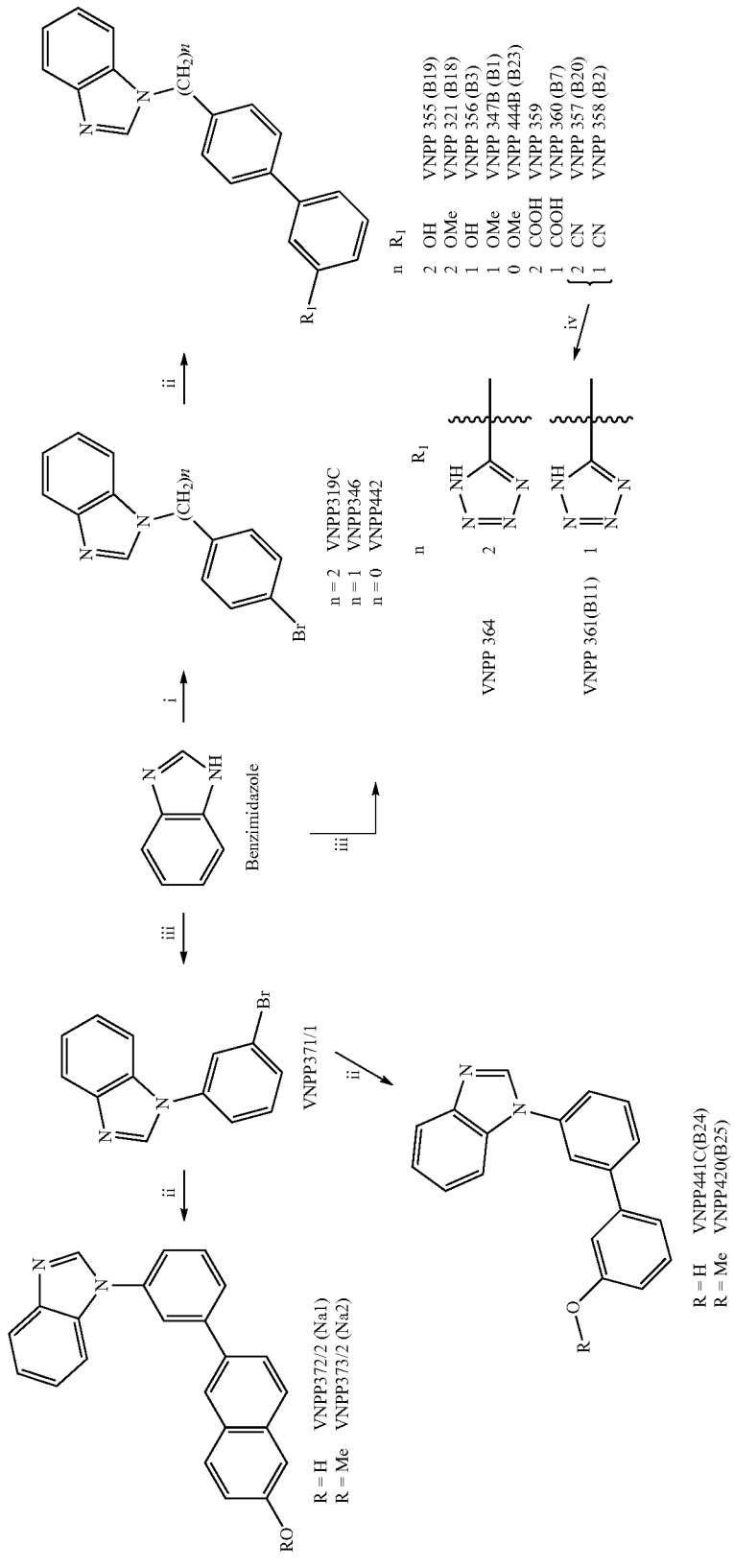

[a]Reagents and conditions: [a]Reagents and Conditions: (i) KOH, DMSO, rt, 2 h, 4-bromobenzyl bromide/4-bromophenylethyl bromide; rt, 24 h (ii) Method A: Pd(OAc)$_2$, corresponding boronic acid, Na$_2$CO$_3$, TBAB, Ar, toluene, H$_2$O, ethanol, reflux, 2-6 h; (iii) 3/4-bromoiodobenzene, CuI, 1,10-phenanthroline, Cs$_2$CO$_3$, DMF, 110° C., 40 h; (iv) NH$_4$Cl, NaN$_3$, DMF, 120° C., 20 h.

Scheme 2$^b$: Synthesis of stilbene derivative (S series)

Scheme 4$^d$: Synthesis of C3 imidazole derivative of VN/124-1 (A series)

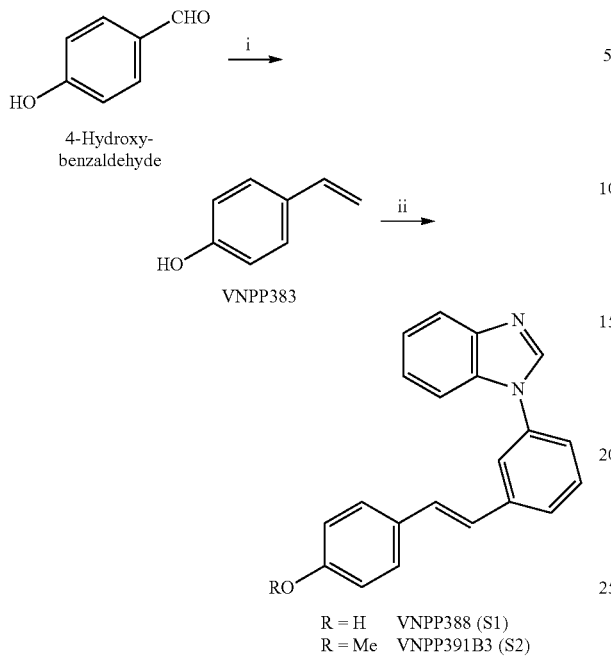

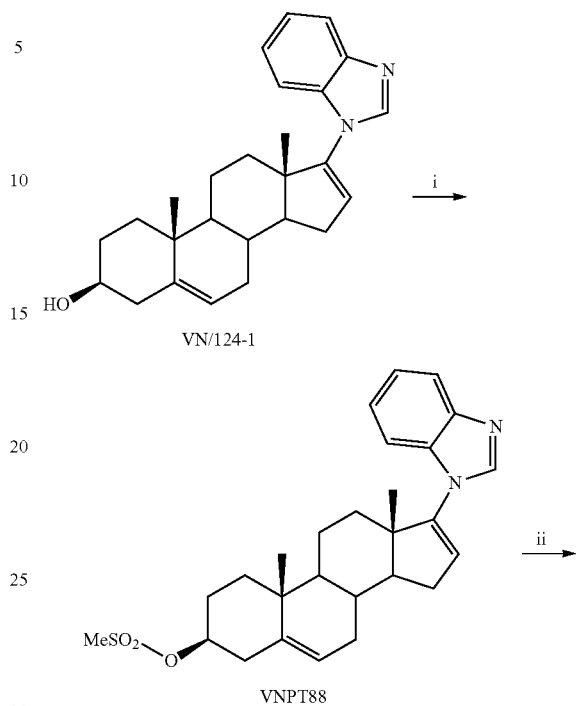

$^b$Reagents and conditions: (i) MeP(C$_6$H$_5$)$_3$Br, t-BuOK, THF, 24 h, 25° C.;
(ii) VNPP371/1, triethanolamine, Pd(OAc)$_2$, 24 h, 100° C.

Scheme 3$^c$: Synthesis of amine (Am-a series), amide (Amd-b series) and sulphonamide (SulAmd series) derivatives

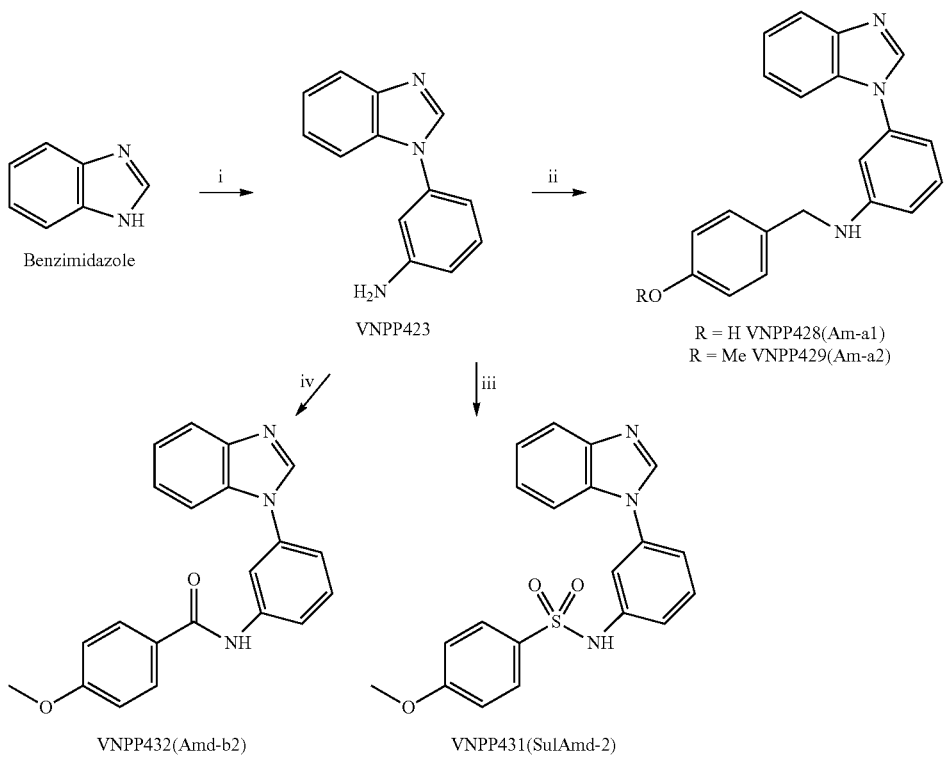

$^c$Reagents and Conditions: (i) 3-Iodoaniline, CuI, 1,10-phenanthroline, Cs$_2$CO$_3$, DMF, 110° C., 40 h; (ii) 4-hydroxy/methoxybenzaldehyde, Ethanol, molecular sieves, reflux, overnight, evaporate, MeOH, NaBH4, 0° C., 1 h; (iii) 4-methoxybenzensulfonyl chloride, pyridine, 125° C., 24 h; (iv) 4-methoxybenzoyl chloride, TEA, EtOAc, rt, 5 h -continued
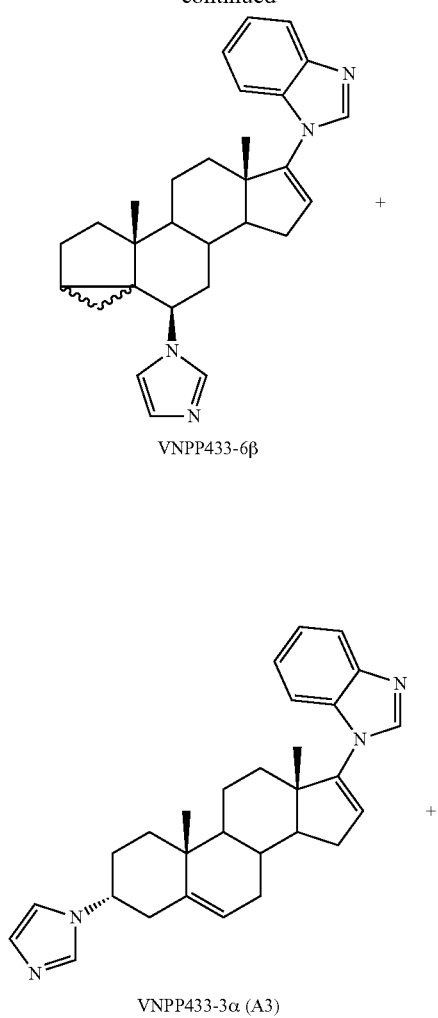
VNPP433-6β
VNPP433-3α (A3)
VNPP433-3β (A2)
[d]Reagents and conditions: (i) Mesyl chloride, Pyridine, ice cold (ii) Imidazole, toluene, reflux, 12 h
Scheme 5[e]: Synthesis of imidazolethiocabamate derivative of VN/124-1 (A series)
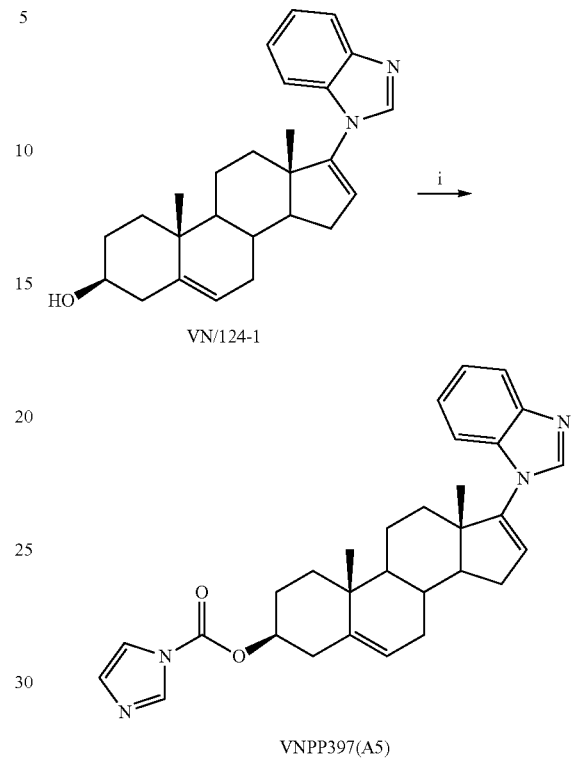
VN/124-1
VNPP397(A5)
[e]Reagents and conditions: (i) 1,1′-thiocarbonyldiimidazole, CH₃CN, MDC, reflux, 5 h
Scheme 6[f]: Synthesis of C3 ether derivative of VN/124-1 (A series)
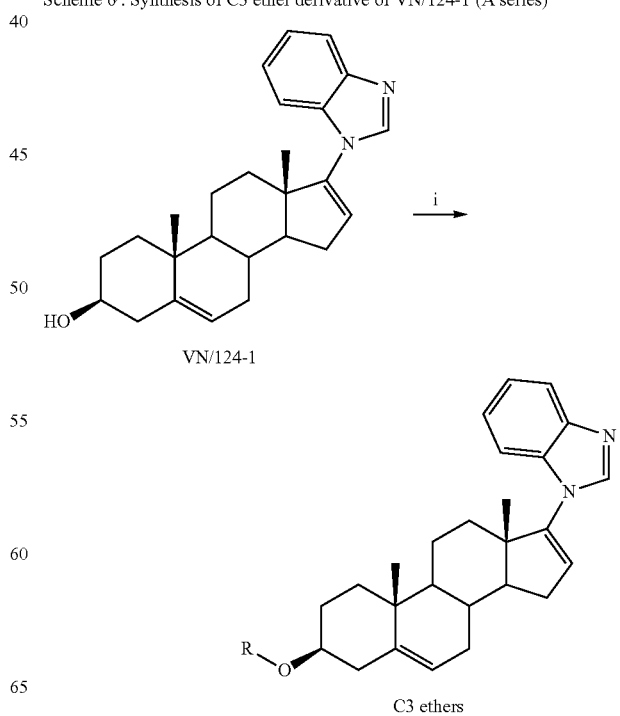
VN/124-1
C3 ethers

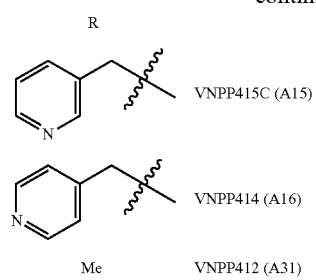

*f*Reagents and conditions: (i) arylalkyl/alkyl halides, NaH, DMF, 30-65° C., 1-12 h Scheme 7*g*: Synthesis of estrone-3-carboxylate derivative (E series)

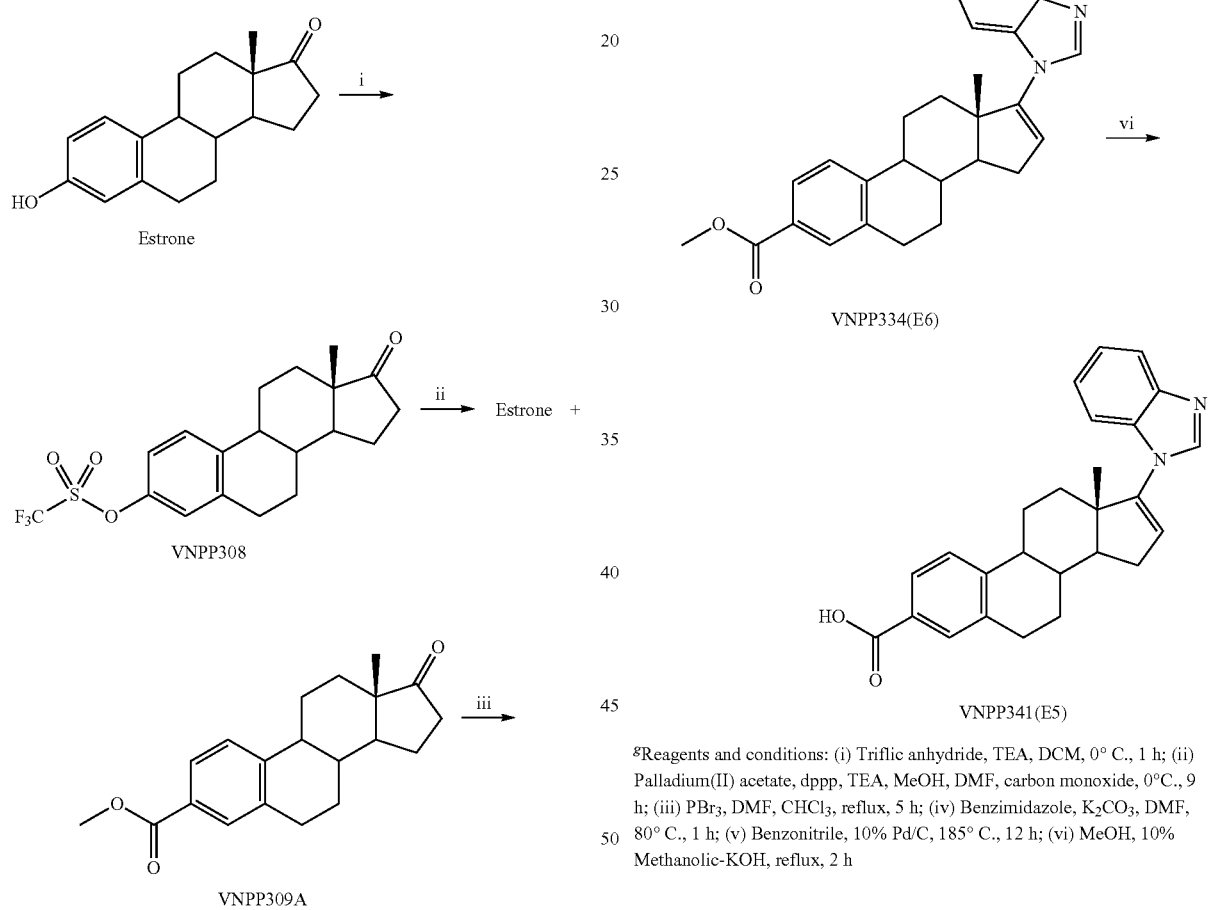

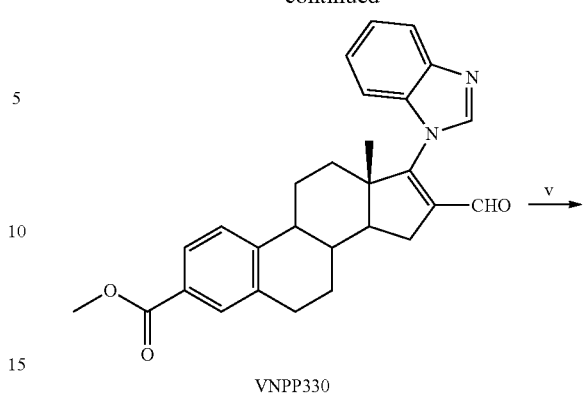

*g*Reagents and conditions: (i) Triflic anhydride, TEA, DCM, 0° C., 1 h; (ii) Palladium(II) acetate, dppp, TEA, MeOH, DMF, carbon monoxide, 0°C., 9 h; (iii) PBr$_3$, DMF, CHCl$_3$, reflux, 5 h; (iv) Benzimidazole, K$_2$CO$_3$, DMF, 80° C., 1 h; (v) Benzonitrile, 10% Pd/C, 185° C., 12 h; (vi) MeOH, 10% Methanolic-KOH, reflux, 2 h Scheme 8*h*: Synthesis of estrone-3-hydroxy derivative

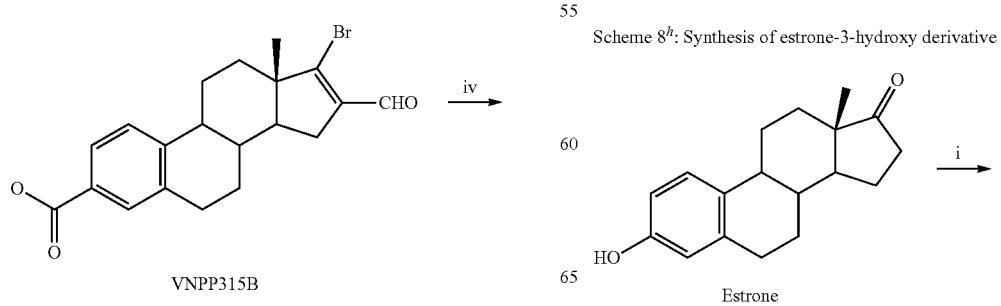

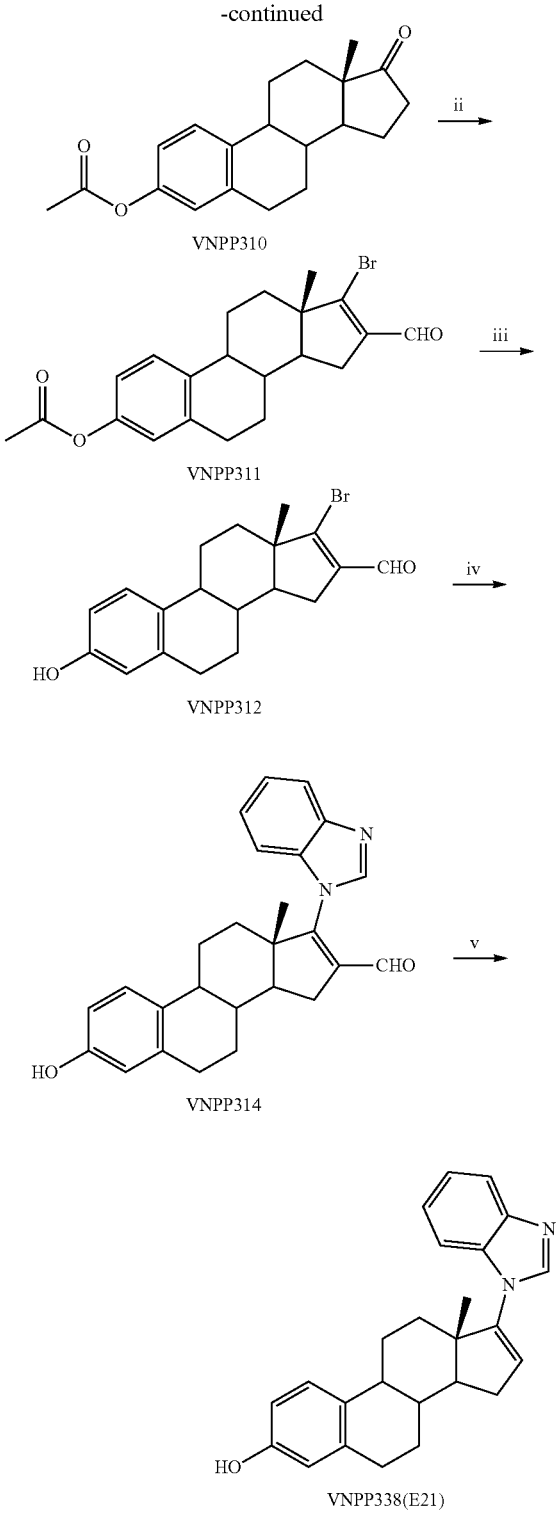

[d]Reagents and conditions: (i) Pyridine, acetic, anhydride, rt, 12 h; (ii) PBr₃, DMF, CHCl₃, reflux, 5 h; (iii) EtOH, 10% Ethanolic-KOH, rt, 12 h; (iv) Benzimidazole, K₂CO₃, DMF, 80° C., 5 h; (vi) Benzonitrile, 10% Pd/C, 185° C., 12 h;

General Methods for Synthesis:
Method A1: N-alkylation of Benzimidazole (VNPP319C and VNPP346).

DMSO (10 mL, dried over molecular sieves) was added to KOH (0.95 g, 16.96 mmol, crushed pallets) and the mixture was stirred for 5 min. Benzimidazole (0.5 g, 4.23 mmol) was then added and stirred at room temperature for 2 h prior to the addition of corresponding 4-bomophenylakyl bromide (8.46 mmol). Reaction mixture stirred for 24 h, poured on to ice-water mixture, filtered, dried and purified by FCC Method A2: Arylation of Benzimidazole (Compound VNPP442, VNPP371/1 and VNPP423)

A mixture of benzimidazole (1 equiv), corresponding substituted iodobenzene (1.2 equiv), copper iodide (0.01 equiv), 1,10-phenanthroline (0.2 equiv) and cesium carbonate (2 equiv) in DMF was heated to 110° C. for 40 h. The reaction mixture was cooled to room temperature and the solvent was evaporated under vacuum. Residue stirred with water and EtOAc, filtered, organic layer separated, dried (Na₂SO₄) and the solvent removed under vacuum. Crude product was purified by FCC using gradient solvent [petroleum ether/EtOAc (8:2) then (1:1) and traces of TEA].

Method B: Suzuki Coupling.

The corresponding brominated aromatic compound (1 equiv) was dissolved in toluene (7 mL/mmol), and to this an aqueous 2.0 M Na₂CO₃ solution (3.2 mL/mmol), corresponding boronic acid (1.5-2 equiv), ethanol (3.2 mL/mmol of boronic acid) and tetrabutylammonium bromide (1 equiv) were added. The mixture was deoxygenated under vacuum and flushed with argon. After this cycle was repeated five times, Pd(OAc)₂ (5 mol %) was added and the resulting suspension was refluxed for 2-6 h. Reaction mixture cooled, EtOAc (10 mL) and water (10 mL) were added and the organic phase was separated. The water phase was extracted with EtOAc (2×10 mL). The combined organic phases were washed with brine, dried over Na₂SO₄, filtered over a short plug of Celite, and evaporated under vacuum. The compounds were purified by FCC on 5 inch silica gel column using petroleum ether/EtOAc (1:1) to remove nonpolar contaminations then with 2% methanol in DCM. Most of biphenyls were synthesized, isolated and purified by this method unless otherwise mentioned.

Method C: Conversion of Nitrile to Tetrazole.

A mixture of corresponding nitrile compound (1 equiv), sodium azide (12.5 equiv) and ammonium chloride (12.5 equiv) in DMF was heated at 120° C. for 20 h. The reaction mixture was poured into ice cold water (30 mL) and acidified with dilute HCl solution. The white precipitate obtained on acidification was filtered; dried and aqueous phase was extracted with EtOAc, dried with Na₂SO₄ and evaporated. Crude solid and crude product obtained by EtOAc extraction were combined, purified by FCC over a short column [10% methanol in DCM] to give pure tetrazole derivative.

Method D: Amine Derivatives (VNPP428(am-A1), VNPP429(am-a2))

A mixture of amine VNPP423 (1 equiv), corresponding aldehyde (1 equiv), and molecular sieves in ethanol refluxed overnight. Then solvent evaporated, reconstituted with methanol and NaBH₄ (2 equiv) added at ice cold temperature and stirred for 1 hr. Reaction mixture filtered and then purified by FCC [petroleum ether/EtOAc/TEA (3:2:0.01)].

Experimental

1-(4-bromophenethyl)-1H-benzo[d]imidazole (VNPP319C)

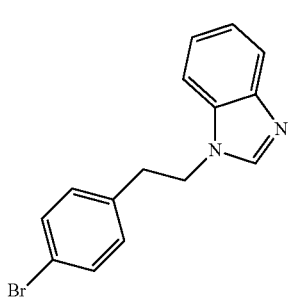 [SMILES: Brc1ccc(CCn2cnc3ccccc32)cc1]

Method A1: using KOH (0.95 g, 16.96 mmol), DMSO (10 ml) benzimidazole (0.5 g, 4.23 mmol) and 4-bomophenyl-ethyl bromide (2.23 g, 8.46 mmol). Crude product was purified by FCC using short column [2% methanol in DCM] to give VNPP319C (1.05 g, 82.7%): mp 124-126° C.; IR (Neat) 1610, 1500, 1486, 1456, 1242, 1168, 1069, 1008, 805, 747 cm$^{-1}$; $^1$H NMR (500 MHz, CDCl$_3$) δ 3.10 (t, J=6.94 Hz, 2 H, CH$_2$), 4.38 (t, J=6.87 Hz, 2 H, =N—CH$_2$), 6.86 (d, J=8.09 Hz, 2 H, Ar-$2^2$ and $6^2$ Hs), 7.27-7.34 (m, 2 H, Ar-$5^1$ and $6^1$ Hs), 7.35-7.41 (comp, 3 H, Ar-$7^1$, $3^2$ and $5^2$ Hs), 7.58 (s, 1 H, Ar-$2^1$ H), 7.77-7.85 (dd, J=6.65, 1.75 Hz, 1 H, Ar-$4^1$ H); $^{13}$C NMR (101 MHz, CDCl$_3$) δ 35.6, 46.4, 109.4, 120.6, 121.0, 122.2, 123.0, 130.3 (2×C), 131.9 (2×C), 133.4, 136.4, 142.9, 143.9

1-(4-bromobenzyl)-1H-benzo[d]imidazole (VNPP346)

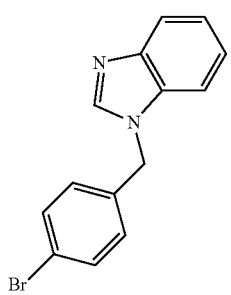 [SMILES: Brc1ccc(Cn2cnc3ccccc32)cc1]

Method A1: using KOH (0.95 g, 17 mmol), DMSO (10 ml), benzimidazole (0.5 g, 4.23 mmol) and 4-bomobenzyl bromide (2.11 g, 8.46 mmol). Crude product was purified by FCC using short column [6% EtOAc in petroleum ether and then 20%] to give VNPP346 (1.0 g, 82.6%): mp 87-91° C.; IR (Neat) 1591, 1617, 1488, 1468, 1364, 1285, 1260, 1205, 1172, 1099, 739 cm$^{-1}$; $^1$H NMR (500 MHz, CDCl$_3$) δ 5.32 (s, 2 H, CH$_2$), 7.05 (d, 2 H, J=8.24 Hz, Ar-$2^2$ and $6^2$ Hs), 7.24-7.27 (comp, 3 H, Ar-$5^1$, $6^1$ and $7^1$-Hs), 7.47 (d, 2 H, J=8.39 Hz, Ar-$3^2$, $5^2$ Hs), 7.83 (d, 1 H, J=7.48 Hz, Ar-$4^1$ H), 7.95 (s, 1 H, Ar-$2^1$ H); $^{13}$C NMR (101 MHz, CDCl$_3$) δ 110.2, 120.8, 122.5, 123.1, 123.5, 124.0, 127.0, 131.0, 131.3, 133.3, 137.5, 141.9, 144.0

1-(4-bromophenyl)-1H-benzo[d]imidazole (VNPP442)

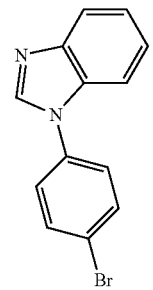 [SMILES: Brc1ccc(-n2cnc3ccccc32)cc1]

Method A2: using 3-bromoiodobenzene. Yield 14%: mp 100-1° C.; $^1$H NMR (400 MHz, CDCl$_3$) δ 7.33-7.37 (m, 2 H, Ar-$5^1$ and $6^1$ Hs), 7.39-7.44 (d, 2 H, Ar-$2^2$, $6^2$ Hs), 7.48-7.56 (m, 1 H, Ar-$7^1$), 7.69-7.74 (d, 2 H, Ar-$3^2$, $5^2$Hs), 7.86-7.91 (m, 1 H, Ar-$4^1$), 8.08 (s, 1 H, Ar-$2^1$); $^{13}$C NMR (500 MHz, CDCl$_3$) δ 144.11, 141.98, 135.41, 133.48, 133.27, 125.55, 123.97, 123.05, 121.66, 120.81, 110.22

1-(3-bromophenyl)-1H-benzo[d]imidazole (VNPP371/1)

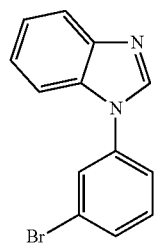 [SMILES: Brc1cccc(-n2cnc3ccccc32)c1]

Method A2 using 3-bromoiodobenzene. Yield 60.8%: mp 77-79° C.; $^1$H NMR (500 MHz, DMSO-d$_6$) δ 7.34 (quin, J=7.40 Hz×4, 2 H, Ar-$5^1$ and $6^1$Hs), 7.56-7.62 (m, 1 H, $5^2$ H), 7.64 (d, J=7.48 Hz, 1 H Ar-$6^2$ H), 7.71 (d, J=8.09 Hz, 1 H, Ar-$7^1$ H), 7.74 (d, J=7.93 Hz, 1 H, Ar-$4^2$ H), 7.79 (d, J=7.48 Hz, 1 H Ar-$4^1$ H), 7.96 (s, 1 H, Ar-$2^1$ H), 8.60 (s, 1 H, Ar-$2^2$ H); $^{13}$C NMR (500 MHz, CDCl$_3$) δ 144.2, 142.1, 137.7, 133.5, 131.5, 131.3, 127.2, 124.2, 123.7, 123.3, 122.7, 120.9, 110.4

1-(3-aminophenyl)-1H-benzo[d]imidazole (VNPP423)

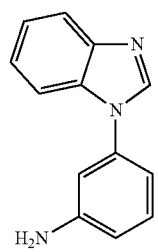 [SMILES: Nc1cccc(-n2cnc3ccccc32)c1]

Method A2: using 3-iodoniline. Yield 78%: mp 137-38° C.; $^1$H NMR (400 MHz, CDCl$_3$) δ 3.94 (br. s., 2 H, NH$_2$), 6.72-6.77 (m, 1 H, Ar-5$^2$ H), 6.78 (s, 1 H, Ar-2$^2$ H), 6.87 (d, J=7.34 Hz, 1 H, Ar-4$^2$ H), 7.27-7.40 (m, 3 H, Ar-6$^2$, 5$^1$ and 6$^1$ Hs), 7.54-7.63 (m, 1 H, Ar-4$^1$), 7.81-7.92 (m, 1 H, Ar-7$^1$ H), 8.09 (s, 1 H, Ar-2$^1$ H); $^{13}$C NMR (500 MHz, CDCl$_3$) δ 148.0, 142.3, 137.3, 133.6, 130.8, 123.5, 122.6, 120.5, 114.4, 113.7, 110.7, 110.1

3-[4-(benzimidazolylmethyl)phenyl]-1-methoxybenzene (VNPP347B (B1))

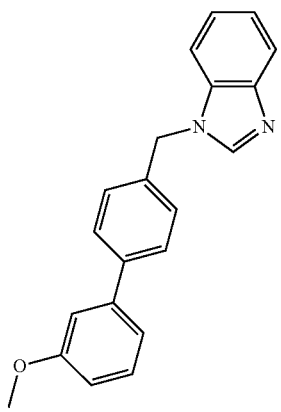 [SMILES: COc1cccc(-c2ccc(Cn3cnc4ccccc43)cc2)c1]

Method B: using VNPP346 (0.3 g, 1.05 mmol) and 3-methoxyphenylboronic acid (0.24 g, 1.57 mmol). Yield (0.31 g, 94%): mp 132-133° C.; IR (Neat2960, 1607, 1584, 1567, 1482, 1437, 1296, 1208, 1174, 1058, 1014, 839, 777 cm$^{-1}$; $^1$H NMR (500 MHz, CDCl3) δ 3.87 (s, 3 H, CH$_3$), 5.43 (s, 2 H, CH$_2$), 6.92 (dd, J=8.24, 1.98 Hz, 1 H, Ar-4$^3$ H), 7.09 (s, 1 H, Ar-2$^3$ H), 7.15 (d, J=7.78 Hz, 1 H, Ar-6$^3$ H), 7.25-7.28 (m, 2 H, Ar-5$^1$ and 6$^1$ Hs), 7.28-7.32 (m, 2 H, Ar-2$^2$ and 6$^2$ Hs), 7.32-7.39 (m, 2 H, Ar-5$^3$ and 7$^1$ Hs), 7.57 (d, J=8.09 Hz, 2 H, Ar-3$^2$ and 5$^2$ H), 7.86 (d, J=7.78 Hz, 1 H, Ar-4$^1$ H), 8.01 (s, 1 H, Ar-2$^1$-H); $^{13}$C NMR (500 MHz, CDCl$_3$) δ 160.2, 144.1, 143.4, 142.0, 141.3 134.7, 134.1, 130.0, 127.9 (2×C), 127.7 (2×C), 123.3, 122.5, 120.6, 119.7, 113.1, 113.0, 110.3, 55.5, 48.7

3-[4-(benzimidazolylmethyl)phenyl]benzenecarbonitrile (VNPP358 (B2))

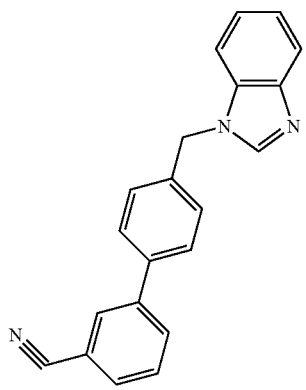 [SMILES: N#Cc1cccc(-c2ccc(Cn3cnc4ccccc43)cc2)c1]

Method B: using VNPP346 (0.19 g, 0.66 mmol) and 3-nitrilephenylboronic acid (0.15 g, 1 mmol). Yield (0.18 g, 86.7%): mp 133-135° C.; IR (Neat) 2230, 1491, 1458, 1368, 1286, 1260, 1183, 796 cm$^{-1}$; $^1$H NMR (500 MHz, D$_{MS}$O-d$_6$) δ 5.57 (s, 2 H, CH$_2$), 7.17-7.25 (m, 2 H, Ar-5$^1$ and 6$^1$ Hs), 7.43 (m, J=8.24 Hz, 2 H, Ar-2$^2$ and 6$^2$ Hs), 7.54-7.59 (m, 1 H, Ar-7$^1$ H), 7.65 (m, 2 H, Ar-4$^1$ and 5$^3$ H), 7.72 (m, 2 H, Ar-3$^2$ and 5$^2$ Hs), 7.81 (d, J=7.78 Hz, 1 H, Ar-6$^3$ H), 7.99 (d, J=8.70 Hz, 1 H, Ar-64H), 8.12 (s, 1 H, Ar-2$^2$ H), 8.46 (s, 1 H, Ar-2$^3$ H); $^{13}$C NMR (500 MHz, CDCl$_3$) δ 144.1, 143.5, 141.7, 139.0, 136.0, 134.0, 131.6, 131.1, 130.8, 129.9, 128.0, 127.9, 123.5, 122.6, 120.7, 118.9, 113.2, 110.2, 48.6

3-[4-(benzimidazolylmethyl)phenyl]phenol (VNPP356 (B3))

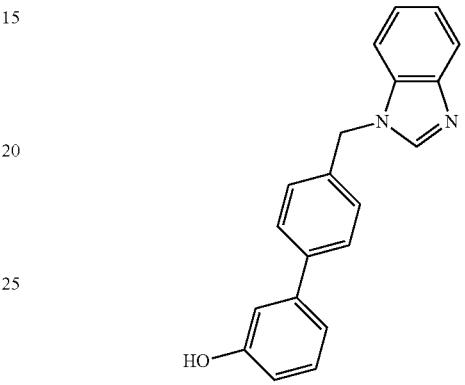

Method B: using VPNN346 (0.20 g, 0.7 mmol) and 3-hydroxyphenylboronic acid (0.15 g, 1.08 mmol). Yield (0.14 g, 65.7%): mp 231-232° C.; IR (Neat) 3103, 1582, 1567, 1504, 1476, 1364, 1305, 1219, 1196, 830, 777cm$^{-1}$; $^1$H NMR (500 MHz, DMSO-d$_6$) δ 5.54 (br. s., 2H, CH$_2$), 6.77 (d, J=7.32 Hz, 1 H, Ar-4$^3$ H), 7.00 (br. s., 1 H, Ar-2$^3$ H), 7.03 (d, J=7.48 Hz, 1 H, Ar-6$^3$ H), 7.22 (m, J=7.02 Hz, 3 H, Ar-5$^1$, 6$^1$ and 5$^3$Hs), 7.38 (d, J=7.48 Hz, 2 H, Ar-2$^2$ and 6$^2$ Hs), 7.57 (d, J=7.02 Hz, 3 H, Ar-3$^2$, 5$^2$ and 7$^1$ Hs), 7.69 (d, J=6.87 Hz, 1 H, Ar-4$^1$ H), 8.46 (s, 1 H, Ar-2$^1$ H), 9.56 (s, 1 H, —OH); $^{13}$C NMR (500 MHz, DMSO-d$_6$) δ 158.4, 144.9, 144.2, 141.7, 140.4, 136.7, 134.3, 130.5, 128.5 (2×C), 127.5 (2×C), 123.1, 122.2, 120.1, 118.0, 115.2, 114.1, 111.3, 47.9

3-[4-(benzimidazolylmethyl)phenyl]benzoic acid (VNPP360 (B7))

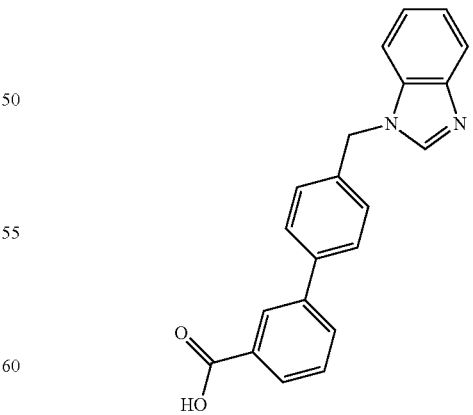

By slight modification of Method B: using VNPP346 (0.19 g, 0.66 mmol) and 3-carboxyphenylboronic acid (0.17 g, 1 mmol) and 2 M aq Na$_2$CO$_3$ (2×2.13 mL). After completion of reaction, reaction mixture neutralized with dil. HCl, extracted with EtOAc, filtered and concentrated.

On purification by FCC [petroleum ether/EtOAc (1:1) and then with 4% ethanol in DCM with traces of CH$_3$COOH] gave VNPP360 (0.03 g, 14%): mp 240-242° C.; IR (Neat) 3337, 1615, 1499, 1461, 1266, 1207, 806, 735 cm$^{-1}$ $^1$H NMR (500 MHz, DMSO-d$_6$) δ 5.57 (s, 2 H, CH$_2$), 7.21 (quind, J=7.17×4, 1.37 Hz, 2 H, Ar-5$^1$ and 6$^1$ Hs), 7.42 (d, J=8.24 Hz, 2 H, Ar-2$^2$ and 6$^2$ Hs), 7.52-7.58 (m, 2 H, Ar-4$^1$ and 7$^1$Hs), 7.67 (m, 3 H, Ar-5$^3$, 3$^2$ and 5$^2$ Hs), 7.84 (d, J=8.09 Hz, 1 H, Ar-6$^3$ H), 7.91 (d, J=7.78 Hz, 1H, Ar-4$^3$ H), 8.14 (s, 1 H, Ar-2$^1$ H), 8.45 (s, 1 H, Ar-2$^3$ H); $^{13}$C NMR (500 MHz, DMSO-d$_6$) δ 168.2, 144.2, 140.4, 139.4, 137.2, 134.3, 133.0, 131.2, 129.8, 129.0, 128.8, 128.7 (2×C), 128.0, 127.7 (2×C), 122.4, 122.1, 120.1, 111.3, 47.9

5-{3-[4-(benzimidazolylmethyl)phenyl]phenyl}-1H-1,2,3,4-tetraazole (VNPP361 (B11))

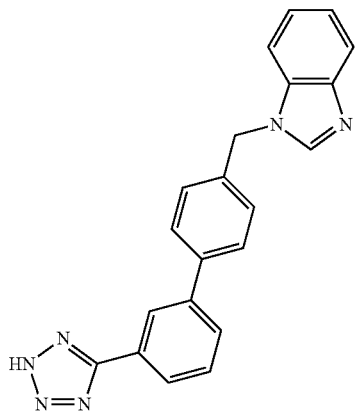 [SMILES: c1cc(-c2ccc(Cn3cnc4ccccc43)cc2)cc(-c2nn[nH]n2)c1]

Method C: using 0.85 g (0.274 mmol) of VNPP358. Yield (0.075 g, 77.4%): mp 231-233° C.; IR (Neat) 3337, 1615, 1499, 1461, 1266, 1207, 806, 735 cm$^{11}$ $^1$H NMR (500 MHz, DMSO-d$_6$) δ 5.59 (s, 2 H, CH$_2$), 7.22 (quin, J=7.13 Hz, 2 H, Ar-5$^1$ and 6$^1$ Hs), 7.45 (d, J=7.78 Hz, 2 H, Ar-2$^2$ and 2$^6$ Hs), 7.59 (d, J=6.71 Hz, 2 H, Ar-3$^2$ and 5$^2$ Hs), ), 7.68 (d, J=7.32 Hz, 1 H, Ar-6$^3$ H), 7.70-7.79 (m, 3 H, Ar-7$^1$, 5$^3$, and 4$^1$), 8.07 (d, J=7.48 Hz, 1 H, Ar-4$^3$ H), 8.40 (br. s., 1 H, Ar-2$^1$ H), 8.49 (br. s., 1 H, Ar-2$^3$ H); $^{13}$C NMR (500 MHz, DMSO-d$_6$) δ 157.7, 144.9, 144.2, 140.8, 139.6, 137.2, 134.3, 130.3, 128.7 (2×C), 128.3, 127.7 (2×C), 126.3, 125.4, 124.6, 123.1, 122.2, 120.1, 111.4, 47.9

3-[4-(2-benzimidazolylethyl)phenyl]-1-methoxybenzene (VNPP321(B18))

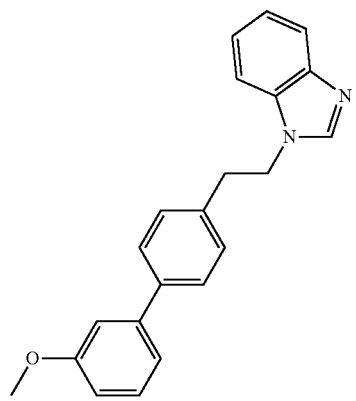 [SMILES: COc1cccc(-c2ccc(CCn3cnc4ccccc43)cc2)c1]

Method B: using VNPP319C (0.2 g, 0.66 mol) and 3-methoxyphenylboronic acid (0.16 g, 1.05 mmol). On purification by FCC over short column [petroleum ether/EtOAc (1:1)] gave VNPP321 as viscous liquid (0.16 g, 73%): IR (Neat) 2936, 1599, 1480, 1457, 1288, 1214, 1168, 1051, 778, 741 cm$^{-1}$; $^1$H NMR (500 MHz, CDCl$_3$) 67 3.16 (t, J=7.02 Hz, 2 H, CH$_2$), 3.85 (s, 3 H, CH$_3$), 4.41 (t, J=7.02 Hz, 2H, =N—CH$_2$), 6.88 (dd, J=8.24, 1.83 Hz, 1 H, Ar-4$^3$-H), 7.05-7.10 (m, 3 H, Ar-6$^3$, 5$^1$ and 6$^1$ Hs), 7.13 (d, J=7.63 Hz, 1 H, Ar-7$^1$-H), 7.28-7.36 (m, 3 H, Ar-2$^2$, 6$^2$ and 2$^3$ Hs), 7.37-7.42 (m, 1 H, Ar-5$^3$-H), 7.48 (d, J=8.09 Hz, 2 H, Ar-3$^2$ and 5$^2$Hs). 7.66 (s, 1 H, Ar-2$^1$-H), 7.82 (dd, J=6.18, 2.52 Hz, 1 H, Ar-4$^1$ H); $^{13}$C NMR (500 MHz, CDCl$_3$) δ 160.1, 143.9, 143.1, 142.3, 140.1, 136.9, 133.7, 130.0, 129.2 (2×C), 127.7 (2×C), 123.2, 122.4, 120.6, 119.7, 112.9, 112.9, 109.8, 55.5, 46.8, 36.0

3-[4-(2-benzimidazolylethyl)phenyl]phenol (VNPP355 (B19))

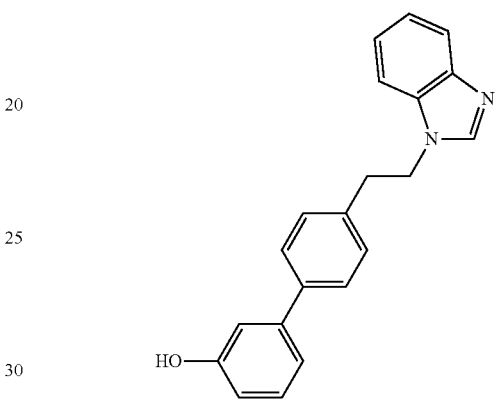

Method B: using VNPP319C (0.21 g, 0.7 mmol) and 3-hydroxyphenylboronic acid (0.15 g, 1.08 mmol). Yield (0.08 g, 37%): mp 226-227° C.; IR (Neat) 2931, 1585, 1499, 1456, 1307, 1215, 1200, 785 cm$^{-1}$; $^1$H NMR (500 MHz, DMSO-d$_6$) δ 3.16 (t, J=7.10 Hz, 2 H, CH$_2$), 4.52 (t, J=7.17 Hz, 2 H, =N—CH$_2$), 6.77 (d, J=7.48 Hz, 1 H, Ar-4$^3$-H), 6.97-7.09 (m, 2 H, Ar-6$^3$, 5$^1$ Hs), 7.15-7.32 (m, 5 H, Ar-7$^1$, 2$^3$, 5$^3$, 2$^2$ and 6$^2$ Hs), 7.49 (d, J=7.78 Hz, 2 H, Ar-3$^2$, 5$^2$ Hs), 7.59-7.73 (m, 2 H, Ar-8$^1$, 5$^1$ Hs), 8.10 (s, 1 H, Ar-2$^1$ H), 9.54 (s, 1 H, —OH); $^{13}$C NMR (500 MHz, DMSO-d$_6$) δ 158.4, 144.5, 144.0, 141.9, 139.1, 138.0, 134.3, 130.5, 129.9 (2×C), 127.1 (2×C), 122.8, 122.1, 120.0, 117.9, 114.9, 113.9, 111.1, 46.0, 35.6

3-[4-(2-benzimidazolylethyl)phenyl]benzenecarbonitrile (VNPP357 (B20))

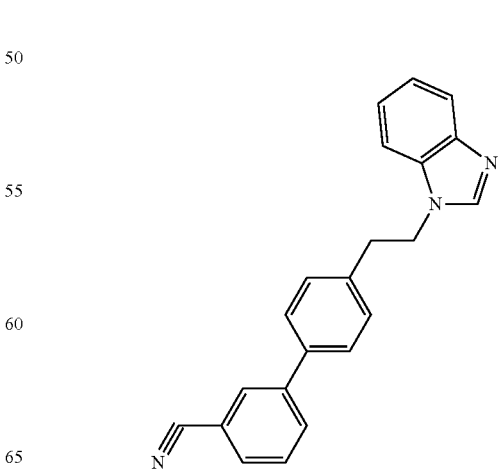

Method B: using VNPP319C (0.2 g, 0.66 mmol) and 3-nitrilephenylboronic acid (0.15 g, 1 mmol). Yield (0.18 g, 83.5%): mp 157-159° C.; IR (Neat) 3073, 2227, 1493, 1456, 1396, 1325, 1283, 1224, 796, 749 cm$^{-1}$; $^1$H NMR (500 MHz, DMSO-d$_6$) δ 3.19 (t, J=7.32 Hz, 2 H, CH$_2$), 4.54 (t, J=7.32 Hz, 2 H, =N—CH$_2$), 7.20 (t, J=7.55 Hz, 1H, Ar-5$^1$ H), 7.26 (t, J=7.55 Hz, 1 H, Ar-6$^1$ H), 7.32 (d, J=8.09 Hz, 2H, Ar-2$^2$, 6$^2$ Hs), 7.63 (d, J=6.87 Hz, 1 H, Ar-7$^1$ H), 7.64-7.70 (m, 4 H, Ar-3$^2$, 5$^2$, 4$^1$ and 5$^3$ Hs), 7.80 (d, J=7.63 Hz, 1 H. Ar-6$^3$ H), 8.00 (d, J=8.09 Hz, 1 H, Ar-4$^3$-H), 8.09 (s, 1 H, Ar-2$^3$ H), 8.13 (s, 1H Ar-2$^1$ H); $^{13}$C NMR (500 MHz, CDCl$_3$) δ 144.1, 143.1, 142.0, 138.0, 137.8, 133.6, 131.5, 130.9, 129.8, 129.7, 129.5, 127.6, 127.6, 123.1, 122.3, 120.8, 120.6, 119.0, 113.1, 109.7, 46.6, 36.0

1-(3'-methoxy-[1,1'-biphenyl]-4-yl)-1H-benzo[d]imidazole (VNPP444B(B23))

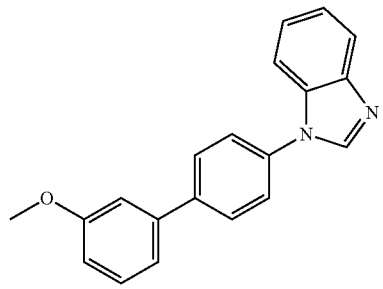 [SMILES: COc1cccc(-c2ccc(-n3cnc4ccccc43)cc2)c1]

Method B: using VNPP442 and 3-methoxyphenylboronic acid. On purification by FCC [petroleum ether/EtOAc (3:1)] gave solid VNPP444B(B23) (0.03 g, 27%)$^1$H NMR (400 MHz, CDCl$_3$) δ 3.90 (s, 3 H, CH$_3$), 6.96 (dd, J=8.07, 2.20 Hz, 1 H, Ar-4$^3$-H), 7.18 (t, J=1.96 Hz, 1 H), 7.23 (d, J=7.58 Hz, 1 H), 7.33-7.39 (m, 2 H), 7.39-7.45 (m, 1 H), 7.56-7.64 (m, 3 H), 7.79 (d, J=8.56 Hz, 2 H, Ar-3$^2$, 5$^2$-Hs), 7.87-7.94 (m, 1 H), 8.16 (s, 1 H, Ar-2$^1$ H); $^{13}$C NMR (101 MHz, CDCl$_3$) δ 160.13, 144.16, 142.25, 141.31, 140.95, 135.60, 133.72, 130.05, 128.74, 124.28, 123.76, 122.86, 120.71, 119.61, 113.15, 113.04, 110.51, 55.38

1-(3'-hydroxy-[1,1'-biphenyl]-3-yl)-1H-benzoimidazole (VNPP441C(B24))

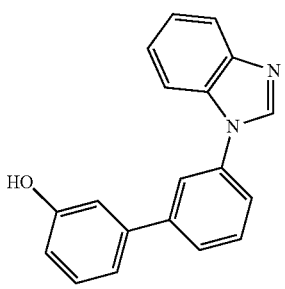 [SMILES: Oc1cccc(-c2cccc(-n3cnc4ccccc43)c2)c1]

Method B: using VNPP371/1 and 3-hydroxyphenylboronic acid. On purification by FCC [petroleum ether/EtOAc (3:1)] gave solid VNPP441C(B24) (0.047 g, 43%): $^1$H NMR (400 MHz, CDCl$_3$) δ 6.98 (d, J=8.07 Hz, 1 H, Ar-4$^3$), 7.17 (br. s., 2 H), 7.20-7.24 (m, 1 H), 7.28-7.39 (m, 2 H), 7.42 (d, J=7.34 Hz, 1 H), 7.49 (d, J=7.83 Hz, 1 H), 7.52 (s, 1 H), 7.59 (t, J=7.83 Hz, 1 H), 7.68 (d, J=7.58 Hz, 1 H), 7.89 (d, J=7.82 Hz, 1 H), 8.16 (s, 1 H, Ar-2$^1$); $^{13}$C NMR (101 MHz, CDCl$_3$) δ 157.58, 143.34, 142.90, 141.93, 140.85, 136.36, 133.63, 130.44, 130.36, 127.06, 124.16, 123.29, 122.89, 122.76, 120.19, 118.74, 115.77, 114.18, 110.75

1-(3'-methoxy-[1,1'-biphenyl]-3-yl)-1H-benzo[d]imidazole (VNPP420 (B25))

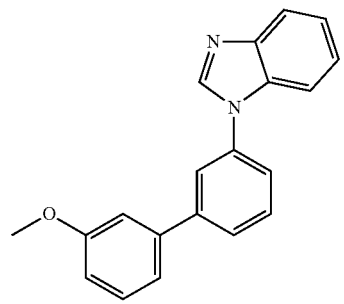 [SMILES: COc1cccc(-c2cccc(-n3cnc4ccccc43)c2)c1]

Method B: using VNPP371/1 and 3-methoxyphenylboronic acid. On purification by FCC [petroleum ether/EtOAc (3:1)] gave sticky solid VNPP420(B25) (0.1 g, 91%): $^1$H NMR (400 MHz, CDCl$_3$) δ 3.88 (br. s., 3 H, CH$_3$), 6.96 (d, J=7.34 Hz, 1 H, Ar-4$^3$ H), 7.15 (br. s., 1 H, Ar-6$^3$ H), 7.22 (br. s., 1 H, Ar-5$^1$ H), 7.35 (br. s., 2 H, Ar-6$^1$, 2$^3$ Hs), 7.41 (br. s., 1 H, Ar-5$^3$ H), 7.51 (br. s., 1 H, Ar-6$^2$ H), 7.59 (d, J=3.42 Hz, 1H, Ar 5$^2$ H), 7.64 (s, 1 H, Ar-4$^2$ H), 7.68 (s, 1 H, Ar-4$^1$ H), 7.72 (br. s., 1 H, Ar-7$^1$ H), 7.89 (br. s., 1 H, Ar-2$^2$ H), 8.17 (br. s., 1 H, Ar-2$^1$); $^{13}$C NMR (101 MHz, CDCl$_3$) δ 160.1, 144.1, 143.3, 142.3, 141.2, 136.8, 133.7, 130.4, 130.1, 126.8, 123.7, 122.8, 122.8, 122.8, 120.7, 119.6, 113.4, 113.0, 110.5, 55.3; HRMS calcd 323.1154 (C$_{20}$H$_{16}$N$_2$O)Na$^+$, found 323.1156.

3-[4-(2-benzimidazolylethyl)phenyl]benzoicacid (VNPP359)

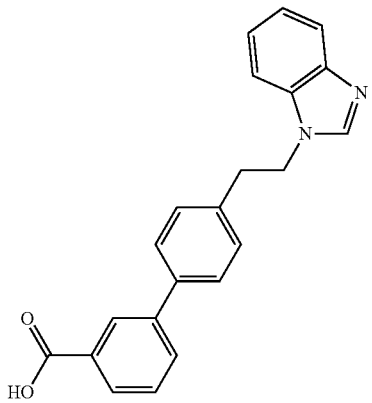 [SMILES: O=C(O)c1cccc(-c2ccc(CCn3cnc4ccccc43)cc2)c1]

By slightly modifying Method B: using VNPP319C (0.2 g, 0.66 mmol) and 3-carboxyphenylboronic acid (0.17 g, 1 mmol) and 2 M aq Na$_2$CO$_3$ (2×2.13 mL). After completion of reaction, reaction mixture neutralized with dil. HCl, extracted with EtOAc, filtered and concentrated. On purification by FCC [petroleum ether/EtOAc (1:1) and then with 7% ethanol in DCM with traces of CH$_3$COOH] gave VNPP359 (0.07 g, 29%): mp 215-217° C.; IR (Neat) 1689, 1505, 1438, 1310, 1242, 1164, 765, 754 cm$^{-1}$; $^{1}$H NMR (500 MHz, DMSO-d$_6$) δ 3.19 (t, J=7.25 Hz, 2 H, CH$_2$), 4.55 (t, J=7.25 Hz, 2 H, =N—CH$_2$), 7.19-7.24 (m, 1 H, Ar-5$^1$-H), 7.24-7.29 (m, 1 H, Ar-6$^1$ H), 7.31 (d, J=8.09 Hz, 2 H, Ar-2$^2$, 6$^2$ Hs), 7.56-7.63 (m, 3 H, Ar-3$^2$, 5$^2$, 7$^1$ Hs), 7.64-7.70 (m, 2 H, Ar-4$^1$, 5$^3$ Hs), 7.86-7.92 (m, 1 H, Ar-4$^3$-H), 7.94 (d, J=7.78 Hz, 1 H, Ar-6$^3$-H), 8.11 (s, 1 H, Ar-2$^1$ H), 8.17 (m, 1 H, Ar-2$^3$-H), 13.07 (br, 1 H, COOH); $^{13}$C NMR (500 MHz, DMSO-d$_6$) δ 167.9, 144.5, 144.0, 140.8, 138.6, 138.1, 134.3, 132.2, 131.5, 130.1 (2×C), 129.9, 128.7, 127.7, 127.3 (2×C), 122.8, 122.1, 120.0, 111.1, 45.9, 35.6

5-{3-[4-(benzimidazolylethyl)phenyl]phenyl}-1H-1,2,3,4-tetraazole (VNPP364)

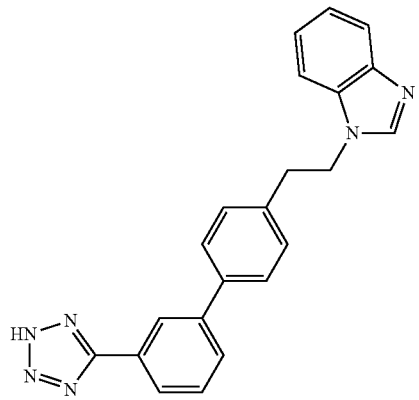 [SMILES: c1cc(-c2ccc(CCn3cnc4ccccc43)cc2)cc(-c2nn[nH]n2)c1]

Method C: using 0.85 g (0.26 mmol) of VPNN357. Yield (0.07 g, 76.5%): mp 223-225° C.; IR (Neat) 1575, 1505, 1456, 1230, 992, 800, 742 cm$^{-1}$[13]; $^{1}$H NMR (500 MHz, DMSO-d$_6$) δ 3.20 (t, J=7.17 Hz, 3H, CH$_2$), 4.56 (t, J=7.25 Hz, 2 H, =N—CH$_2$), 7.20 (t, J=7.55 Hz, 1 H, Ar-5$^1$ H), 7.26 (t, J=7.48 Hz, 1 H, Ar-6$^1$ H), 7.33 (d, J=7.93 Hz, 2 H, Ar-2$^2$, 6$^2$ Hs), 7.61-7.72 (m, 5 H, Ar-3$^2$, 5$^2$, 6$^3$, 5$^3$ and 7$^1$ Hs), 7.86 (d, J=7.78 Hz, 1 H, Ar-4$^1$ H), 8.02 (d, J=7.63 Hz, 1 H, Ar-4$^3$ H), 8.10 (s, 1 H, Ar-2$^2$ H), 8.29 (s, 1 H, Ar-2$^4$-H); $^{13}$C NMR (500 MHz, DMSO-d$_6$) δ 156.0, 144.5, 143.8, 141.4, 138.8, 137.9, 134.3, 130.7, 130.2 (2×C), 129.7, 127.4 (2×C), 126.4, 125.7, 125.6, 122.9, 122.1, 120.0, 111.2, 46.0, 35.6

6-(3-benzimidazolylphenyl)naphthalen-2-ol (VNPP372/2 (Na1))

Method B: using VNPP371/1 (0.1 g, 0.37 mmol) and 6-hydroxynaphthyl-2-boronic acid (0.1 g, 0.53 mmol). On purification by FCC over short column [petroleum ether/ EtOAc (1:1) and then with 2% ethanol in DCM with traces of TEA] gave VNPP372/2 (0.1 g, 81%): mp 252-253° C.; IR (Neat) 1599, 1495, 1462, 1229, 1196, 962, 792, 741 cm$^{-1}$; $^{1}$H NMR (500 MHz, DMSO-d$_6$) δ 7.14 (d, J=8.54 Hz, 1 H, Ar-7$^3$ H), 7.17 (d, J=2.5 Hz, 1 H, Ar-5$^3$ H), 7.35 (p, J=7.4 Hz, 2 H, Ar-6$^1$ and 5$^1$ Hs), 7.67 (d, J=7.8 Hz, 1 H, Ar-6$^2$ H), 7.70-7.75 (m, 2 H, Ar-4$^2$ and 5$^2$ Hs), 7.81 (d, J=8.5 Hz, 2 H, Ar Hs), 7.87 (dd, J=8.7, 3.3 Hz, 2 H, Ar Hs), 7.90 (d, J=7.6 Hz, 1 H, Ar-8$^3$ H), 8.04 (s, 1 H, Ar-10$^3$ H), 8.25 (s, 1 H, Ar-2$^1$ H), 8.70 (s, 1 H, Ar-2$^2$ H), 9.87 (s, 1H, —OH); $^{13}$C NMR (500 MHz, DMSO-d$_6$) δ 156.5, 144.5, 144.1, 142.9, 137.3, 134.8, 133.8, 131.2, 130.6, 128.6, 127.4, 126.5, 126.4, 125.9, 124.2, 123.1, 122.7, 122.5, 120.6, 119.8, 111.4, 109.1

6-(3-benzimidazolylphenyl)-2-methoxynaphthalene (VNPP373/2 (Na2))

Method B: using VNPP371/1 and 6-methoxynaphthyl-2-boronic acid On purification by FCC over short column [petroleum ether/EtOAc/TEA (4:2:0.1)] gave VNPP373/2 (Na2) (0.1 g, 81%): mp 156-157° C.; IR (Neat) 1604, 1499, 1450, 1228, 1202, 1037, 837, 733 cm$^{-1}$; $^{1}$H NMR (500 MHz, CDCl$_3$) δ 3.95 (br. s., 3 H, CH$_3$), 7.14-7.23 (m, 2 H), 7.36 (br. s., 2 H), 7.51 (br. s., 1 H), 7.62 (br. s., 1 H), 7.67 (br. s., 1 H,), 7.73 (d, J=8.56 Hz, 1 H), 7.80 (br. s., 2 H), 7.84 (br. s., 2 H), 7.90 (br. s., 1H), 8.02 (br. s., 1 H), 8.20 (br. s., 1 H); $^{1}$H NMR (400 MHz, DMSO-d$_6$) δ 3.90 (br. s., 3 H), 7.38 (s, 2 H), 7.35 (s, 1 H), 7.73 (s, 1 H), 7.71 (s, 2 H), 7.89-7.99 (m, 4 H), 8.07 (br. s., 1 H), 8.32 (br. s., 1 H), 8.71 (br. s., 1 H); $^{13}$C NMR (101 MHz, CDCl$_3$) δ 158.1, 144.1, 143.4, 142.3, 136.9, 134.7, 134.2, 133.8, 130.4, 129.8, 129.1, 127.6, 126.8, 125.9, 125.6, 123.7, 122.8, 122.7, 122.5, 120.7, 119.5, 110.5, 105.6, 55.3; HRMS calcd 373.1311 (C$_{24}$H$_{18}$N$_2$O)H$^+$, found 373.1314.

4-Hydrosystyrene (VNPP383/2)

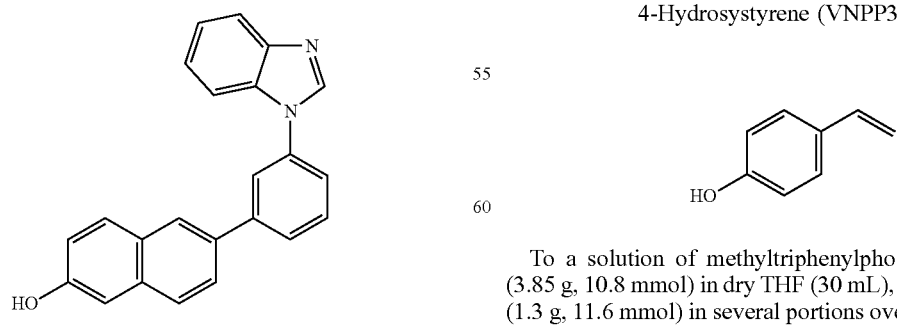

To a solution of methyltriphenylphosphonium bromide (3.85 g, 10.8 mmol) in dry THF (30 mL), was added t-BuOK (1.3 g, 11.6 mmol) in several portions over 30 min. Reaction mixture was stirred under argon for 1 h, then 4-hydroxybenzaldehyde (0.5 g, 4.09 mmol) was added, and stirring continued for another 3 h. The reaction mixture then diluted with DCM (100 ml), washed with water and brine, dried (Na₂SO₄) and solvents were evaporated under vacuum. The crude product was purified by FCC [petroleum ether/EtOAc (4:1)] to get VNPP383/2 (0.25 g, 50.8%): mp 101-105° C.; IR (Neat) 3299, 1611, 1597, 1509, 1443, 1365, 1222, 1171, 824 cm⁻¹; ¹H NMR (500 MHz, CDCl₃) δ 4.13 (br, 1 H, —OH), 5.06-5.18 (m, 1 H, vinyl CH₂—H), 5.54-5.65 (m, 1 H, vinyl CH₂—H), 6.65 (dd, J=17.47, 10.91 Hz, 1 H, Vinyl CH), 6.79 (dd, J=8.39 Hz, 2 H, Ar-2, 6 Hs), 7.30 (dd, J=8.39 Hz, 2 H, Ar-3, 5 Hs)

4-[(1E)-2-(3-benzimidazolylphenyl)vinyl]phenol (VNPP388 (S1))

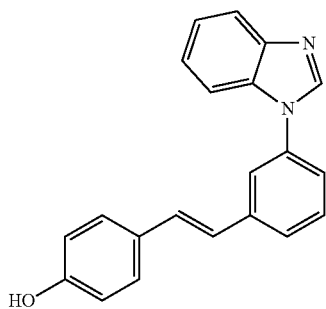 [SMILES: Oc1ccc(/C=C/c2cccc(-n3cnc4ccccc43)c2)cc1]

A mixture of p-Hydrosystyrene (VNPP383-2) (0.1 g, 0.83 mmol), 1-(3-bromophenyl)-1H-benzo[d]imidazole (VNPP371/1) (0.12 g, 0.44 mmol), triethanolamine (0.065 g, 0.43 mmol) and Pd(II) acetate (0.004 g, 0.018 mmol) was stirred under argon at 100° C. for 24 h. The reaction mixture was cooled to room temperature, quenched by the addition of 2N HCl, and extracted with EtOAc (3×10 mL). the organic phases were dried (Na₂SO₄), evaporated and crude product was purified by FCC [petroleum ether/EtOAc/TEA (3:2:0.01)] to get pure VNPP388 (0.025 g, 19%): mp 182-184° C.; IR (Neat1596, 1580, 1496, 1454, 1278, 1232, 1217, 1171, 819 cm⁻¹; ¹H NMR (400 MHz, DMSO-d6) δ 6.79 (m, J=8.31 Hz, 2 H, Ar-3³ and 3⁵ Hs), 7.14 (d, J=16.38 Hz, 1 H, vinyl CH), 7.29-7.37 (m, 3 H, vinyl CH, Ar-1⁶ and 1⁵ Hs), 7.46 (m, J=8.31 Hz, 2 H, Ar-3² and 3⁶Hs), 7.53-7.66 (m, 4 H, Ar-2⁶, 1⁴, 2⁵ and 2⁴ Hs), 7.79 (d, J=7.58 Hz, 1 H, Ar-1⁷ H), 7.85 (s, 1 H, Ar-1² H), 8.60 (s, 1 H, Ar-2² H), 9.63 (s, 1 H, —OH); ¹³C NMR (400 MHz, DMSO-d6) δ 158.1, 144.3, 143.8, 140.2, 136.9, 133.6, 130.7, 130.6, 128.6, 128.2, 125.7, 124.4, 123.9, 122.9, 122.4, 121.4, 120.4, 116.0, 111.2

1-[(1E)-2-(3-benzimidazolylphenyl)vinyl]-4-methoxybenzene (VNPP391B3(S2))

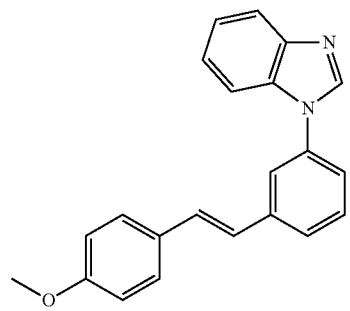 [SMILES: COc1ccc(/C=C/c2cccc(-n3cnc4ccccc43)c2)cc1]

Sythensized using P-Methoxyphenylstyren by following procedure for synthesis of VNPP388 (S1). The crude product was purified by FCC [petroleum ether/EtOAc/DCM/TEA (6:1:1:0.01)] to get pure VNPP391B3(S2) (0.1 g, 83.4%): mp 95-96° C.; ¹H NMR (400 MHz, CDCl₃) δ 3.84 (s, 3 H, CH₃), 6.89-6.95 (m, 2 H, Ar-3³ and 5³ Hs), 7.03 (d, J=16.38 Hz, 1 H, vinyl CH), 7.15 (d, J=16.14 Hz, 1 H, vinyl CH), 7.33-7.40 (m, 3 H, Ar-6¹, 5¹ and 2³Hs), 7.46-7.51 (m, 2 H, Ar— 6³ and 6² Hs), 7.52-7.60 (m, 3 H, Ar—, 4¹, 5² and 4² Hs), 7.62 (s, 1 H, Ar-2² H), 7.88-7.93 (m, 1 H, Ar-7¹ H), 8.16 (s, 1 H, Ar-2¹ H)¹³C NMR (400 MHz, CDCl₃) δ 159.7, 144.1, 142.3, 139.9, 136.8, 133.7, 130.2, 130.2, 129.4, 128.0 (2×C), 125.8, 124.9, 123.7, 122.8, 122.5, 121.5, 120.6, 114.2 (2×C), 110.5, 55.3; HRMS calcd 349.1311 (C₂₁H₁₈N₂O)Na⁺,—found 349.1314.

4-{[(3-benzimidazolylphenyl)methyl]amino}phenol (VNPP428(Am-a1))

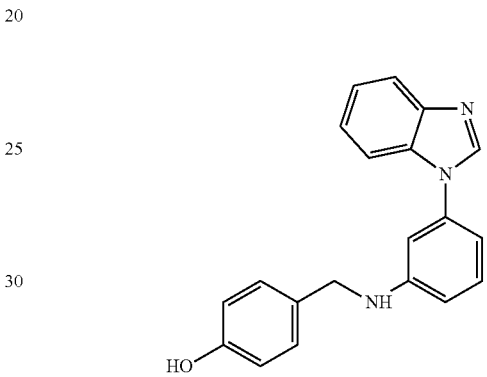

Method D: using 4-hydroxybenaldehyde. Yield 33.8%; mp 94-97° C.; ¹H NMR (400 MHz, DMSO-d₆) δ 4.14-4.28 (m, 2 H, CH₂), 6.65-6.80 (m, 5 H), 7.19 (d, J=7.34 Hz, 2 H), 7.26 (br. s., 2 H), 7.31 (br. s., 1 H), 7.74 (d, J=6.85 Hz, 1 H), 8.45 (br. s., 1 H), 9.32 (br. s., 1 H); ¹H NMR (400 MHz, CDCl₃) δ 4.28 (s, 2 H, CH₂), 4.61 (s, 1 H, NH), 6.66 (t, J=2.08 Hz, 1 H), 6.68-6.73 (m, 1 H), 6.75-6.80 (m, 1 H), 6.85-6.91 (m, 2 H), 7.19-7.25 (m, 2 H), 7.27-7.32 (m, 2 H), 7.41 (d, J=4.16 Hz, 1 H), 7.80-7.89 (m, 1 H), 8.09 (s, 1 H); ¹³C NMR (101 MHz, DMSO-d₆) δ 156.7, 150.4, 143.4, 137.1, 130.7, 130.0, 128.9 (2×C), 128.2, 123.6, 122.7, 120.3, 115.6 (2×C), 115.2, 112.4, 111.3, 110.6, 106.9, 46.3; HRMS calcd 316.1444 (C₂₀H₁₇N₃O)H⁺, found 316.1446.

[(3-benzimidazolylphenyl)methyl](4-methoxyphenyl)amine (VNPP429(Am-a2))

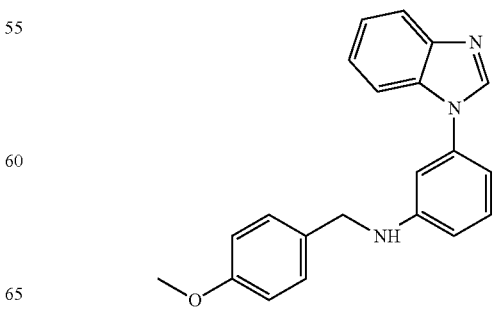

Method D: using 4-methoxybenzaldehyde. Yield 50%; mp 121-22° C.; $^1$H NMR (400 MHz, DMSO-$d_6$) δ 3.74 (br. s., 3 H), 4.22-4.34 (m, 2H), 6.63-6.79 (m, 4 H), 6.93 (d, J=7.83 Hz, 2 H), 7.17-7.38 (m, 6H), 7.73 (d, J=6.85 Hz, 1 H), 8.45 (br. s., 1 H); $^{13}$C NMR (101 MHz, CDCl$_3$) δ 159.0, 149.3, 144.0, 142.3, 137.4, 133.6, 130.6, 130.4, 128.7 (2×C), 123.4, 122.6, 120.4, 114.2 (2×C), 112.6, 112.4, 110.8, 107.6, 55.3, 47.5; HRMS calcd 352.1420 ($C_{21}H_{19}N_3O$)Na$^+$, found 352.1422.

N-(3-benzimidazolylphenyl)(4-methoxyphenyl)carboxamide (VNPP432 (Amd-b2))

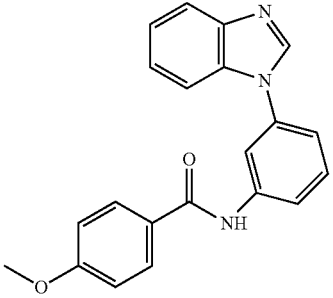 [SMILES: COc1ccc(C(=O)Nc2cccc(-n3cnc4ccccc43)c2)cc1]

A mixture of VNPP423 (0.15 g, 0.72 mmol), TEA (0.1 g, 1.0 mmol) and 4-methoxybenzoyl chloride (0.3 g, 1.8 mmol) in EtOAc (10 mL) stirred at room temperature for 5 hrs. Reaction mixture filtered, filtrate washed with pet ether-EtOAc mixture (3:2), then with water. Mother liquor purified separately by FCC [1% ethanol in DCM with traces of TEA]. Overall yield 0.12 g (48.7%): mp 212-214° C.; $^1$H NMR (400 MHz, CDCl$_3$) δ 3.83 (s, 2 H), 6.93 (d, J=6.85 Hz, 2 H) 7.06 (d, J=7.82 Hz, 1 H) 7.19 (t, J=7.58 Hz, 1 H) 7.31-7.44 (m, 4 H) 7.77-7.81 (m, 2 H) 7.97 (d, J=8.31 Hz, 1 H) 8.02 (s, 1 H) 8.31 (s, 1 H, Ar-2$^1$) 8.72 (s, 1 H, NH); HRMS calcd 344.1393 ($C_{21}H_{17}N_3O_2$)H$^+$, found 344.1397.

(3-benzimidazolylphenyl)[(4-methoxyphenyl)sulfonyl]amine (VNPP431(SulAmd-2))

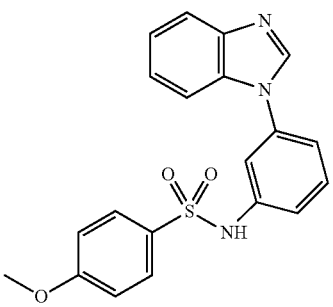 [SMILES: COc1ccc(S(=O)(=O)Nc2cccc(-n3cnc4ccccc43)c2)cc1]

A mixture of VNPP423 (0.15 g, 0.72 mmol), 4-methoxybenzenesulfonyl chloride (0.44 g, 2.15 mmol) in pyridine was refluxed for 24 h. Cooled to room temperature, poured on ice cold water, extracted with EtOAc, evaporated and crude product was purified by FCC [1% ethanol in DCM with traces of TEA]. VNPP431(SulAmd-2) (0.13 g, 47.8%): mp 169-71° C.; $^1$H NMR (400 MHz, CDCl$_3$) δ 3.84 (s, 3 H, CH$_3$) 6.90-6.97 (m, 2 H, Ar-2$^2$, 4$^2$ Hs) 7.13-7.19 (m, 1 H, Ar-6$^2$ H) 7.21-7.26 (m, 1 H, Ar-5$^2$ H) 7.28-7.31 (m, 2 H, Ar—Hs) 7.32 (d, J=1.96 Hz, 1 H, Ar—H) 7.33-7.40 (m, 2 H, Ar—Hs) 7.41-7.48 (m, 1 H, Ar—H) 7.76-7.81 (m, 2 H, Ar—Hs) 7.83-7.88 (m, 1 H, Ar—H) 8.07 (s, 1 H, Ar-2$^1$); $^{13}$C NMR (101 MHz, CDCl$_3$) δ 163.4, 143.9, 142.0, 138.6, 137.2, 133.3, 131.0, 130.4, 129.5 (2×C), 123.9, 123.0, 120.6, 120.1, 120.0, 115.9, 114.4 (2×C), 110.4, 55.6; HRMS calcd 402.0882 ($C_{20}H_{17}N_3O_3S$)Na$^+$, found 402.0886.

6β-imidazol-1yl-3,5-cycloandrostan-17-benzimidazole-1-yl-16-ene (VNPP433-6β), 3α-(1H-imidazol-1-yl)-17-(1H-benzimidazol-1-yl) androsta-5,16-diene (VNPP433-3α(A3)) and 3β-(1H-imidazol-1-yl)-17-(1H-benzimidazol-1-yl) androsta-5,16-diene (VNPP433-3β(2d)(A1))

A round bottom flask equipped with Dean-stark apparatus and condenser is charged with VNPT88 (0.6 g, 1.3 mmol), imidazole (0.3 g, 4.4 mmol) and toluene. Reaction mixture refluxed for 12 h. Reaction mixture cooled, solvent evaporated under vacuum, residue washed with water to get crude product. Purification by FCC [1% ethanol in DCM with traces of TEA] to get product of three components VNPP433-6β, VNPP433-3α(A3) and VNPP433-3β(2d) (A1) (0.23 g, 61%): This three component mixture subjected to preparative HPLC for the isolation of individual compounds.

HPLC separation: Preparative HPLC separation was performed on Waters Prep Nova-Pak (7.8×300 mm, 60 Å, 6 μm) HR C-18 reversed-phase HPLC column (Waters, Milford, Mass.) coupled with Waters 2489 UV/visible detector operated at 254 nm. Elution was performed using Waters model 2535 Quarternary Gradient Module pump to deliver a constant flow rate of 6 mL/min. The solvent system consisted of Water/MeOH/CH$_3$CN (200:500:300, v/v/v+500 μL of TEA per 1000 mL of mobile phase) and maintained isocratically. Sample stock solution was prepared by dissolving 200 mg (three component mixture obtained by FCC) in 20 mL of mobile phase. Total of twenty injections each 1 mL volume with run time of 13 minutes performed. Compound VNPP433-6β was collected between 5.12-6.73 min, VNPP433-3α(A3) collected between 7.77-8.93 min and VNPP433-3β(2d)(A1) was collected between 10.07-12.09 min.

Figure 11:
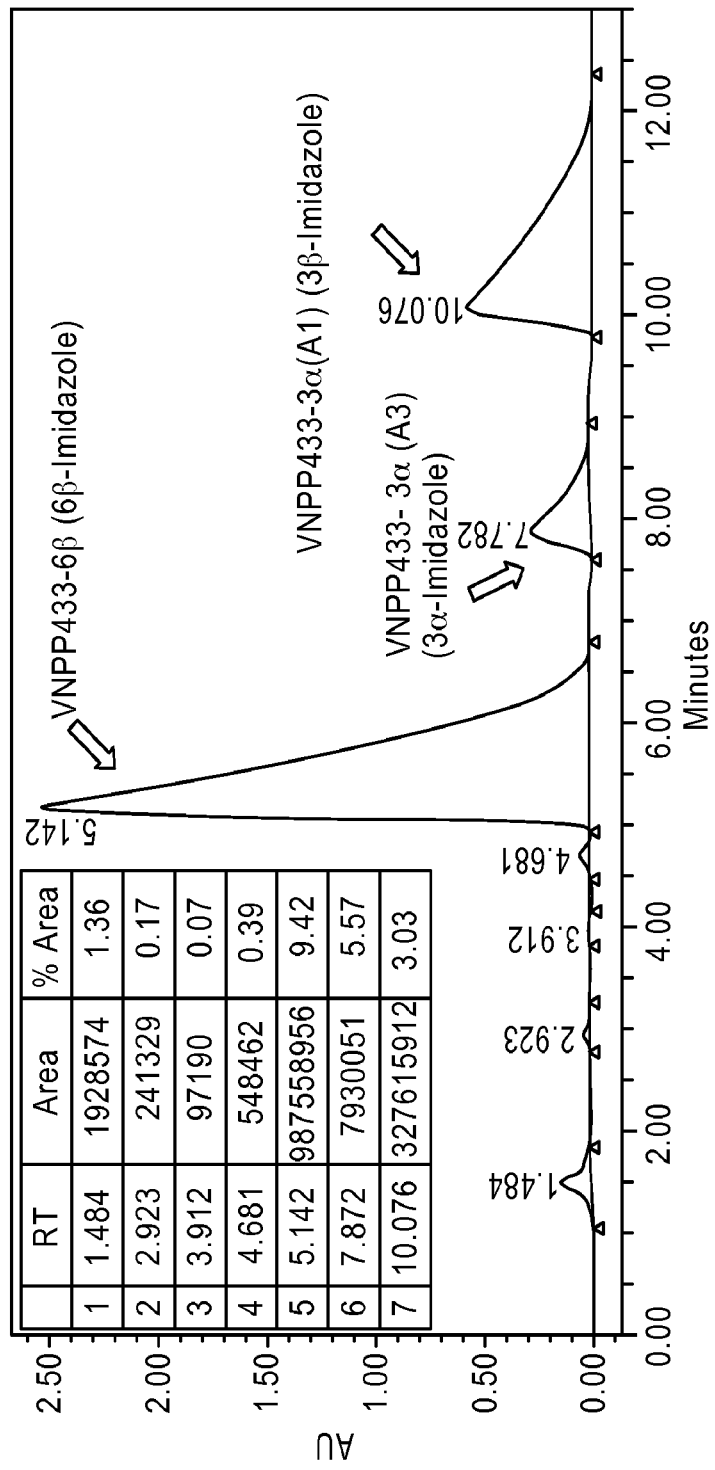
FIG. 11. Example of HPLC chromatogram of three component mixture. The retention times for VNPP433-6β, VNPP433-3α(A3) and VNPP433-3β(2d)(A1) were 5.14, 7.87 and 10.07 min, respectively.
Figure 12:
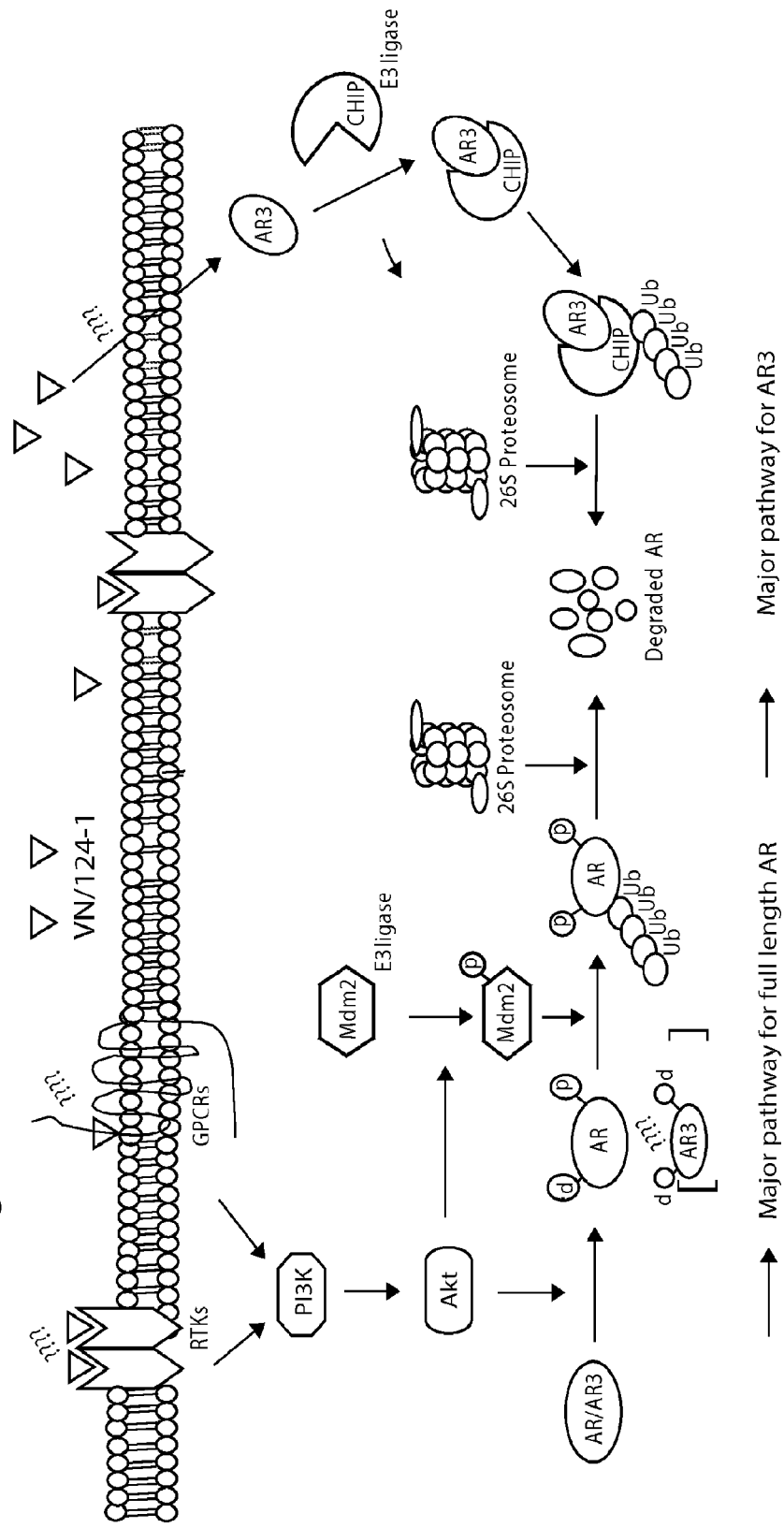
FIG. 12. Mechanisms of induced AR degradation in prostate cancer cells
FIG. 13. Therapeutic approaches to block androgen receptor (AR) transactivation
FIG. 14. Diagram of androgen receptor protein
Figure 13:
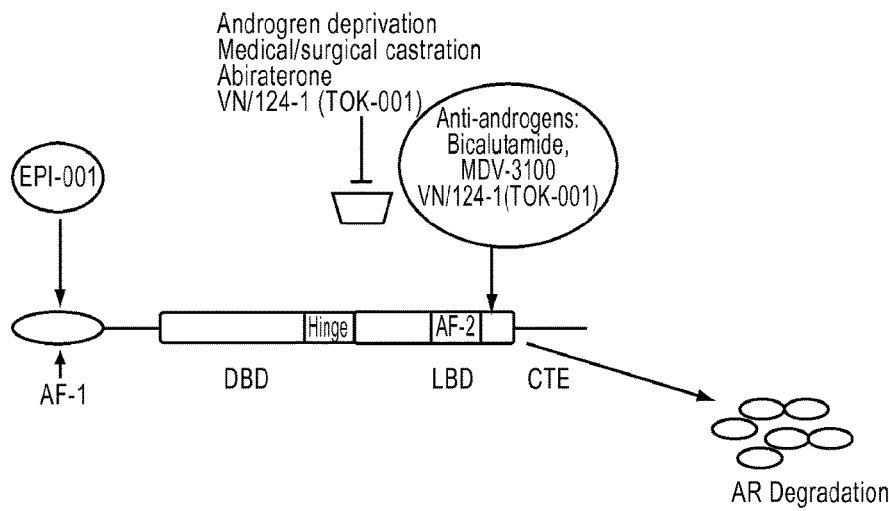
Figure 14:
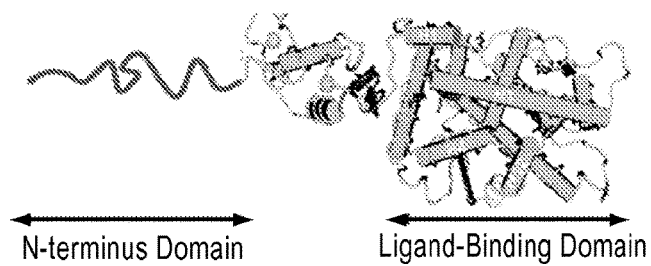

Example of HPLC chromatogram of three component mixture. The retention times for VNPP433-6β, VNPP433-3α(A3) and VNPP433-3β(A1) were 5.14, 7.87 and 10.07 min, respectively. See FIG. 11.

6β-imidazol-1yl-3,5-cycloandrostan-17-benzimidazole-1-yl-16-ene (VNPP433-6β)

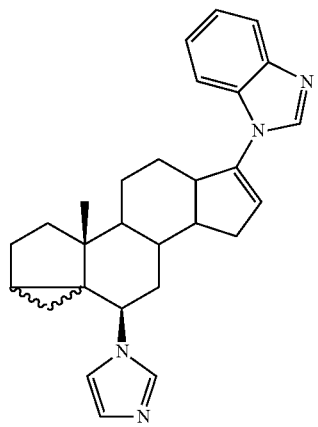

Retension time 5.14 min; 0.13 g, 34.6%, mp 104-106° C.; $^1$H NMR (400 MHz, CDCl$_3$) δ 0.79 (s, 3 H, 18-CH$_3$), 0.97 (s, 3 H, 19-CH$_3$), 3.66 (br. s., 1 H, 6α-H), 5.97-6.02 (m, 1 H, 16-H), 7.09 (s, 1 H, Ar-4$^2$-H), 7.22 (br. s., 1 H, Ar-5$^2$-H), 7.28-7.36 (m, 2 H, Ar-5$^1$, 6$^1$-Hs), 7.46-7.52 (m, 1 H, Ar-7¹-H), 7.79-7.89 (m, 2 H, Ar-4¹-H and Ar-2²-H), 7.95 (s, 1 H, Ar-2¹-H); ¹H NMR (400 MHz, DMSO-d₆) δ ppm 0.67 (s, 3 H), 0.91 (s, 3H), 3.73 (br. s., 1 H), 6.09 (s, 1 H), 6.93 (br. s., 1 H), 7.21-7.33 (m, 2H), 7.36 (s, 1 H), 7.57 (d, J=7.82 Hz, 1 H), 7.70 (d, J=7.58 Hz, 1 H), 7.85 (br. s., 1 H), 8.25 (s, 1 H); ¹³C NMR (400 MHz, CDCl₃)δ147.35, 143.24, 141.49, 136.41, 134.47, 128.62, 123.52, 123.48, 122.54, 120.21, 118.13, 111.07, 58.61, 55.37, 48.47, 47.42, 43.24, 35.18, 34.90, 34.34, 33.34, 30.14, 29.19, 24.78, 24.24, 22.01, 19.72, 16.25, 14.31; HRMS calcd 439.2856 (C₂₉H₃₄N₄O)H⁺, found 439.2858.

3α-(1H-imidazol-1-yl)-17-(1H-benzimidazol-1-yl) androsta-5,16-diene (VNPP433-3α(A3))

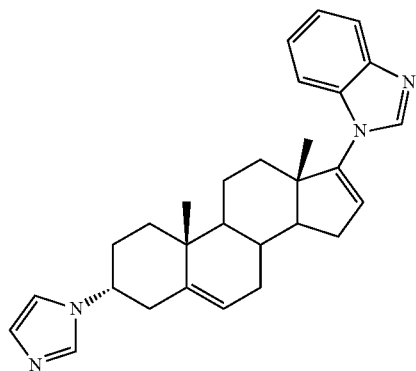 [SMILES: C[C@]12CC[C@@H](n3ccnc3)CC1=CCC1C2CC[C@]2(C)C(n3cnc4ccccc43)=CCC12]

Retention time 8.87 min; 0.012 g, 3.2%: mp 199-200° C.; ¹H NMR (400 MHz, CDCl₃) δ 1.02 (s, 3 H, 18-CH₃), 1.14 (s, 3 H, 19-CH₃), 4.41 (br. s., 1 H, 3δ-H), 5.56 (br. s., 1 H, 6-H), 5.99 (br. s., 1 H, 16-H), 7.03 (d, J=4.89 Hz, 2 H, Ar-4²-H and Ar-5²-H), 7.28-7.33 (m, 2 H, Ar-5¹, 6¹-Hs), 7.49 (d, J=8.31 Hz, 1 H, Ar-7¹-H), 7.73 (s, 1 H, Ar-2²-H), 7.81 (d, J=8.80 Hz, 1 H, Ar-4¹-H), 7.95 (s, 1 H, Ar-2¹-H); ¹H NMR (400 MHz, DMSO-d₆) δ 0.97 (s, 3 H, 18-CH₃), 1.10 (s, 3 H, 19-CH₃), 4.42 (br. s., 1 H, 3δ-H), 5.53 (br. s., 1 H, 6-H), 6.06 (br. s., 1 H, 16-H), 6.86 (s, 1 H), 7.19-7.33 (m, 3 H), 7.56 (d, J=7.83 Hz, 1 H), 7.69 (d, J=7.34 Hz, 2 H), 8.24 (s, 1 H); ¹³C NMR (400 MHz, CDCl₃) δ 147.11, 143.29, 141.64, 139.13, 134.58, 128.56, 124.18, 123.41, 123.36, 122.48, 120.22, 118.70, 111.13, 55.74, 53.00, 50.19, 47.23, 37.27, 35.97, 34.74, 32.29, 31.12, 30.23, 30.20, 29.71, 28.39, 20.27, 19.32, 16.01; HRMS calcd 439.2856 (C₂₉H₃₄N₄O)H⁺, found 439.2857

3β-(1H-imidazol-1-yl)-17-(1H-benzimidazol-1-yl) androsta-5,16-diene (VNPP433-3β(2d)(A1))

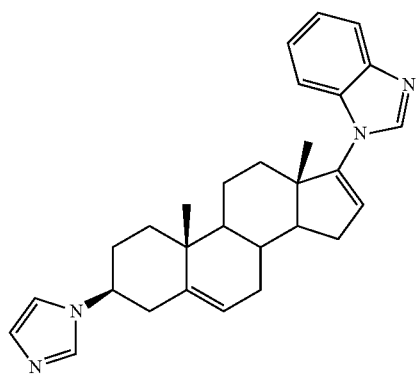 [SMILES: C[C@]12CC[C@H](n3ccnc3)CC1=CCC1C2CC[C@]2(C)C(n3cnc4ccccc43)=CCC12]

Retention time 10.074 min; 0.04 g, 10.6%: mp 198-200° C.; 1H NMR (400 MHz, CDCl3) δ 1.04 (s, 3 H, 18-CH3), 1.14 (s, 3 H, 19-CH3), 3.86-3.98 (m, 1 H, 3α-H), 5.50 (br. s., 1 H, 6-H), 6.00 (br. s., 1 H, 16-H), 7.00 (br. s., 1 H, Ar-42-H), 7.07 (br. s., 1 H, Ar-52-H), 7.28-7.33 (m, 2 H, Ar-51, 61-Hs), 7.49 (d, J=5.62 Hz, 1 H, Ar-71-H), 7.57 (br. s., 1 H, Ar-22-H), 7.82 (d, J=5.62 Hz, 1 H, Ar-41-H), 7.96 (s, 1 H, Ar-21-H); 1H NMR (400 MHz, DMSO-d6) δ ppm 0.99 (s, 3 H), 1.12 (s, 3 H), 3.93-4.03 (m, 1 H), 5.47 (d, J=4.65 Hz, 1 H), 6.07 (s, 1 H), 6.88 (s, 1 H), 7.23-7.32 (m, 2 H), 7.33 (s, 1 H), 7.57 (d, J=7.58 Hz, 1 H), 7.71 (d, J=7.58 Hz, 1 H), 7.74 (s, 1 H), 8.27 (s, 1 H) 13C NMR (400 MHz, CDCl3) δ 147.25, 143.40, 141.72, 140.20, 134.68, 129.27, 124.21, 123.55, 122.63, 122.39, 120.34, 116.97, 111.26, 57.54, 55.92, 50.62, 47.35, 40.67, 38.00, 37.03, 34.94, 31.17, 30.41, 30.02, 29.83, 20.73, 19.47, 16.15, 0.14; HRMS calcd calcd 439.2856 (C₂₉H₃₄N₄O)H+, found 439.2858.

3β-(1H-imidazole-1-carbothioate)-17-(1H-benzimidazol-1-yl) androsta-5,16-diene (VNPP397 (A9))

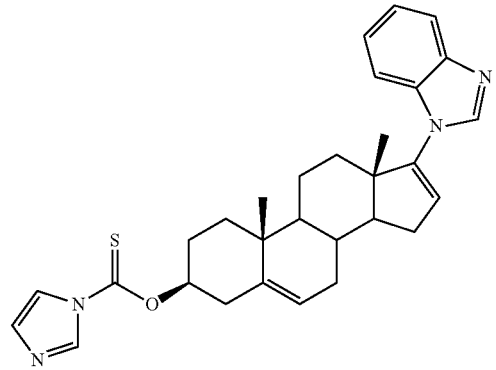 [SMILES: C[C@]12CC[C@H](OC(=S)n3ccnc3)CC1=CCC1C2CC[C@]2(C)C(n3cnc4ccccc43)=CCC12]

A solution of 17-(1H-benzimidazol-1-yl) androsta-5,16-dien-3β-ol (VN/124-1) (0.2 g, 0.515 mmol), 1,1'-thiocarbonyldiimidazole (0.18 g, 1.03 mmol) in anhydrous acetonitrile (2 mL) and DCM (1 mL) was refluxed for 5 h. The solvent evaporated, residue treated with water, and filtered. The crude brown solids obtained was purified by FCC using 1.7% ethanol in DCM in presence of traces of TEA (0.06%) to give VNPP397 (0.14 g, 54.5%): mp 187-88° C.; IR (Neat) 1487, 1456, 1386, 1324, 1291, 1243, 1222, 1110, 986, 827, 743 cm¹ ¹H NMR (400 MHz, CDCl₃) ☐ 1.03 (s, 3 H, 18-CH₃), 1.14 (s, 3 H, 19-CH₃), 5.31-5.42 (m, 1 H, 3α-H), 5.48-5.57 (m, 1 H, 6-H), 6.00 (br. s., 1 H, 16-H), 7.03 (s, 1 H, Ar-4² H), 7.28-7.35 (m, 2 H, Ar-5¹ and 6¹ Hs), 7.49 (d, J=5.14 Hz, 1 H, Ar-5² H), 7.64 (s, 1 H, Ar-4¹ H), 7.82 (d, J=7.58 Hz, 1 H, Ar-7¹ H), 7.96 (s, 1 H, Ar-2¹), 8.35 (s, 1 H, Ar-2²); ¹³C NMR (400 MHz CDCl₃) ☐183.3, 147.1, 143.3, 141.6, 139.0, 136.7, 130.7, 124.1, 123.4, 123.2, 122.5, 120.2, 117.9, 111.1, 83.3, 55.7, 50.3, 47.2, 37.2, 36.8, 36.6, 34.8, 31.1, 30.3, 30.2, 27.0, 20.6, 19.2, 16.0

3β-(pyridine-3-ylmethoxy)-17-(1H-benzimidazol-1-yl) androsta-5,16-diene (VNPP415C (A15))

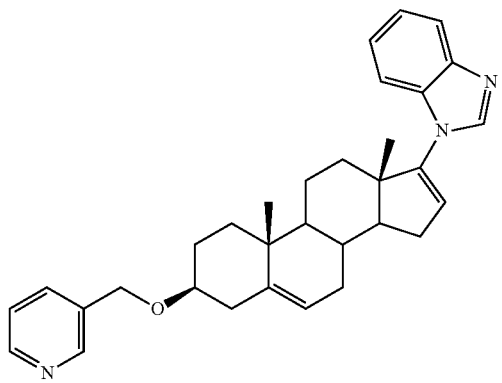 [SMILES: C[C@]12CC[C@H](OCc3cccnc3)CC1=CCC1C2CC[C@]2(C)C(n3cnc4ccccc43)=CCC12]

To a solution of VN124-1 (0.1 g, 0.257 mmol), Sodium hydride (0.02 g, 0.836 mmol) and DMF (2 mL) at room temperature under argon added 3-(iodomethyl) pyridine hydroiodide (0.16 g, 0.46 mmol). The reaction heated to 65° C., continued for 48 hr, cooled and then poured onto ice cold water, filtered and dried. Purification by FCC [petroleum ether/EtOAc (3:2)] gave VNPP415C(A15) (53 mg, 43%): mp 196-97° C.; $^1$H NMR (400 MHz, CDCl$_3$) δ 1.02 (s, 3 H, 18-CH$_3$), 1.07 (s, 3 H, 19-CH$_3$), 3.31 (m, 1 H, 3α-H), 4.59 (s, 2 H, —CH$_2$), 5.42 (d, J=5.38 Hz, 1 H, 6-H), 5.98 (dd, J=3.18, 1.71 Hz, 1 H, 16-H), 7.27-7.34 (m, 3 H, Ar-Hs), 7.47-7.51 (m, 1 H), 7.70 (d, J=7.82 Hz, 1 H), 7.78-7.85 (m, 1 H), 7.96 (s, 1 H, Ar-2$^1$ H), 8.54 (dd, J=5.01, 1.59 Hz, 1 H, Ar-6$^2$ H), 8.59 (d, J=1.71 Hz, 1 H, Ar-2$^2$ H); $^{13}$C NMR (101 MHz, CDCl$_3$) δ 149.14, 149.01, 147.23, 143.33, 141.64, 141.13, 135.28, 134.58, 134.37, 124.06, 123.39, 122.46, 121.19, 120.23, 111.14, 97.23, 78.86, 67.50, 55.90, 50.56, 47.25, 39.11, 37.11, 37.09, 34.89, 31.14, 30.38, 30.30, 28.34, 20.67, 19.32, 16.02

3β-(pyridine-4-ylmethoxy)-17-(1H-benzimidazol-1-yl) androsta-5,16-diene (VNPP414(A16))

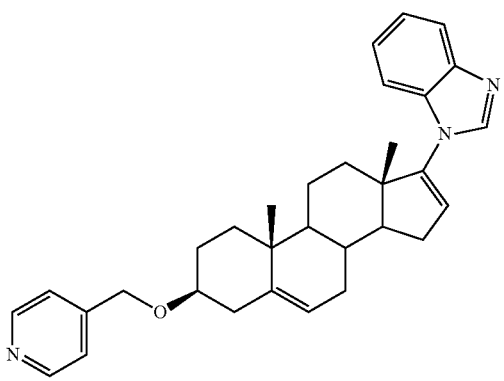 [SMILES: C[C@]12CC[C@H](OCc3ccncc3)CC1=CCC1C2CC[C@]2(C)C(n3cnc4ccccc43)=CCC12]

To a solution of VN124-1 (0.1 g, 0.257 mmol), Sodium hydride (0.185 g, 7.7 mmol) and DMF (2 mL) at room temperature under argon added 4-(bromomethyl)pyridine hydrobromide (0.2 g, 0.772 mmol). The reaction heated to 65° C., continued for 12 hr, cooled and then poured onto ice cold water, filtered and dried. Purification by FCC [petroleum ether/EtOAc (3:2)] gave VNPP414(A16) (15 mg, 12%): mp 166-67° C.; $^1$H NMR (400 MHz, CDCl$_3$) δ 1.02 (s, 3 H, 18-CH$_3$), 1.08 (s, 3 H, 19-CH$_3$), 3.30 (m, 1 H, 3α-H), 4.59 (s, 2 H, —CH$_2$), 5.42 (d, J=4.89 Hz, 1 H, 6-H), 5.98 (br. s., 1 H, 16-H), 7.27-7.34 (m, 4 H, aromatic-Hs), 7.49 (d, J=5.14 Hz, 1 H, Ar7$^1$-H), 7.81 (d, J=4.40 Hz, 1 H, Ar-6$^1$-H), 7.95 (s, 1 H, Ar-2$^1$-H), 8.57 (d, J=4.65 Hz, 2 H, Ar-2$^2$, 6$^2$-Hs); $^{13}$C NMR (101 MHz, CDCl$_3$) δ 149.8, 148.2, 141.6, 141.0, 134.5, 124.0, 123.3, 122.4, 121.7, 121.2, 120.2, 111.1, 79.1, 68.3, 55.9, 50.5, 47.2, 39.1, 37.1, 37.0, 34.8, 31.1, 30.3, 30.3, 28.3, 20.6, 19.3, 16.0; HRMS calcd 502.2828 (C$_{32}$H$_{37}$N$_3$O)Na$^+$, found 502.2834.

3β-(methoxy)-17-(1H-benzimidazol-1-yl) androsta-5,16-diene (VNPP412(A31))

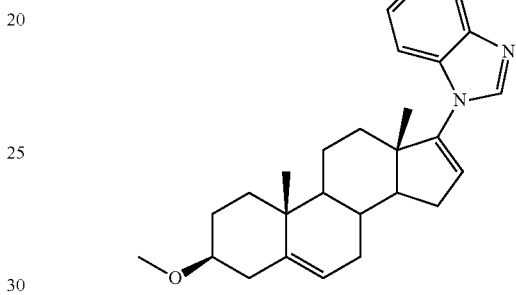

To a solution VN124-1 (0.1 g, 0.257 mmol), Sodium hydride (12.4 mg, 0.515 mmol) and DMF (2 mL) at room temperature under argon added MeI (75 mg, 0.515 mmol). The reaction continued for 1 hr and then poured onto ice cold water, extracted with EtOAc and organic solvent evaporated. The crude product was purified by FCC [petroleum ether/EtOAc/TEA (4:1:0.2)] to give VNPP412(A31) (0.08 g, 77%): mp 136-37° C.; $^1$H NMR (400 MHz, CDCl$_3$) δ 1.02 (s, 3 H, 18-CH$_3$), 1.05 (s, 3 H, 19-CH$_3$), 2.43 (d, J=13.69 Hz, 2 H), 3.08 (m, 1 H, 3α-H), 3.37 (s, 3 H, CH$_3$), 5.41 (br. s., 1 H, 6-H), 5.98 (br. s., 1 H, 16-H), 7.30 (m, 2 H, Ar-5$^1$, 6$^1$-Hs), 7.49 (d, J=3.34 Hz, 1 H, Ar-7$^1$-H), 7.81 (m, 1 H, Ar-4$^1$-H), 7.96 (s., 1 H, Ar-2$^1$-H); $^{13}$C NMR (101 MHz, CDCl$_3$) δ 147.2, 141.3, 124.0, 123.3, 122.4, 120.9, 120.2, 111.1, 80.1, 55.9, 55.6, 50.5, 47.2, 38.7, 37.1, 37.0, 34.9, 31.1, 30.3, 30.3, 27.9, 20.6, 19.3, 16.0; HRMS calcd 425.2563 (C$_{27}$H$_{34}$N$_2$O)Na$^+$, found 425.2566.

3-[{Trifluoromethyl-sulfonyl}-oxy]-estra-1,3,5-(10)-trien-17-one (VNPP308)

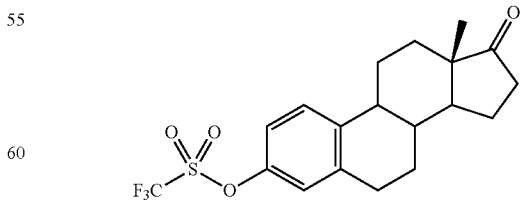

To estrone (2.5 g, 9.24 mmol) in DCM (40 mL) at 0° C. was added TEA (1.9 g, 18.5 mmol) and truffle anhydride (2.86 g, 10.17 mmol,). The reaction mixture was stirred at 0° C. for 1 h before the addition of saturated aqueous NaHCO$_3$ (40 mL). The phases were separated and the aqueous phase was extracted with DCM (2×40 mL). The combined organic phases are washed with brine (40 mL) and dried (Na$_2$SO$_4$). The filtrate was concentrated in vacuo and the residue was purified by short FCC [petroium ether/EtOAc (8:2)] to give VNPP308 (1.67 g, 99%): mp 99° C.; IR (Neat) 1736, 1487, 1420, 1209, 1138, 916, 829 c m-1; $^1$H NMR (400 MHz, CDCl3) δ 0.92 (s, 3 H, 18-CH$_3$), 1.43-1.71 (m, 7 H), 1.95-2.22 (m, 4 H), 2.30 (td, J=10.60, 4.39 Hz, 1 H, 12β-H), 2.37-2.45 (m, 1 H, 14-H), 2.48-2.58 (m, 1 H, 8-H), 2.95 (dd, J=8.66, 3.89 Hz, 2 H, 6-H), 7.00 (d, J=2.76 Hz, 1 H, 4-H), 7.03 (dd, J=8.64, 2.68 Hz, 1 H, 2-H), 7.34 (d, J=8.28 Hz, 1 H, 1-H Estra-1,3,5-(10)-trien-17-one-3-methylcarboxylate (VNPP309A)

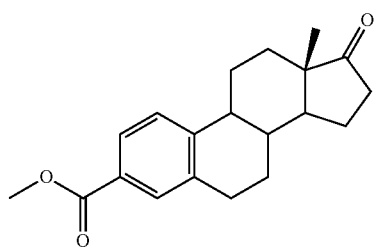 [SMILES: COC(=O)c1ccc2c(c1)CCC1C2CC[C@]2(C)C(=O)CCC12]

A mixture of VNPP308 (3 g, 7.46 mmol), Pd(II) acetate (0.12 g, 0.54 mmol), 1,3-bis-(diphenyl-phosphino)propane (dppp) (0.19 g, 0.46 mmol), TEA (2.36 g, 23.27 mmol), methanol (12 mL), and DMF (20 mL) were heated at 70° C. with a slow constant purging of carbon monoxide for 9 h. The reaction mixture was then cooled, poured into brine (100 mL), and extracted with EtOAc (3×100 mL), filtered through celite and dried with Na$_2$SO$_4$ and concentrated under vacuum to give crude product, which was then purified by FCC [petroleum ether/EtOAc (9.5:0.5, 9:1, 8.5:1.5 gradient)] to give first pure VNPP309A (0.75 g, 32.2%) mp. 120-122° C.; IR (Neat) 2931, 1731, 1717, 1441, 1290, 1260, 1199, 1174, 750 c m-1 $^1$H NMR (400 MHz, CDCl3) δ 0.92 (s, 3 H, 18-CH$_3$), 1.43-1.70 (m, 8H), 1.99 (d, J=12.05 Hz, 1 H,), 2.04-2.21 (m, 3 H), 2.47-2.57 (m, 1 H, 8-H), 2.94-3.00 (m, 2 H, 6-H), 3.90 (s, 3 H, CH$_3$), 7.36 (d, J=8.03 Hz, 1 H, 1-H), 7.78 (d, J=1.6 Hz, 1 H, 4-H), 7.80 (m, 1 H, 2-H)

Then UV inactive compound (Estrone) (1.2 g): mp 255-262° C.: IR (Neat) 3281, 1706, 1578, 1496, 1286, 1246, 1152, 1054, 815; $^1$H NMR (500 MHz, CDCl$_3$) δ 0.91 (s, 3H. 18-CH$_3$), 1.41-1.65 (m, 8 H), 1.93-2.08 (m, 3 H), 2.10-2.18 (m, 1 H), 2.21-2.27 (m, 1 H), 2.35-2.41 (m, 1 H,), 2.50 (dd, J=19.00, 8.62 Hz, 1 H), 2.87 (dd, J=6.56, 3.05 Hz, 2 H, 6-H), 4.62 (s, 1 H, —OH), 6.58 (d, J=2.3 Hz, 1 H, H-4), 6.64 (dd, J=8.32, 2.37 Hz, 1 H, H-2), 7.15 (d, J=8.24 Hz, 1 H, H-1); $^1$H NMR (400 MHz, DMSO-d6) δ 0.82 (s, 3 H), 1.31-1.40 (m, 3 H), 1.43-1.52 (m, 2 H), 1.56 (br. s., 1 H), 1.75 (d, J=8.56 Hz, 1 H), 1.94 (d, J=8.07 Hz, 2 H), 2.31 (d, J=5.14 Hz, 1 H), 2.75 (d, J=5.14 Hz, 2 H), 6.45 (s, 1 H), 6.51 (d, J=8.07 Hz, 1 H), 7.05 (d, J=8.56 Hz, 1 H), 9.00 (s, 1 H)

Estra-1,3,5-(10),16-tetraen-17-bromo-16-formyl-3-methylcarboxylate (VNPP315B)

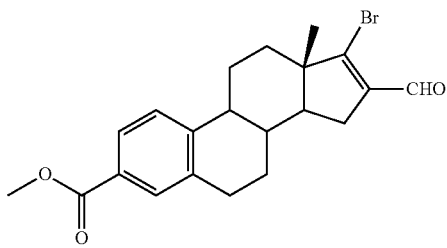 [SMILES: COC(=O)c1ccc2c(c1)CCC1C2CC[C@]2(C)C(Br)=C(C=O)CC12]

To ice cold DMF (2.5 mL) drop wise added phosphorus tribomide (1.44 g, 5.30 mmol) and stirred for 5 min. A solution of VNPP309A (0.75 g, 2.40 mmol) in dry CHCl$_3$ (5 mL) was added and refluxed for 5 h. It was then concentrated under vacuum, poured on to ice, extracted with EtOAc, organic phase dried and evaporated to get solid. Residue then moistened with THF, stirred with 20% HCl for 2 h, extracted with EtOAc, organic phase dried with Na$_2$SO$_4$ and evaporated. On purification by FCC [petroleum ether/EtOAc (9:1)] gave pure VNPP315B (0.5 g, 51.7%): mp. 149-150° C.; IR (Neat) 2936, 1708, 1668, 1578, 1435, 1291, 1260, 1193, 1108, 757 c m-1; $^1$H NMR (400 MHz, CDCl3) δ 0.97 (s, 3 H, 18-CH$_3$), 1.55 (s, 1 H), 1.64 (d, J=1.25 Hz, 1 H), 1.65-1.68 (m, 1 H), 1.68-1.71 (m, 1 H), 1.71-1.81 (m, 1 H), 1.96-2.04 (m, 2 H), 2.09-2.18 (m, 1 H), 2.39 (br. s., 1 H), 2.47-2.55 (m, 1 H), 2.65 (dd, J=14.68, 6.40 Hz, 1 H), 2.93-3.00 (m, 2 H, 6-H), 3.90 (s, 3 H, CH$_3$), 7.34 (dd, J=8.28, 1.0 Hz, 1H, 1-H), 7.78 (d, J=1.7 Hz,1 H, 4-H), 7.80 (dd, J=8.16, 1.88 Hz, 1 H, 2-H), 9.91 (s, 1 H, CHO)

Estra-1,3,5-(10), 16-tetraen-17-(1H-benzimidazol-1-yl)-16-formyl-3-methylcarboxylate (VNPP330)

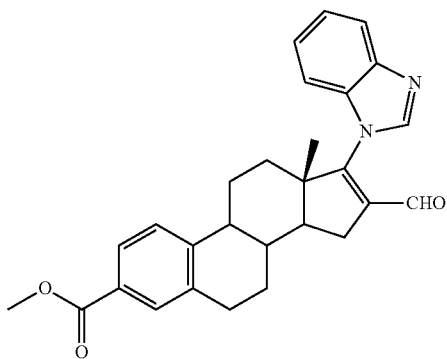 [SMILES: COC(=O)c1ccc2c(c1)CCC1C2CC[C@]2(C)C(n3cnc4ccccc43)=C(C=O)CC12]

A mixture of compound VNPP315B (0.25 g, 0.62 mmol), benzimidazole (0.22 g, 1.86 mmol), and K$_2$CO$_3$ (0.26 g, 1.86 mmol) in dry DMF (2 mL) was heated at 80° C. under argon for 1 h. After cooling to room temperature, the reaction mixture was poured onto ice-cold water (50 mL), and the resulting precipitate was filtered, washed with water, and dried. On purification over short FCC [hexane/EtOAc/TEA (10:5:0.1)] gave pure VNPP330 (0.26 g, 95%): mp 121-122° C.: IR (Neat) 2945, 1705, 1664, 1602, 1489, 1291, 1086, 748; $^1$H NMR (500 MHz, CDCl3) δ 1.02 (br. s., 3 H, 18-CH$_3$), 1.18-1.32 (m, 1 H), 1.53-1.64 (m, 4 H), 1.67 (d, J=9.61 Hz, 1 H), 1.76 (d, J=10.99 Hz, 2 H), 2.00 (br. s., 2

H), 2.04 (br. s., 1 H), 2.06-2.14 (m, 1 H), 2.38-2.61 (m, 3H), 2.88 (s, 3 H), 2.96 (s, 2 H), 2.98-3.08 (m, 2 H), 3.90 (s, 3 H, $CH_3$), 7.31-7.42 (m, 4 H, Ar—H), 7.80 (br. s., 2 H, Ar—H), 7.88 (dd, J=6.26, 2.90 Hz, 1 H, 2-H), 8.02 (br. s., 1 H, Ar-$2^1$-H), 9.62 (s, 1 H, CHO)

3-(methylcarboxylate)-17-(1H-benzimidazol-1-yl)-estra-1,3,5-(10)-trien (VNPP334 (E6))

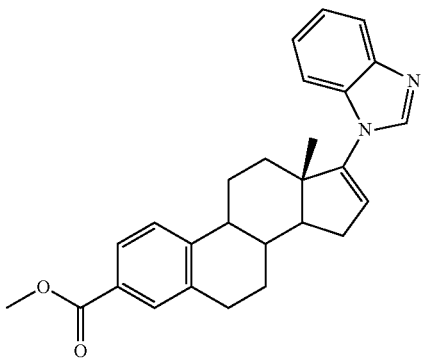 [SMILES: COC(=O)c1ccc2c(c1)CCC1C2CC[C@]2(C)C(n3cnc4ccccc43)=CCC12]

A solution of VNPP330 (0.22 g, 0.5 mmol) in dry benzonitrile (3 mL) was refluxed in the presence of 10% Pd on activated charcoal (0.11 g, i.e., 50% weight of the substrate) for 9 h. Then 0.05 g more catalyst added and refluxed for 12 h. After cooling to room temperature, the catalyst was removed by filtration through a Celite pad. The filtrate was evaporated, and the residue was purified by FCC [petroleum ether/EtOAc/TEA (8:2:0.5)] to give VNPP334 (0.12 g, 57%): mp: 165-167° C.: IR (Neat) 2927, 1716, 1486, 1451, 1288, 1265, 1108, 753, 737; $^1$H NMR (500 MHz, CDCl3) δ 1.03 (s, 3 H, 18-$CH_3$), 1.19-1.32 (m, 1 H), 1.53-1.61 (m, 1 H), 1.63-1.81 (m, 3 H), 1.87 (td, J=12.36, 3.20 Hz, 1 H), 1.93-2.12 (m, 3 H), 2.25-2.36 (m, 1 H), 2.42-2.59 (m, 3 H), 2.95-3.06 (m, 2 H, 6-Hs), 3.90 (s, 3 H, $CH_3$), 6.02 (br. s., 1 H, 16-H), 7.28-7.39 (m, 3 H, Ar—Hs), 7.51 (d, J=6.41 Hz, 1 H, Ar-$7^1$ H), 7.77-7.86 (m, 3 H, Ar—Hs), 8.00 (s, 1 H, Ar-$2^1$ H); CDCl3: 167.46, 147.38, 145.47, 143.44, 141.79, 136.91, 134.77, 130.42, 127.82, 127.06, 125.29 124.28, 123.68, 122.76, 120.43, 111.30, 55.31, 52.19, 47.76, 45.06, 36.82, 35.07, 30.23, 29.32, 27.22, 26.11, 16.37

3-(carboxylic acid)-17-(1H-benzimidazol-1-yl)-estra-1,3,5-(10)-trien (VNPP341 (E5))

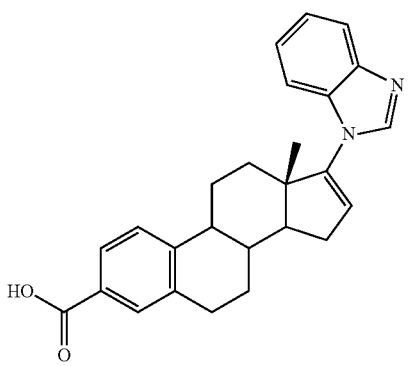 [SMILES: C[C@]12CCC3c4ccc(C(=O)O)cc4CCC3C1CC=C2n1cnc2ccccc21]

A suspension of VNPP334 (0.1 g, 0.24 mmol), 10% methanolic KOH (1.5 mL) and methanol (5 mL) refluxed for 2 h. Reaction mixture cooled, solid filtered and washed with cold methanol. On purification by FCC over short column [10% methanol in DCM] gave pure VNPP341 (0.09 g, 93%): mp 270° C. (decomp): IR (Neat) 1693, 1606, 1494, 1456, 1299, 1252, 1226, 1122, 756, 745, 737; $^1$H NMR (500 MHz, DMSO-$d_6$) δ 0.96 (s, 3 H, $CH_3$), 1.19-1.29 (m, 1 H), 1.42-1.58 (m, 2 H), 1.60-1.72 (m, 1 H), 1.76-1.90 (m, 2 H), 1.90-2.02 (m, 2 H), 2.36-2.49 (m, 3 H), 2.93 (d, J=5.34 Hz, 2 H, 6-H), 6.08 (br. s., 1 H, 16-H), 7.23-7.34 (m, 2 H, Ar—Hs), 7.37 (d, J=8.24 Hz, 1 H, 1-H), 7.59 (d, J=7.93 Hz, 1 H, Ar-$4^1$ H), 7.65-7.77 (m, 3 H), 8.30 (s, 1 H, Ar-$2^1$ H); $^{13}$C NMR (500 MHz, DMSO-$d_6$) δ 168.2, 147.2, 145.5, 143.5, 142.9, 137.1, 134.9, 130.4, 127.2, 125.7, 124.4, 123.9, 122.8, 120.2, 112.0, 55.1, 47.5, 44.8, 36.7, 34.5, 30.2, 29.2, 27.1, 26.1, 19.5, 16.4; $^1$H NMR (500 MHz, CDCl3) δ 1.06 (s, 3 H), 1.57-1.66 (m, 2 H), 1.67-1.81 (m, 3H), 1.85-1.96 (m, 2 H), 1.96-2.16 (m, 5 H), 2.29-2.39 (m, 2 H), 2.46-2.62 (m, 4 H), 3.04 (d, J=4.88 Hz, 2 H), 6.06 (br. s., 1 H), 7.32-7.37 (m, 2 H), 7.39 (d, J=8.09 Hz, 1 H), 7.51-7.58 (m, 1 H), 7.84-7.94 (m, 3 H), 8.06 (s, 1 H)

3-(Acetoxy)-estra-1,3,5-(10)-trien-17-one (VNPP310)

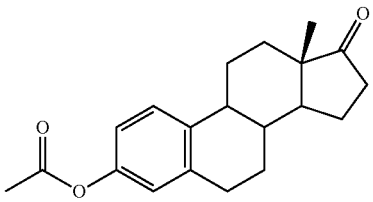 [SMILES: CC(=O)Oc1ccc2c(c1)CCC1C2CC[C@]2(C)C(=O)CCC12]

To a ice cold solution of estrone (3 g, 11.1 mmol) in pyridine (15 mL) added acetic anhydride (7.36 g, 72.1 mmol) and stirred at room temperature 16 h. Reaction mixture poured on ice water mixture (300 mL) and resulting solid filtered, washed with water and dried to gave pure VNPP310 (3.4 g, 98%): mp 222-223° C.; IR (Neat) 1759, 1732, 1491, 1365, 1210, 1183, 1019, 821; $^1$H NMR (300 MHz, CDCl$_3$) δ 0.89 (s, 3 H, 18-$CH_3$), 2.29 (s, 3 H, OAc), 2.85-2.96 (m, 2 H), 6.81 (m, 1 H, 1-H), 6.85 (d, J=8.78 Hz, 1 H, H-2), 7.29 (s, 1 H, H-4)

3-(Acetoxy)-17-(bromo)-16-(formyl)-estra-1,3,5-(10)-trien (VNPP311)

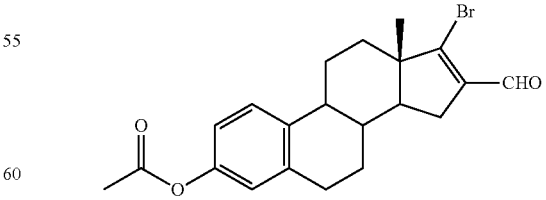

To ice cold DMF (6.5 mL) drop wise added phosphorus tribromide (2.88 g, 10.63 mmol) and stirred for 5 min. To this, a solution of VNPP310 (1.5 g, 5.4 mmol) in dry CHCl$_3$ (20 mL) was added and refluxed for 5 h. It was then concentrated under vacuum, poured on to ice, extracted with EtOAc, organic phase dried and evaporated to get solid. Residue then moistened with THF (~2 mL), stirred with 20% HCl (15 mL) for 2 h, extracted with EtOAc, organic phase dried with $Na_2SO_4$ and evaporated. On purification by FCC [petroleum ether/EtOAc (8:2)] gave pure VNPP311 (0.5 g, 26%): mp 123-25° C.; 1765, 1670, 1584, 1493, 1366, 1189, 1013, 897; $^1$H NMR (500 MHz, CDCl3) δ 0.96 (s, 3 H, 18-CH$_3$), 1.40-1.52 (m, 1 H), 1.57-1.70 (m, 3 H), 1.92-2.02 (m, 2 H), 2.12 (dd, J=14.72, 11.67 Hz, 1 H), 2.29 (s, 3 H, OAc), 2.46 (d, J=9.46 Hz, 1 H), 2.63 (dd, J=14.72, 6.33 Hz, 1 H), 2.85-2.96 (m, 2 H, C-6 Hs), 6.80-6.83 (m, 1 H, 1-H), 6.86 (dd, J=8.47, 2.37 Hz, 1 H, 2-H), 7.27 (s, 1 H, 4-H), 9.91 (s, 1 H, CHO); $C_{21}H_{23}BrO_3$, 402.083

Estra-1,3,5-(10),16-tetraen-17-bromo-16-formyl-3-ol (VNPP312)

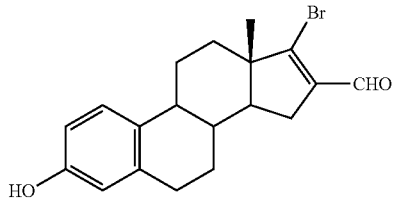 [SMILES: C[C@]12CCC3c4ccc(O)cc4CCC3C1CC(C=O)=C2Br]

A solution of VNPP311 (0.4 g, 1 mmol), 10% ethanolic KOH (2 mL) and ethanol (5 mL) stirred at room temperature over night. Reaction mixture evaporated, residue treated with cold water, filtered. On purification by FCC [petrolium ether/EtOAc (1:1)] gave (0.1 g, 28%): mp 149-151° C.; IR (Neat) 1718, 1609, 1462, 1497, 1287, 1250 1100, 837, 781; $^1$H NMR (500 MHz, CDCl3) δ 0.96 (s, 3 H, 18-CH$_3$), 1.38-1.49 (m, 1 H), 1.57-1.68 (m, 3 H), 1.75 (td, J=11.53, 6.59 Hz, 1 H), 1.90-2.02 (m, 2 H), 2.07-2.16 (m, 1 H), 2.29 (d, J=5.49 Hz, 1 H), 2.39-2.49 (m, 1 H), 2.63 (dd, J=15.37, 6.59 Hz, 1 H), 2.81-2.95 (m, 2 H, 6-H), 6.58 (s, 1 H, 4-H), 6.64 (d, J=8.78 Hz, 1 H, H-2), 7.13 (d, J=8.78 Hz, 1 H, H-1), 9.91 (s, 1 H, CHO) $C_{19}H_{21}BrO_2$, 360.072, Estra-1,3,5-(10),16-tetraen-17-(1H-benzimidazol-1-yl)-16-formyl-3-ol (VNPP314)

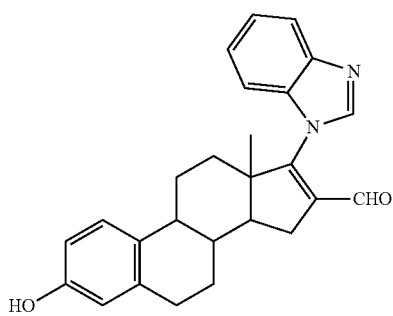 [SMILES: CC12CCC3c4ccc(O)cc4CCC3C1CC(C=O)=C2n1cnc2ccccc21]

A mixture of compound VNPP312 (0.42 g, 1.16 mmol), benzimidazole (0.41 g, 3.48 mmol), and $K_2CO_3$ (0.48 g, 3.48 mmol) in dry DMF (5 mL) was heated at 80° C. under argon for 5 h. After cooling to room temperature, the reaction mixture was poured onto ice-cold water (100 mL), and resulting solid filtered, washed with water, dried and carried to next step without purification. VNPP314 (0.39 g, 84%): mp 255-257° C.

3-(hydroxy)-17-(1H-benzimidazol-1-yl)-estra-1,3,5-(10)-trien (VNPP338 (E21))

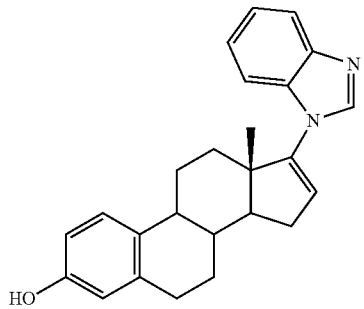 [SMILES: C[C@]12CCC3c4ccc(O)cc4CCC3C1CC=C2n1cnc2ccccc21]

A solution of VNPP314 (0.39 g, 0.97 mmol) in dry benzonitrile (3 mL) was refluxed in the presence of 10% Pd on activated charcoal (0.2 g, i.e., 50% weight of the substrate) for 12 h. Then 0.1 g more catalyst added at interval of 12 h×2 (all together 0.4 g). After cooling to room temperature, the catalyst was removed by filtration through a Celite pad. The filtrate was evaporated, and the residue was purified by FCC [petroleum ether/EtOAc/TEA (7.5:2:0.5) then (1:1:0.1)] to give VNPP338 (0.022 g, 6%): mp 110-112° C.; IR (Neat) 1666, 1608, 1493, 1455, 1289, 1225, 743; $^1$H NMR (500 MHz, CDCl$_3$) δ 1.02 (s, 3 H, 18-CH$_3$), 1.48-1.56 (m, 3 H), 1.58 (br. s., 7H), 1.70 (d, J=11.14 Hz, 1 H), 1.80-1.89 (m, 1 H), 1.90-2.05 (m, 3 H), 2.24-2.33 (m, 1 H), 2.33-2.45 (m, 2 H), 2.48-2.56 (m, 1 H), 2.88-2.95 (m, 1 H), 6.02 (br. s., 1 H, 16-H), 6.58-6.63 (dd, J=3.0 Hz, 1 H, 4-H), 6.65 (dd, J=8.39, 3.0 Hz, 1 H, 2-H), 7.13 (d, J=8.54 Hz, 1 H, 1-H), 7.28-7.35 (m, 2 H, Ar-6[1] and 5[1] Hs), 7.49-7.57 (m, 1 H, Ar-7[1] H), 7.79-7.87 (m, 1 H, Ar-4[1] H), 8.00 (s, 1 H, Ar-2[1]); $^{13}$C NMR (500 MHz, CDCl$_3$) δ 154.6, 147.4, 141.7, 138.0, 132.3, 131.7, 128.8, 127.5, 126.2, 123.8, 122.9, 120.1, 115.7, 113.2, 111.4, 55.2, 47.9, 44.4, 37.3, 35.1, 30.2, 29.6, 27.4, 26.4, 16.4

Additional Testing:

Luciferase Assay:

Reduction of DHT mediated AR transcriptional activity was performed after treatment of 10 μM concentration of compounds for 24 h.

Western Blotting:

The ability of various compounds to down-regulate AR protein expressions was determined by western blotting.

Cell Growth Inhibition (MTT Colorimetric Assay):

Compounds were evaluated on their ability to inhibit LNCaP cell (androgen sensitive AR-mutant), C4-2B and CWR22Rv1 (CRPC cell lines) viability at 1 and 10 μM concentrations by the MTT assy.

Structure Activity Relationship (SAR)

Figure 4:
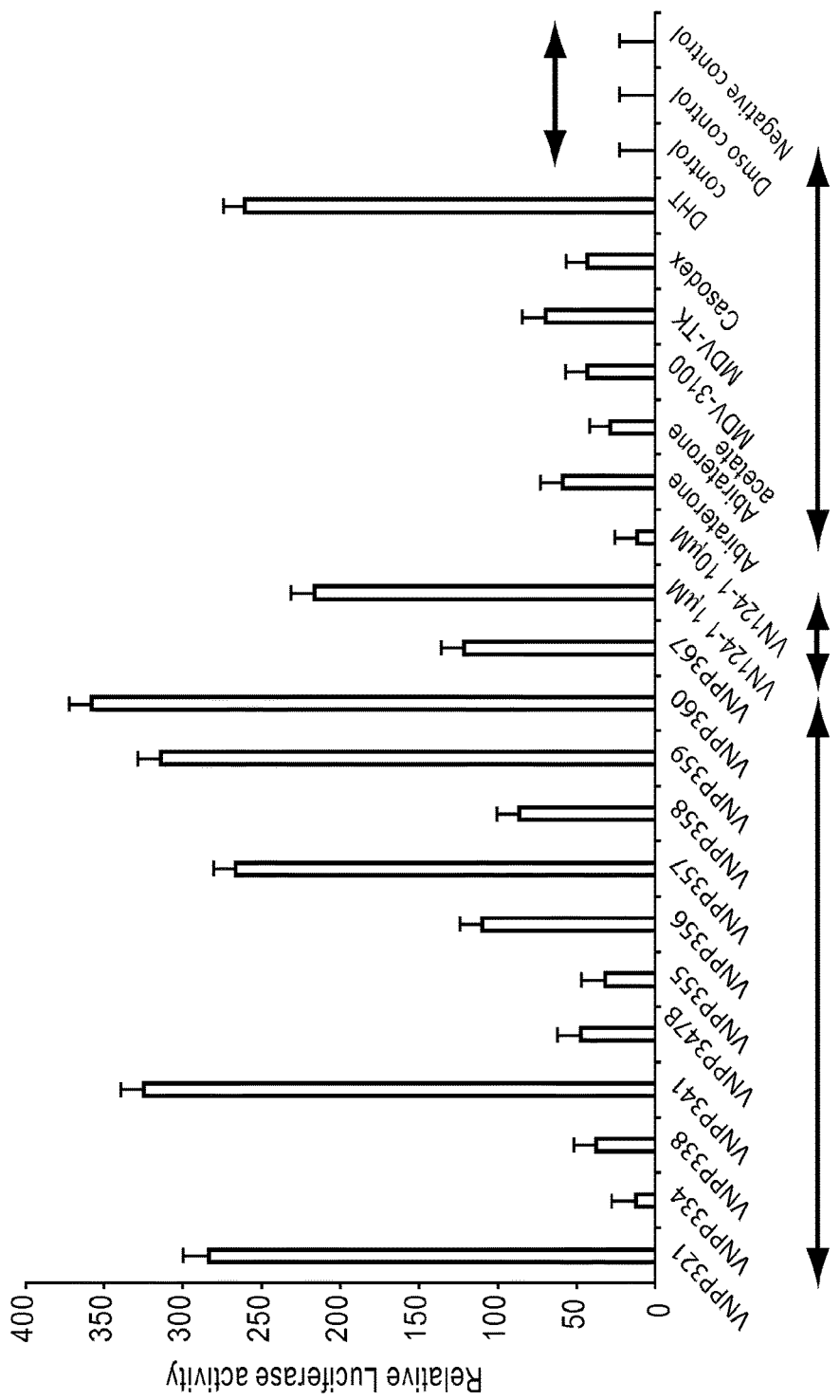
FIG. 4. Effects of Compounds on Transcriptional Activity of Luciferase Mediated Via LNCaP-AR in LNCaP-lu Prostate Cancer Cells.
Figure 5:
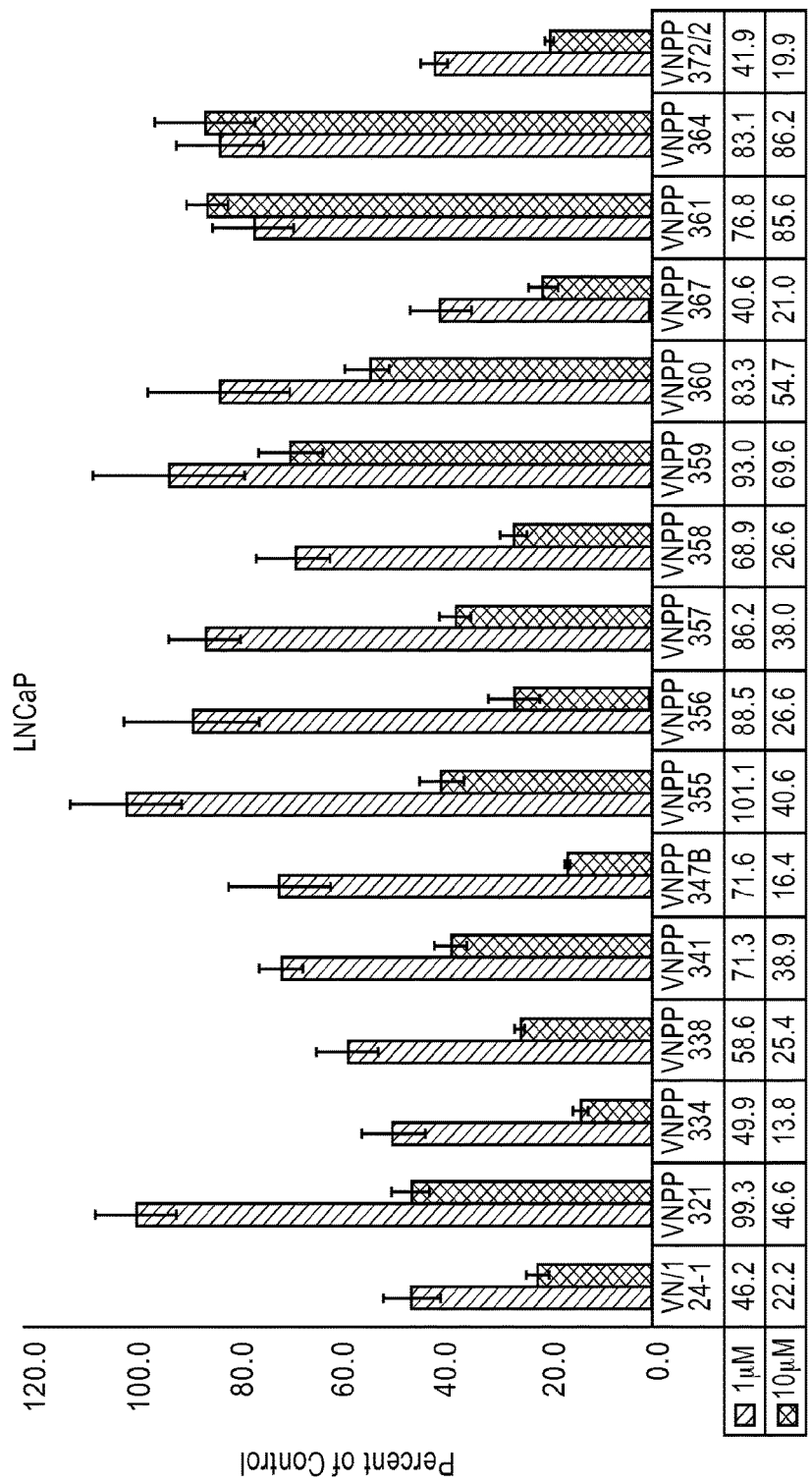
FIG. 5. Antiproliferative activity against androgen responsive LNCaP cells (A), CRPC cell line C4-2B (B) by MTT assay.
Figure 6:
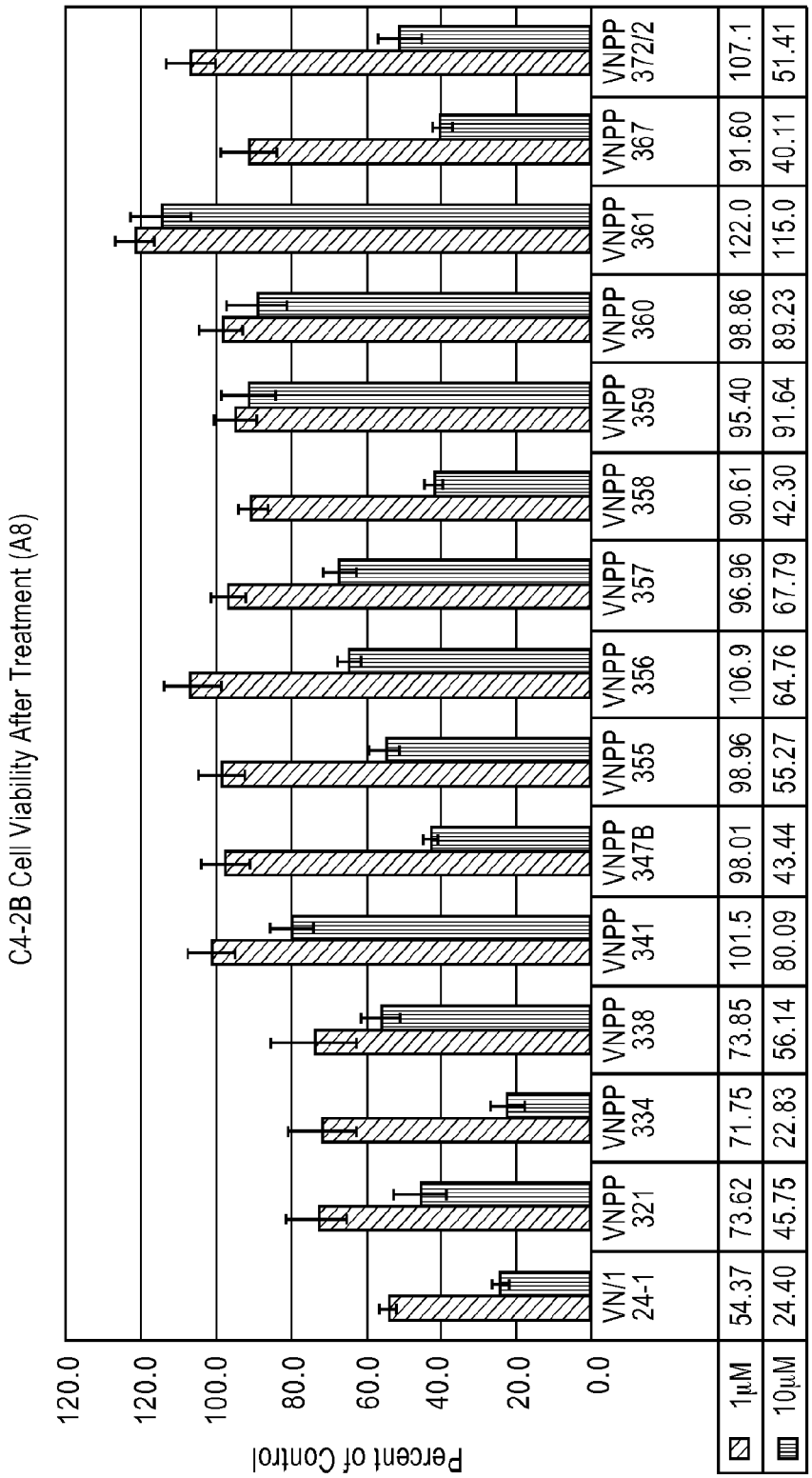
FIG. 6. Antiproliferative activity against androgen responsive cell line CRPC cell line C4-2B by MTT assay.
Figure 7:
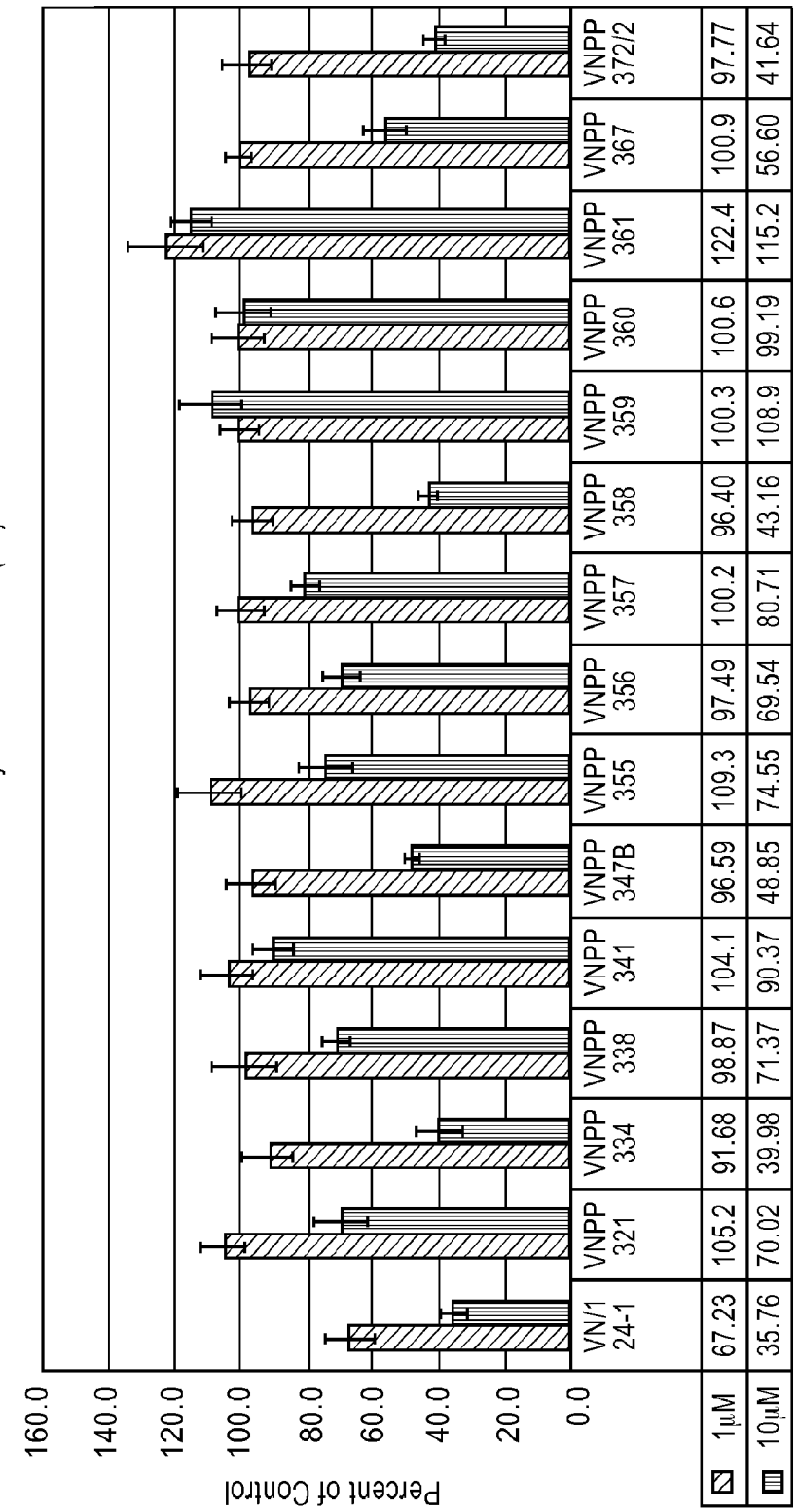
FIG. 7. Screening of new compounds (compared to VN/124-1) for inhibition of cell growth @ 1 and 10 μM using MTT assay.

Some nonsteroidal and steroidal agents reduced DHT mediated AR transcriptional activity in Luciferase assay (FIG. 4). Estrone-3-methyl ester derivative (VNPP334; Sch. 3) is a potent antiproliferative agent in LNCaP and C4-2B cell line, being more potent than compound VN/124-1 (FIGS. 5 and 6).

Of the nonsteroidal agents tested against LNCaP cell line (FIG. 5) methoxy substituted biphenyl with one carbon spacing (VNPP347B; Sch. 1) and naphthalene (VNPP372-2; Sch. 1) derivative displayed more potent anticancer activity in comparison to compound VN/124-1. Whereas, hydroxyl (VNPP356) and nitrile (VNPP358; Sch. 1) substituted biphenyls with one carbon spacing to BzIM group are as potent as compound VN/124-1.

Estrogen-3-methyl ester derivative (VNPP334; Sch. 3) is more potent than compound VN/124-1.

From above this limited SAR, it appears that biphenyl derivatives with two carbon spacing between BzIM group is detrimental to activity.

Substitution —COOH or 1H-terazole on biphenyl is also detrimental to activity.

Figure 8:
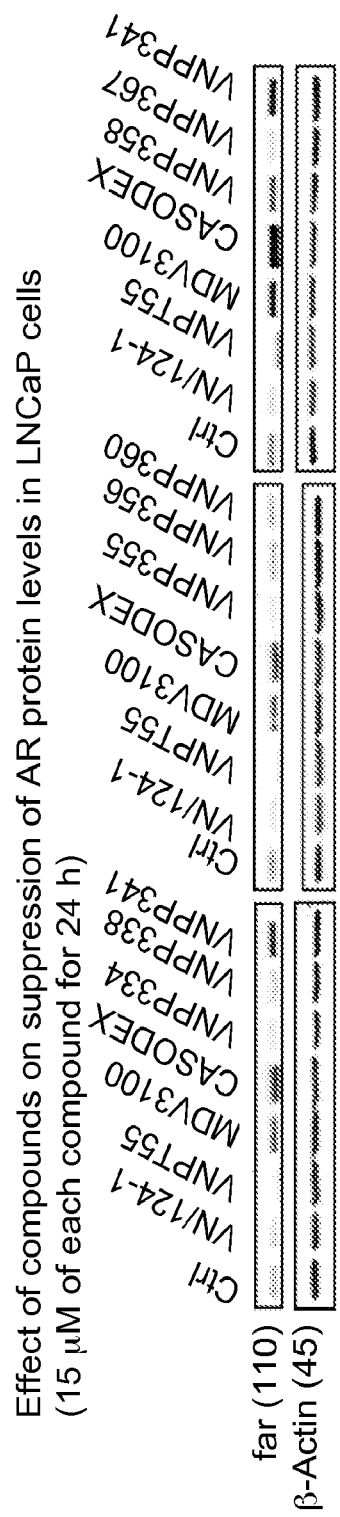
FIG. 8. Effect of compounds on suppression of AR protein levels in LNCaP cells (15 μM of each compound for 24 h.

Potent anticancer activity observed with VNPP334, VNPP367 possibly due to AR down-regulating action is supported by western blot (FIG. 8). In addition, equal potent anticancer activity to compound VN/124-1 is displayed by VNPP338, VNPP356, which are also potent AR down-regulating agents.

Two of moderately acting compounds (VNPP341, VNPP358) are AR up-regulators. Their observed anticancer activity may also be due to other yet unknown activities.

MDV3100 and Casodex are not AR down-regulating agents.

Effects of Compounds on Oncogenes.

In the experiments show in FIG. 9, LNCaP and CWR22Rv1 cells were treated VN/124-1 and analogs at varying time points and effects on significant cancer cells promoting genes investigated at the protein level.

Figure 9B:
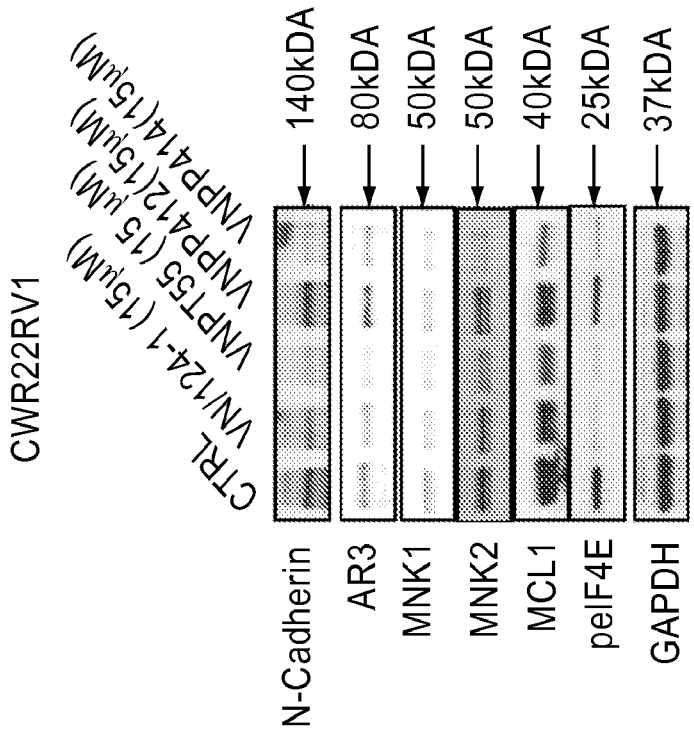
Figure 9A:
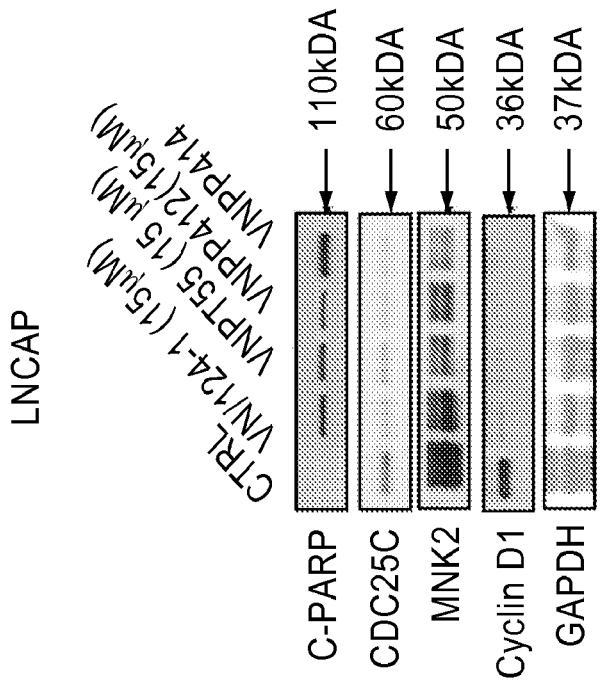
Figure 9D:
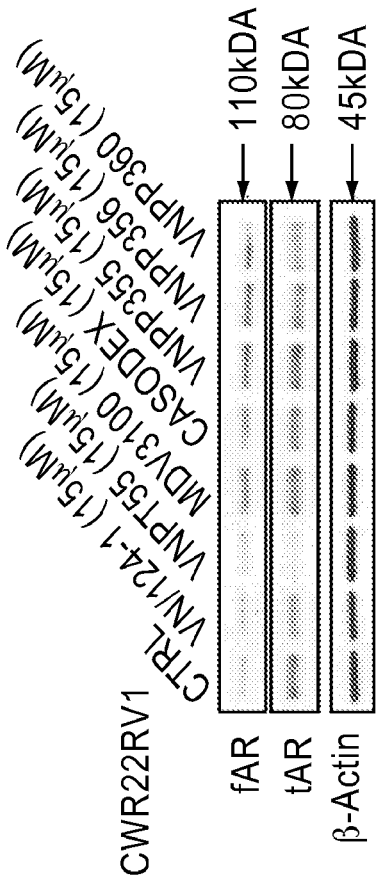
Figure 9C:
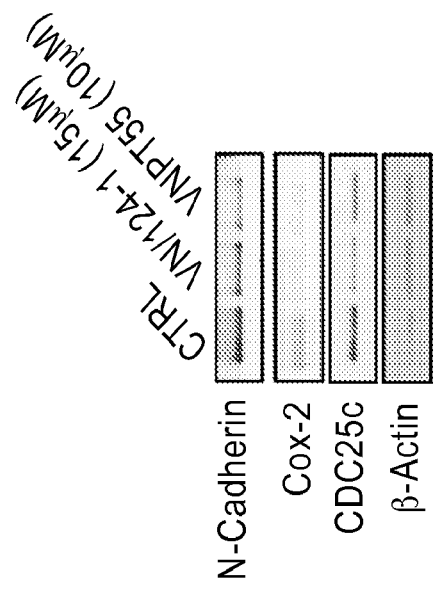

FIGS. 9A and 9C show, in LNCaP cells, Galeterone and analogs (VNPT55 and VNPP414) induced a significant increase in PARP cleavage (signature of apoptosis) and reduced the expression of CDC25c, Mnk2, Cyclin D1, Cox-2 and N-Cadherin.

Figure 9H:
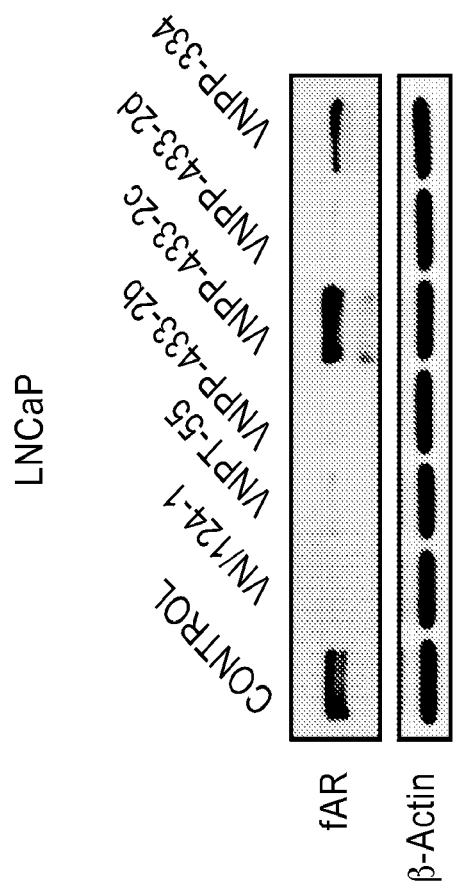
Figure 9G:
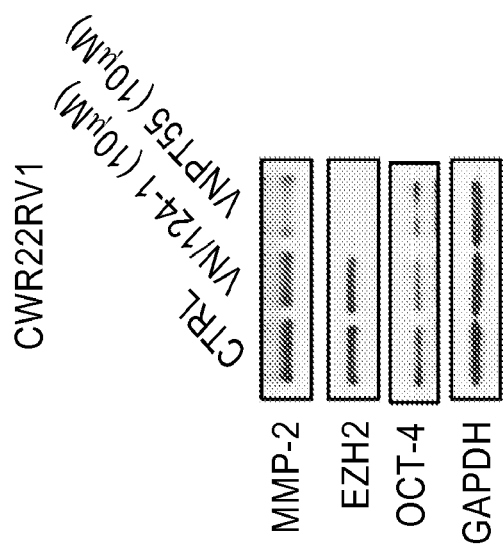

FIGS. 9B and 9G show in CWR22Rv1 cells Galeterone and analogs (VNPT55 and VNPP414) decreased the protein expression of N-Cadherin, AR3, Mnk1/2, MMP-2, Ezh2, Mcl-1(antiapoptotic protein) and also downregulated the phosphorylation of eIF4E.

FIGS. 9D, 9E and 9F show CWR22Rv1 were treated with other analogs of Galeterone and VNPP356, VNPP360, VNPP341, VNPP367, VNPP334 and VNPP338 showed activity (AR down-regulation) against full length AR and the splice variants ARs.

FIG. 9H shows activity (AR down-regulation) of VN-PP433-2b (VNPP-433-6β), VNPP-433-2c (VNPP433-3α (A3)), VNPP433-2d (VNPP433-3β (A1)), and VNPP-334 (A2) against full length AR.

FIG. 10 shows PC3 cells treated with Galeterone, VNPT55 and VNPP414 at 5 μM profoundly inhibit migration of PC3 cells after 12 hours.

FIGS. 93A, 9B, 9C & 9D show LNCaP, CWR22Rv1, PC3 and DU145 cells respectively were plated and treated with Galeterone, VNPT55, Abiraterone and MDV3100 for duration of 14 to 20 days and colony formation of the cells determined by staining. As compared to Abiraterone and MDv3100, Galeterone and VNPT55 profoundly inhibited colony formation of both AR positive and negative prostate cancer cells.

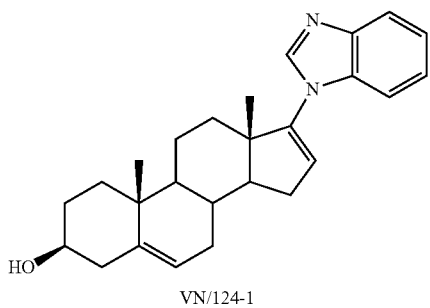

VN/124-1

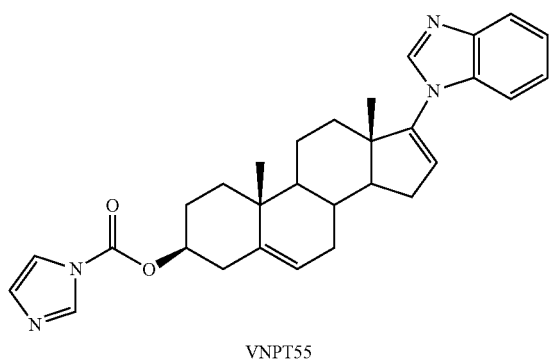

VNPT55

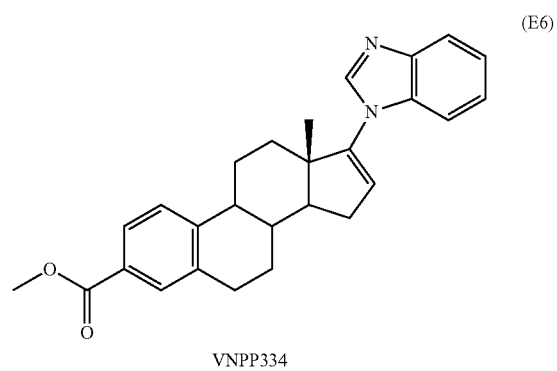

(E6)

VNPP334

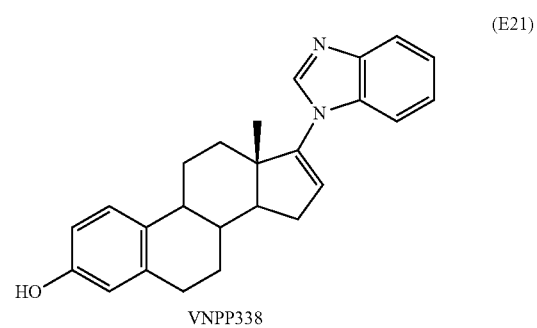

(E21)

VNPP338

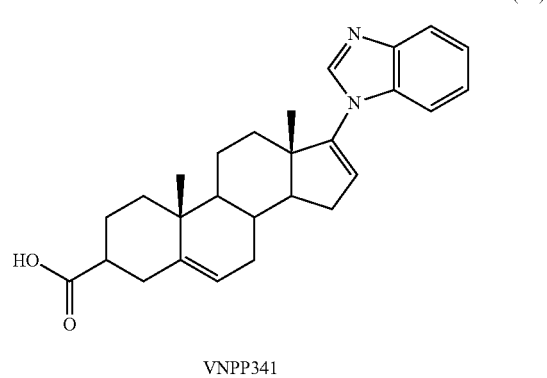

(E5)

VNPP341

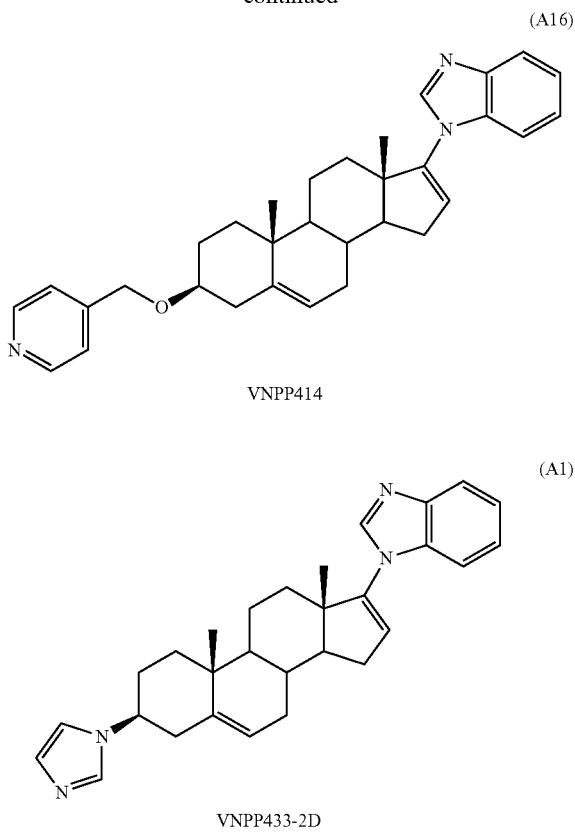

(A16) VNPP414

(A1) VNPP433-2D

TABLE 10

GI$_{50}$ values of VN/124-1 and its analogs

| Compounds | GI$_{50}$ Values (μM)[a] | | |
|---|---|---|---|
| | LNCaP (Low Passage) | LNCaP (High Passage) | CWR22Rv1 |
| VN/124-1 | 2.45 | 9.57 | 4.46 |
| MDV3100 | 4.85 | nd | nd |
| VNPT55 | 0.87 | 4.06 | 3.35 |
| VNPP334 (E6) | nd | 6.91 | 8.74 |
| VNPP414 (A16) | 0.87 | 2.45 | 3.24 |
| VNPP433-2d (A1) | 0.81 | 1.64 | 2.54 |

[a]The GI50 values were determined from dose-response curves (by nonlinear regression analysis using GraphPad Prism) compiled from at least three independent experiments, SEM <10%, and represents the compound concentration required to inhibit cell growth by 50%.
nd = not determined.

The new scaffolds (both steroidal and nonsteroidal) are well tolerated.

3-methylcarboxylate of estrone, methoxy of biphenyl with one carbon spacing and naphthalene derivatives displayed potent biological activity.

Determination of antiandrogenic and CYP17 inhibitory activity of novel agents may delineate their observed anticancer and ARDA activity.

Applicants' invention includes novel compounds and their use on modulation of the androgen receptor (AR). Applicants have evaluated their effects on AR and other prostate cancer oncogenic targets. In addition to modulation of AR (degradation of both full-length AR and splice variant AR), these novel compounds also degrade MAPK-interacting kinases (Mnk1/2) and modulation eukaryotic translation initiation factor 4 (eIF4E). As shown in FIG. 9A-H, 10 and Table 10, the lead compounds degrade Mnk1/2, blockeIF4E phosphorylation, inhibit cell growth, colonization, and migration and induce apoptosis. These effects are also superior to some FDA approved prostate cancer drugs.

Androgen receptor associated conditions that may be prevented and/or treated in the present invention include, but are not limited to, prostate cancer, castration resistant prostate cancer, bladder cancer, pancreatic cancer, hepatocellular carcinoma, benign prostatic hyperplasia (BPH), Kennedy's disease, androgenetic alopecia, breast cancer, androgen-insensitive syndrome, and spinal and bulbar muscular atrophy.

GI$_{50}$ Values
Cell Growth Inhibition (MTT Colorimetric Assay):

The cells were seeded in 96-well plates (Corning Costar) at a density of 5×10$^3$ cells per well. Cells were allowed to adhere to the plate for 24 hours and then treated with various concentrations of compounds dissolved in 95% EtOH. Cells were treated for 7 days with renewal of test compound and media on day 4. On the 7th day, medium was renewed and MTT (3-(4,5-dimethylthiazol-2-yl)-2,5-diphenyl-2H-tetrazolium bromide) (Sigma, St Louis, Mo., USA) solution (0.5 mg MTT per ml of media) was added to the medium such that the ratio of MTT: medium was 1:10. The cells were incubated with MTT for 2 hours. The medium was then aspirated and DMSO was added to solubilize the violet MTT-formazan product. The absorbance at 562 nm was measured by spectrophotometry (Biotek Inc.). The results are shown below.

Steroidal VNPP Compounds

| Compound | Low Passage LNCaP | High Passage LNCaP | CWR22Rv1 |
|---|---|---|---|
| VN/124-1 | | 3.93 | 8.91 |
| MDV-3100 | | 4.85 | |
| Abiraterone Acetate | | | |
| VNPP55 | | 4.06 | 4.46 |

-continued
| Compound | Low Passage LNCaP | High Passage LNCaP | CWR22Rv1 |
|---|---|---|---|
| VNPP334 | | 6.91 | 8.74 |
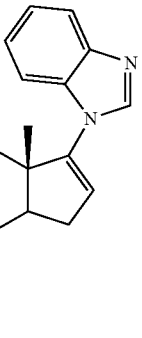
| | | | |
|---|---|---|---|
| VNPP397 | | 9.57 | 7.52 |
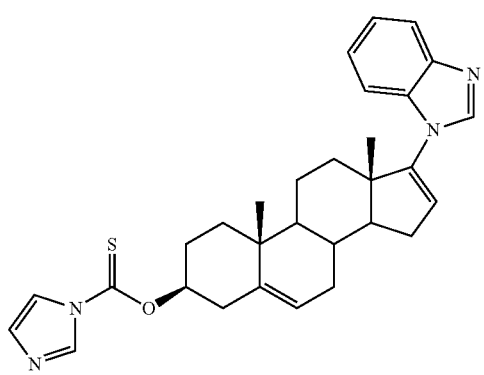 [SMILES: C[C@]12CC[C@H](OC(=S)n3ccnc3)CC1=CCC1C2CC[C@]2(C)C(n3cnc4ccccc43)=CCC12]
| | | | |
|---|---|---|---|
| VNPP412 | | 8.71 | 7.50 |
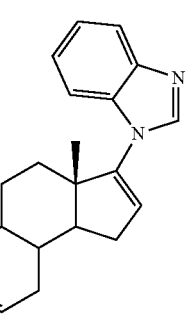
| | | | |
|---|---|---|---|
| VNPP414 | 0.87 | 2.45 | 3.24 |
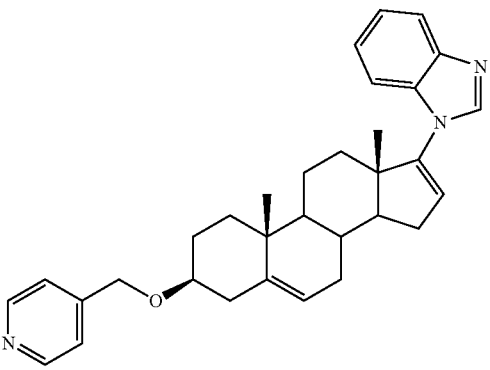 [SMILES: C[C@]12CC[C@H](OCc3ccncc3)CC1=CCC1C2CC[C@]2(C)C(n3cnc4ccccc43)=CCC12]

-continued
| Compound | Low Passage LNCaP | High Passage LNCaP | CWR22Rv1 |
|---|---|---|---|
| VNPP433-6β | | 6.61 | 12.30 |
| 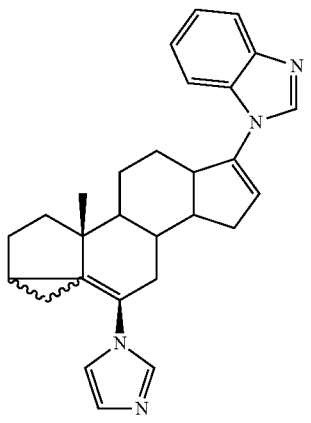 | | | |
| VNPP433-3α | 4.04 | 8.91 | 9.88 |
| 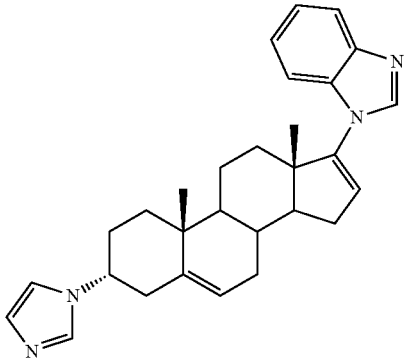 [SMILES: C[C@]12CC[C@@H](n3ccnc3)CC1=CCC1C2CC[C@]2(C)C(n3cnc4ccccc43)=CCC12] | | | |
| VNPP433-3β | 0.81 | 1.64 | 2.54 |
| 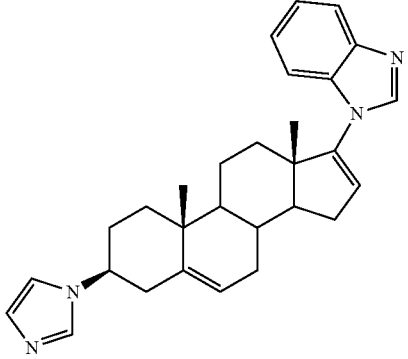 [SMILES: C[C@]12CC[C@H](n3ccnc3)CC1=CCC1C2CC[C@]2(C)C(n3cnc4ccccc43)=CCC12] | | | |

Non-steroidal VNPP Compounds

| Compound | Low Passage LNCaP | High Passage LNCaP | CWR22Rv1 |
|---|---|---|---|
| VN/124-1 | | 3.93 | 8.91 |
| MDV-3100 | | 4.85 | |
| Abiraterone Acetate | | | |
| VNPP347B | | 4.41 | 14.00 |
| VNPP358 | 3.71 | 3.50 | 10.47 |
| VNPP372/2 | 5.77 | 6.09 | 8.91 |

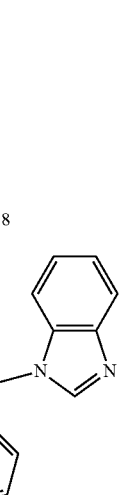
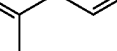

-continued

| Compound | Low Passage LNCaP | High Passage LNCaP | CWR22Rv1 |
|---|---|---|---|
| VNPP431 | 5.23 | 3.14 | 4.78 |

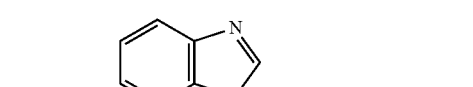

Pharmaceutical Composition/Formulation

A pharmaceutical composition, as used herein, refers to a mixture of a compound of the invention with other chemical components, such as carriers, stabilizers, diluents, dispersing agents, suspending agents, thickening agents, and/or excipients. The pharmaceutical composition facilitates administration of the compound to an organism. Pharmaceutical composition containing a compound of the invention can be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, optic, nasal, and topical administration. One may administer the compound in a local rather than systemic manner, for example, via injection of the compound directly into an organ, often in a depot or sustained release formulation. Furthermore, one may administer pharmaceutical composition containing a compound of the invention in a targeted drug delivery system, for example, in a liposome coated with organ-specific antibody. The liposomes will be targeted to and taken up selectively by the organ. In addition, the pharmaceutical composition containing a compound of the invention may be provided in the form of a rapid release formulation, in the form of an extended release formulation, or in the form of an intermediate release formulation. For oral administration, a compound of the invention can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. In certain instances, a gelatin is alkaline processed. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner. Parental injections may involve for bolus injection or continuous infusion. The pharmaceutical composition of a compound of the invention may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In some embodiments, pharmaceutical formulations are prepared as an amorphous solid dispersion. For example, the pharmaceutical formulation is a spray-dried formulation of the active compound in a polymer matrix. The pharmaceutical formulation may also be prepared by hot melt extrusion.

A compound of the invention can be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives. Formulations suitable for transdermal administration of compounds of the invention may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of a compound of the invention can be accomplished by means of iontophoretic patches and the like. Additionally, transdermal patches can provide controlled delivery of a compound of the invention. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, a compound of the invention may be in a form as an aerosol, a mist or a powder. Pharmaceutical compositions of the invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

A compound of the invention may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In practicing the methods of treatment or use provided herein, therapeutically effective amounts of a compound of the invention provided herein are administered in a pharmaceutical composition to a mammal having a disease or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures. Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions comprising a compound of the invention may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent or excipient and a compound of the invention described herein as an active ingredient in free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins1999), herein incorporated by reference in their entirety.

Methods of Administration and Treatment Methods

A compound of the invention can be used in the preparation of medicaments for the treatment of diseases or conditions in which steroid hormone nuclear receptor activity contributes to the pathology and/or symptoms of the disease. In addition, a method for treating any of the diseases or conditions described herein in a subject in need of such treatment, involves administration of pharmaceutical compositions containing at least one compound of the invention, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition, or to cure, heal, improve, or ameliorate the condition itself. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease or condition is retained. Patients can, however, require intermittent treatment on a long-term basis upon any recurrence of symptoms.

In certain instances, it may be appropriate to administer therapeutically effective amounts of at least one of the compounds described herein (or a pharmaceutically acceptable salts, pharmaceutically acceptable N-oxides, pharmaceutically active metabolites, pharmaceutically acceptable prodrugs, and pharmaceutically acceptable solvates thereof) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. In any case, regardless of the disease or condition being treated, the overall benefit experienced by the patient may simply be additive of the two therapeutic agents or the patient may experience a synergistic benefit. Where the compounds described herein are administered in conjunction with other therapies, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is one of the compounds described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents. Multiple therapeutic combinations are envisioned.

In addition, a compound of the invention may also be used in combination with procedures that may provide additional or synergistic benefit to the patient. By way of example only, patients are expected to find therapeutic and/or prophylactic benefit in the methods described herein, wherein pharmaceutical composition of the invention and/or combinations with other therapeutics are combined with genetic testing to determine whether that individual is a carrier of a mutant gene that is known to be correlated with certain diseases or conditions. A compound of the invention and combination therapies can be administered before, during or after the occurrence of a disease or condition, and the timing of administering the composition containing a compound can vary. Thus, for example, the compounds can be used as a prophylactic and can be administered continuously to subjects with a propensity to conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. a compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 3 years, and in some embodiments from about 1 month to about 10 years.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The invention claimed is:

1. A method of treating cancer comprising administering an effective amount of a compound selected from the group consisting of
   3β-(1H-imidazol-1-yl)-17-(1H-benzimidazol-1-yl)androsta-5,16-diene (VNPP433-3β (A1)),
   3β-(pyridine-4-ylmethoxy)-17-(1H-benzimidazol-1-yl)androsta-5,16-diene (VNPP414(A16)),
   6-(3-benzimidazolylphenyl)naphthalen-2-ol (VNPP372/2 (Na1)), and
   N-(3-benzimidazolylphenyl)[(4-methoxyphenyl) sulphonyl]amine (VNPP431(SulAmd2))
   to a patient in need thereof,
   wherein said cancer is prostate cancer or castration resistant human prostate cancer.

2. The method of claim 1, wherein said cancer is prostate cancer.

3. The method of claim 1, wherein said cancer is castration resistant human prostate cancer.

4. A method of degrading a full length androgen receptor or a splice variant androgen receptor, the method comprising administering an effective amount of a compound selected from the group consisting of
   3β-(1H-imidazol-1-yl)-17-(1H-benzimidazol-1-yl)androsta-5,16-diene (VNPP433-3β (A1)),
   3β-(pyridin-4-ylmethoxy)-17-(1H-benzimidazol-1-yl)androsta-5,16-diene (VNPP414(A16),
   6-(3-benzimidazolylphenyl)naphthalen-2-ol (VNPP372/2 (Na1)), and
   N-(3-benzimidazolylphenyl)[(4-methoxyphenyl) sulphonyl]amine (VNPP431(SulAmd2))
   to a patient in need thereof.

5. A method of inhibiting proliferation of androgen sensitive cell line comprising administering an effective amount of a compound selected from the group consisting of
   3β-(1H-imidazol-1-yl)-17-(1H-benzimidazol-1-yl)androsta-5,16-diene (VNPP433-3β (Al)),
   3β-(pyridin-4-ylmethoxy)-17-(1H-benzimidazol-1-yl)androsta-5,16-diene (VNPP414(A16),
   6-(3-benzimidazolylphenyl)naphthalen-2-ol (VNPP372/2 (Na1)), and
   N-(3-benzimidazolylphenyl)[(4-methoxyphenyl) sulphonyl]amine (VNPP431(SulAmd2))
   to a patient in need thereof.

6. A method of treating cancer, comprising administering an effective amount of a compound selected from the group consisting of 3β-(1H-imidazol-1-yl)-17-(1H-benzimidazol-1-yl)androsta-5,16-diene (VNPP433-3β (A1)), and 3β-(pyridin-4-ylmethoxy)-17-(1H-benzimidazol-1-yl)androsta-5,16-diene (VNPP414 (A16)) to a patient in need thereof,
   wherein the cancer is at least one selected from the group consisting of prostate cancer and castration resistant prostate cancer.

7. The method of treating cancer according to claim 6, wherein the compound is 3,β-(1H-imidazol-1-yl)-17-(1H-benzimidazol-1-yl)androsta-5,16-diene (VNPP433-3β (A1)).

8. The method of treating cancer according to claim 6, wherein the compound is 3β-(pyridin-4-ylmethoxy)-17-(1H-benzimidazol-1-yl)androsta-5,16-diene (VNPP414 (A16)).

9. The method of treating cancer according to claim 6, wherein the cancer is prostate cancer.

10. The method of treating cancer according to claim 6, wherein the cancer is castration resistant prostate cancer.

* * * * *

UNITED STATES PATENT AND TRADEMARK OFFICE
CERTIFICATE OF CORRECTION

Page 1 of 2

PATENT NO. : 9,694,005 B2
APPLICATION NO. : 14/781437
DATED : July 4, 2017
INVENTOR(S) : Vincent C. O. Njar and Puranik Purushottamachar It is certified that error appears in the above-identified patent and that said Letters Patent is hereby corrected as shown below:

In the Claims

At Column 55, Line 66:
Change "(example (A1)"
To be -- (Example A1) --.

At Column 55, Line 67:
Change "(example Example A3)"
To be -- (Example A3) --.

At Column 56, Line 3:
Change "andorostene derivative"
To be -- androstene derivative --.

At Column 62, Lines 21-22:
Change "compound A"
To be -- compound E --.

At Column 63, Line 1:
Change "(example (A1)"
To be -- (Example A1) --.

At Column 63, Line 2:
Change "(example Example A3)"
To be -- (Example A3) --.

At Column 63, Line 5:
Change "andorostene derivative molecule. See formula A"
To be -- estrogen derivative molecule. See formula E --.

Signed and Sealed this
Second Day of July, 2019

Andrei Iancu
*Director of the United States Patent and Trademark Office*

CERTIFICATE OF CORRECTION (continued)
U.S. Pat. No. 9,694,005 B2

At Column 70, TABLE 9:
For each of compounds E1 to E32, the portion of the compound name reading
"-estra-1,3,5-(10)-trien"
Should read -- -estra-1,3,5-(10), 16-tetraen --.

At Column 71, TABLE 9-continued:
For each of compounds E33 to E40, the portion of the compound name reading
"-estra-1,3,5-(10)-trien"
Should read -- -estra-1,3,5-(10), 16-tetraen --.

At Column 105, Lines 7-8:
Change "3-(methylcarboxylate)-17-(1$H$-benzimidazol-1-yl)-estra-1,3,5-(10)-trien (VNPP334 (E6))"
To be -- 3-(methylcarboxylate)-17-(1$H$-benzimidazol-1-yl)-estra-1,3,5-(10), 16-tetraen (VNPP334 (E6)) --.

At Column 105, Lines 48-49:
Change "3-(carboxylic acid)-17-(1$H$-benzimidazol-1-yl)-estra-1,3,5-(10)-trien (VNPP341 (E5))"
To be -- 3-(carboxylic acid)-17-(1$H$-benzimidazol-1-yl)-estra-1,3,5-(10), 16-tetraen (VNPP341 (E5)) --.

At Column 106, Lines 49-50:
Change "3-(Acetoxy)-17-(bromo)-16-(formyl)-estra-1,3,5-(10)-trien (VNPP311)"
To be -- 3-(Acetoxy)-17-(bromo)-16-(formyl)-estra-1,3,5-(10), 16-tetraen (VNPP311) --.

At Column 108, Lines 1-2:
Change "3-(hydroxy)-17-(1$H$-benzimidazol-1-yl)-estra-1,3,5-(10)-trien (VNPP338 (E21))"
To be -- 3-(hydroxy)-17-(1$H$-benzimidazol-1-yl)-estra-1,3,5-(10), 16-tetraen (VNPP338 (E21)) --.

UNITED STATES PATENT AND TRADEMARK OFFICE
CERTIFICATE OF CORRECTION

Page 1 of 1

PATENT NO. : 9,694,005 B2
APPLICATION NO. : 14/781437
DATED : July 4, 2017
INVENTOR(S) : Vincent C. O. Njar et al.

It is certified that error appears in the above-identified patent and that said Letters Patent is hereby corrected as shown below:

On the Title Page

<u>Item (72):</u>
Change the second inventor's name from:
"Puranik Purushottamachar, Gaithersburg, MD (US)"
To be:
-- Purushottamachar Puranik, Gaithersburg, MD (US) --

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*